(12) United States Patent
Swann et al.

(10) Patent No.: US 11,585,282 B1
(45) Date of Patent: Feb. 21, 2023

(54) FUEL CHARACTERISTICS

(71) Applicant: ROLLS-ROYCE plc, London (GB)

(72) Inventors: Peter Swann, Derby (GB); Craig W Bemment, Derby (GB); Alastair G Hobday, Derby (GB); Benjamin J Keeler, Derby (GB); Christopher P Madden, Derby (GB)

(73) Assignee: ROLLS-ROYCE plc, London (GB)

( * ) Notice: Subject to any disclaimer, the term of this patent is extended or adjusted under 35 U.S.C. 154(b) by 0 days.

(21) Appl. No.: 17/853,291

(22) Filed: Jun. 29, 2022

(30) Foreign Application Priority Data

Dec. 21, 2021 (GB) ..................................... 2118653

(51) Int. Cl.
*F02C 9/40* (2006.01)
*F02C 9/28* (2006.01)
*F01D 21/00* (2006.01)

(52) U.S. Cl.
CPC .............. *F02C 9/40* (2013.01); *F01D 21/003* (2013.01); *F02C 9/28* (2013.01); *F05D 2220/323* (2013.01); *F05D 2260/83* (2013.01); *F05D 2270/07* (2013.01); *F05D 2270/71* (2013.01)

(58) Field of Classification Search
CPC . B64D 37/14; B64D 37/16; F02C 9/28; F02C 9/40
See application file for complete search history.

(56) References Cited

U.S. PATENT DOCUMENTS

| 2008/0183362 A1* | 7/2008 | Dooley | F02C 3/20 |
| | | | 701/100 |
| 2009/0319153 A1* | 12/2009 | Bradley | F02C 7/22 |
| | | | 701/103 |
| 2019/0112067 A1* | 4/2019 | Fregnani | G01N 9/36 |

OTHER PUBLICATIONS

ASTM Standard D7566, "Standard Specification for Aviation Turbine Fuel Containing Synthesized Hydrocarbons." ASTM International, Jul. 2021.

* cited by examiner

*Primary Examiner* — Scott J Walthour
(74) *Attorney, Agent, or Firm* — Oliff PLC

(57) ABSTRACT

A method of identifying a fuel contained in a fuel tank of an aircraft and arranged to power a gas turbine engine of the aircraft is performed by processing circuitry of the aircraft and includes: obtaining at least one fuel characteristic of any fuel already present in the fuel tank prior to refuelling; determining at least one fuel characteristic of a fuel added to the fuel tank on refuelling; and calculating at least one fuel characteristic of the resultant fuel in the fuel tank after refuelling. The method may further controlling the propulsion system of the aircraft based on the calculated at least one fuel characteristic of the resultant fuel in the fuel tank after refuelling.

19 Claims, 11 Drawing Sheets

FUEL CHARACTERISTICS

CROSS-REFERENCE TO RELATED APPLICATIONS

This specification is based upon and claims the benefit of priority from UK Patent Application Number 2118653.1 filed on 21 Dec. 2021, the entire contents of which are incorporated herein by reference.

BACKGROUND

Field of the Disclosure

The present disclosure relates to aircraft propulsion systems, and to methods of operating aircraft involving the management of fuels of different types, including detection of fuel properties and actions taken to improve aircraft performance based on the data acquired, and to methods of modifying aircraft so as to allow such methods to be implemented.

Description of the Related Art

There is an expectation in the aviation industry of a trend towards the use of fuels different from the traditional kerosene-based jet fuels generally used at present. These fuels may have differing fuel characteristics, for example having either or both of a lower aromatic content and lower sulphur content, relative to petroleum-based hydrocarbon fuels.

Thus, there is a need to take account of fuel properties in light of the increased possibility of variation, and to adjust the control and management of aircraft propulsion systems and fuel supplies for these new fuels.

SUMMARY

According to a first aspect there is provided a method of identifying a fuel contained in a fuel tank of an aircraft and arranged to power a gas turbine engine of the aircraft, the method being performed by processing circuitry of the aircraft and comprising:
  obtaining one or more fuel characteristics of any fuel already present in the fuel tank prior to refuelling;
  determining one or more fuel characteristics of a fuel added to the fuel tank on refuelling; and
  calculating one or more fuel characteristics of the resultant fuel in the fuel tank after refuelling.

This approach may be referred to as an active infinite summing approach, as action is taken to make and continuously update a record of the fuel onboard an aircraft. The method may be performed for each of multiple fuel tanks of the aircraft separately, or for the overall fuel onboard the aircraft irrespective of in which tank it is held.

The obtaining the one or more fuel characteristics of any fuel already present in the fuel tank prior to refuelling may comprise obtaining those characteristics from computational storage, detecting those characteristics directly, or determining those characteristics from other detected parameters.

The step of obtaining one or more fuel characteristics of any fuel already present in the fuel tank prior to refuelling may comprise detecting one or more features of the composition of the fuel already present in the fuel tank.

The step of obtaining one or more fuel characteristics of any fuel already present in the fuel tank prior to refuelling may comprise obtaining the result of an earlier determination performed using the method of identifying a fuel described above for this first aspect.

The step of obtaining one or more fuel characteristics of any fuel already present in the fuel tank prior to refuelling may comprise maintaining current fuel characteristic data by updating the fuel characteristics of the fuel present in the fuel tank following each refuelling of the aircraft.

The step of determining one or more fuel characteristics of the fuel added to the fuel tank on refuelling may comprise reading a barcode associated with the provided fuel.

The fuel characteristics may be or comprise parameters of a hydrocarbon distribution of the fuel. The fuel characteristics may be or comprise:
  i. the percentage of sustainable aviation fuel in the fuel;
  ii. the aromatic hydrocarbon content of the fuel;
  iii. the multi-aromatic hydrocarbon content of the fuel;
  iv. the percentage of nitrogen-containing species in the fuel;
  v. the presence or percentage of a tracer species or trace element in the fuel (e.g. a trace substance inherently present in the fuel which may vary between fuels and so be used to identify a fuel, and/or a substance added deliberately to act as a tracer);
  vi. the hydrogen to carbon ratio (H/C) of the fuel;
  vii. the hydrocarbon distribution of the fuel;
  viii. level of non-volatile particulate matter (nvPM) emissions on combustion (e.g. on combustion for a given combustor design, at a given operating condition);
  ix. naphthalene content of the fuel;
  x. sulphur content of the fuel;
  xi. cycloparaffin content of the fuel;
  xii. oxygen content of the fuel;
  xiii. thermal stability of the fuel (e.g. thermal breakdown temperature);
  xiv. level of coking of the fuel;
  xv. an indication that the fuel is a fossil fuel, for example fossil kerosene; and
  xvi. one or more properties such as density, viscosity, calorific value, and/or heat capacity.

The method may further comprise chemically or physically detecting one or more parameters of the resultant fuel in the fuel tank after refuelling, and verifying one or more of the calculated fuel characteristics based on the one or more detected parameters. The detected parameters may be fuel characteristics, or may be used to calculate or infer fuel characteristics—for example, the detected parameters may be shaft speed and mass flow rate of fuel, from which calorific value (a fuel characteristic) may be determined, or the detected parameters may be fuel density and/or the presence of a tracer, both of which are fuel characteristics.

The obtaining the one or more fuel characteristics of any fuel already present in the fuel tank prior to refuelling may comprise obtaining stored fuel characteristic data. The method may further comprise chemically or physically detecting one or more parameters of any fuel already present in the fuel tank prior to refuelling, and verifying the input to the calculating step based on the one or more detected parameters.

The method may further comprise chemically and/or physically determining one or more parameters of the fuel in the fuel tank, and using the determined values to replace the stored fuel characteristics for the fuel in the fuel tank.

The chemically and/or physically determining one or more parameters of the fuel in the fuel tank may be performed by extracting a sample of the fuel from the fuel tank for off-wing testing.

The chemically and/or physically determining one or more parameters of the fuel in the fuel tank and using the determined values to replace the stored fuel characteristics for the fuel in the fuel tank may be performed in response to a trigger event, such as:
  i. a threshold amount of time having elapsed since a previous chemical and/or physical determination of the one or more parameters of the fuel in the fuel tank;
  ii. a threshold number of refuelling events and/or flights having been reached since a previous determination of the one or more parameters of the fuel in the fuel tank; and/or
  iii. a discrepancy between one or more of the calculated characteristics and a detected parameter exceeding a threshold.

The method may further comprise controlling the propulsion system based on the calculated one or more fuel characteristics of the resultant fuel in the fuel tank after refuelling, for example as described below with respect to the fourth and fifth aspects.

The method may further comprise proposing or initiating a change to the flight profile based on the one or more fuel characteristics of the resultant fuel in the fuel tank after refuelling, for example as described below with respect to the sixth and seventh aspects.

According to a second aspect, there is provided a method of controlling the propulsion system of an aircraft, the propulsion system comprising a gas turbine engine and a fuel tank arranged to provide fuel to the gas turbine engine, the method comprising:
  obtaining one or more fuel characteristics of any fuel already present in the fuel tank prior to refuelling;
  determining one or more fuel characteristics of a fuel added to the fuel tank on refuelling;
  calculating one or more fuel characteristics of the resultant fuel in the fuel tank after refuelling;
  and controlling the propulsion system based on the calculated one or more fuel characteristics of the resultant fuel in the fuel tank after refuelling.

The obtaining one or more fuel characteristics of any fuel already present in the fuel tank prior to refuelling may comprise:
  (i) detecting one or more features of the composition of the fuel already present in the fuel tank; or
  (ii) obtaining the result of an earlier determination performed using the method of the first aspect.

According to a third aspect, there is provided a propulsion system for an aircraft comprising:
  a gas turbine engine, the gas turbine engine optionally comprising:
    an engine core comprising a turbine, a compressor, and a core shaft connecting the turbine to the compressor; and
    a fan located upstream of the engine core, the fan comprising a plurality of fan blades and being arranged to be driven by an output from the core shaft;
  a fuel tank arranged to contain a fuel to power the gas turbine engine; and
  a fuel composition tracker arranged to:
    store current fuel characteristic data, the fuel characteristic data comprising one or more fuel characteristics of fuel present in the fuel tank;
    obtain one or more fuel characteristics of a fuel added to the fuel tank on refuelling; and
    calculate updated values for the one or more fuel characteristics of the fuel in the fuel tank after refuelling.

The updated values may then take the place of the stored values, for use in future iterations of the steps performed by the fuel composition tracker.

The fuel characteristic data may be fuel composition data, including one or more parameters of a hydrocarbon distribution of the fuel.

According to a further aspect, there is provided a non-transitory computer readable medium having stored thereon instructions that, when executed by a processor, cause the processor to perform the method of the first and/or second aspects. The processor may be, or may be a part of, an Electronic Engine Controller of the aircraft.

According to a fourth aspect, there is provided a method of operating an aircraft comprising a gas turbine engine and a fuel tank arranged to provide fuel to the gas turbine engine, the method comprising:
  determining one or more fuel characteristics of the fuel arranged to be provided to the gas turbine engine; and
  proposing or initiating a change to a flight profile of the aircraft based on the one or more fuel characteristics.

Implementations of this aspect may therefore allow environmental benefits (e.g. reduced or tailored contrail formation) and/or operational benefits (e.g. improved fuel burn efficiency) to be obtained based on knowledge of the fuel being burned.

In some examples, the method may comprise automatically initiating the change to the flight profile based on the determined characteristics. In some examples, the method may comprise notifying a pilot of the suggested change to the flight profile based on the determined characteristics and allowing the pilot the opportunity to confirm or cancel the change. In some implementations, either example may be implemented depending on the nature of the change.

The one or more fuel characteristics of the fuel may comprise at least one of the fuel characteristics as listed above.

The change to the flight profile based on the fuel characteristics may comprise at least one of:
  (i) a change to the intended altitude; and
  (ii) a change to the intended route.

The determining one or more fuel characteristics of the fuel may comprise implementing the method of the first aspect, in particular by:
  obtaining one or more fuel characteristics of any fuel already present in the fuel tank prior to refuelling;
  determining one or more fuel characteristics of a fuel added to the fuel tank on refuelling; and
  calculating one or more fuel characteristics of the resultant fuel in the fuel tank after refuelling.

The method may further comprise receiving forecast weather conditions for an intended route of the aircraft. The received forecast weather conditions may be used to influence the changes in planned route and/or altitude.

The determining the one or more fuel characteristics may be performed based on detection of one or more fuel properties. The detection may be performed on-wing.

The determining the one or more fuel characteristics may be performed based on received fuel composition data, e.g. data sent electronically to the aircraft by a third party, or entered using a user interface onboard the aircraft. The fuel composition data may be provided to the aircraft on refuelling.

The one or more fuel characteristics may be determined for fuel in one or more fuel tanks of the aircraft.

One or more of the fuel characteristics, e.g. calorific value, may be inferred from performance of the gas turbine engine during at least one of engine warm-up, taxi, take-off and climb of the aircraft. The planned flight profile during cruise may be changed/the flight profile may be updated based on the one or more inferred fuel characteristics.

According to a fifth aspect, there is provided a propulsion system for an aircraft comprising:
  a gas turbine engine, the gas turbine engine optionally comprising:
    an engine core comprising a turbine, a compressor, and a core shaft connecting the turbine to the compressor; and
    a fan located upstream of the engine core, the fan comprising a plurality of fan blades and being arranged to be driven by an output from the core shaft;
  a fuel tank arranged to contain a fuel to power the gas turbine engine; and
  a fuel composition determination module arranged to:
    determine one or more fuel characteristics of the fuel arranged to be provided to the gas turbine engine; and
  a flight profile adjustor arranged to:
    propose or initiate a change to a flight profile of the aircraft based on the one or more fuel characteristics of the fuel.

The flight profile adjustor may be arranged to initiate or propose at least one of the following based on the fuel characteristics:
  (i) a change to the intended altitude; and
  (ii) a change to the intended route.

The propulsion system may be arranged to perform the method as described with respect to the fourth aspect.

According to a sixth aspect, there is provided a method of operating an aircraft comprising a propulsion system, the propulsion system comprising a gas turbine engine and a fuel tank arranged to provide fuel to the gas turbine engine, the method comprising:
  determining one or more fuel characteristics of the fuel arranged to be provided to the gas turbine engine; and
  controlling the propulsion system based on the one or more fuel characteristics.

Implementations of this aspect may therefore allow environmental benefits (e.g. reduced or tailored contrail formation) and/or operational benefits (e.g. improved fuel burn efficiency) to be obtained based on knowledge of the fuel being burned.

In some examples, the method may comprise controlling the propulsion system based on the determined characteristics, without seeking pilot input or approval. In some examples, the method may comprise notifying a pilot of the suggested change to the control of the propulsion system, based on the determined characteristics and allowing the pilot the opportunity to confirm or cancel the change. In some implementations, either example may be implemented depending on the nature of the change. The controlling may therefore be implemented directly, or after verification.

The method may be performed iteratively in flight, e.g. due to changes in fuel supplied to the gas turbine engine and/or changes in conditions and flight stage.

The one or more fuel characteristics of the fuel may comprise one or more of the characteristics listed above.

The method may further comprise receiving weather data relating to weather conditions around the aircraft or along a planned route of the aircraft. The received weather data may be used to influence the control of the propulsion system.

The method may further comprise detecting weather conditions around the aircraft in flight. The detected weather conditions may be used to influence the control of the propulsion system.

The control of the propulsion system based on the fuel characteristics may comprise making changes to one or more of the following in flight:
  An operating parameter of a heat management system of the aircraft (e.g. a fuel-oil heat exchanger) may be changed, or the temperature of fuel supplied to a combustor of the engine may be changed.
  When more than one fuel is stored aboard an aircraft, a selection of which fuel to use for which operations (e.g. for ground-based operations as opposed to flight, for low-temperature start-up, or for operations with different thrust demands) may be made based on fuel characteristics such as % Sustainable Aviation Fuel (SAF), non-volatile Particulate Matter (nvPM) generation potential, viscosity, and calorific value. A fuel delivery system may therefore be controlled appropriately based on the fuel characteristics.
  One or more flight control surfaces of the aircraft may be adjusted so as to change route and/or altitude based on knowledge of the fuel.
  The spill percentage of a fuel pump (i.e. the proportion of pumped fuel recirculated instead of being passed to the combustor) based on the % SAF of the fuel. The pump and/or one or more valves may therefore be controlled appropriately based on the fuel characteristics.
  Changes to the scheduling of variable-inlet guide vanes (VIGVs) may be made based on fuel characteristics. The VIGVs may therefore be moved, or a movement of the VIGVs be cancelled, as appropriate based on the fuel characteristics.

These options may be referred to as control examples, as they are examples of ways in which the propulsion system may be controlled based on fuel characteristics.

(The sustainable aviation fuel percentage (% SAF) of a fuel may be gravimetric or volumetric—it will be appreciated that there are often—generally small—differences in density between SAFs and traditional jet fuels such as Jet A.)

The determining the one or more fuel characteristics may be performed based on detection of one or more fuel properties. The detection may be performed on-wing.

The determining the one or more fuel characteristics may be performed based on received fuel composition data. The fuel composition data may be provided to the aircraft on refuelling.

The one or more fuel characteristics may be determined for fuel in one or more fuel tanks of the aircraft.

The one or more fuel characteristics may be determined for each of a plurality of fuels stored onboard the aircraft.

The one or more fuel characteristics may be determined for fuel immediately before entry into a combustor of the gas turbine engine. The determination of the one or more fuel characteristics of fuel immediately before entry into a combustor of the gas turbine engine may be performed a plurality of times during flight to account for changes in fuel composition.

The one or more of the fuel characteristics may be inferred from performance of the gas turbine engine during at least one of engine warm-up, taxi, take-off, and climb of the aircraft. The propulsion system may be controlled during cruise based on the one or more inferred fuel characteristics.

The determining the one or more fuel characteristics of the fuel may comprises implementing the method of the first aspect, in particular:

obtaining one or more fuel characteristics of any fuel already present in the fuel tank prior to refuelling;

determining one or more fuel characteristics of a fuel added to the fuel tank on refuelling; and calculating one or more fuel characteristics of the resultant fuel in the fuel tank after refuelling.

According to a seventh aspect, there is provided a propulsion system for an aircraft comprising:

a gas turbine engine, the gas turbine engine optionally comprising an engine core comprising a turbine, a compressor, and a core shaft connecting the turbine to the compressor; and a fan located upstream of the engine core, the fan comprising a plurality of fan blades and being arranged to be driven by an output from the core shaft;

a fuel tank arranged to contain a fuel to power the gas turbine engine;

a fuel composition determination module arranged to determine one or more fuel characteristics of the fuel arranged to be provided to the gas turbine engine; and a propulsion system controller arranged to control the propulsion system based on the one or more fuel characteristics of the fuel.

The fuel composition determination module may comprise a receiver arranged to receive data relating to fuel composition. The fuel composition determination module may be arranged to determine one or more fuel characteristics based on the received data.

The fuel composition determination module may comprise one or more sensors arranged to provide data relating to one or more fuel characteristics. The fuel composition determination module may be arranged to determine one or more fuel characteristics based on the sensor data.

The propulsion system may comprise a plurality of fuel tanks arranged to contain different fuels to power the gas turbine engine. The fuel composition determination module may be arranged to determine at least one fuel characteristic of each different fuel.

The propulsion system may be arranged to perform the method as described with respect to the sixth aspect.

According to an eighth aspect, there is provided a propulsion system for an aircraft comprising:

a gas turbine engine, the gas turbine engine optionally comprising:

an engine core comprising a turbine, a compressor, and a core shaft connecting the turbine to the compressor; and a fan located upstream of the engine core, the fan comprising a plurality of fan blades and being arranged to be driven by an output from the core shaft;

a plurality of fuel tanks, each arranged to contain a different fuel to be used to power the gas turbine engine, wherein the fuels have different calorific values; and a fuel manager arranged to store information on the fuel contained in each fuel tank and to control fuel input to the gas turbine engine in operation (optionally in flight only) by selection of a specific fuel or fuel combination from one or more of the plurality of fuel tanks based on thrust demand of the gas turbine engine such that a fuel with a lower calorific value is supplied to the gas turbine engine at lower thrust demand.

It will be appreciated that the propulsion system may comprise additional fuel tanks containing the same fuels in addition to a plurality of fuel tanks containing different fuels;

a minimum of two different fuels is provided onboard the aircraft for implementations of this aspect.

The variation in calorific value of the fuel corresponding to thrust demand may facilitate maintenance of a more constant fuel flow rate during at least one section of a flight (e.g. at cruise, or for a constant altitude section of cruise), and/or more even fuel pump and spill operation in flight during at least one section of a flight. Further, a lowest necessary fuel flow rate at key points (e.g. very low thrust points of operation) may be increased by moving to a lower calorific value fuel, so raising an overall minimum flow level and keeping flow within a narrower range across the entire flight envelope.

Implementations of this aspect may therefore allow a higher fuel mass flow rate to be maintained at lower thrust demand than if a fuel were not selected based on calorific value, so doing one or more of facilitating use of the fuel as a heat transfer fluid (provided that the lower calorific value fuel in question does not have a correspondingly lower heat capacity), improving lubrication, and/or reducing the chance of fuel overheating. This may be of particular utility when running at low idle thrust. Similarly, the use of a fuel with a higher calorific value at higher thrust demand may facilitate meeting that demand without stressing the fuel flow management system. Implementation of the present aspect may therefore mean that, when thrust demand is reduced, the fuel flow rate does not have to be reduced as far as it would otherwise have to be reduced.

Each fuel tank may be arranged to contain a fuel with a different type or proportion of a sustainable aviation fuel.

A first fuel tank of the plurality of fuel tanks may be arranged to contain only a fuel which is a sustainable aviation fuel. The sustainable aviation fuel in the first fuel tank may be selected such that the propulsion system can be run on that fuel alone.

The fuel manager may be arranged to implement different control for ground-based operations as compared to flight. For example, sustainable aviation fuel in the first fuel tank, or a high % SAF blend, may be used to power the aircraft when the aircraft is performing at least the majority of operations on the ground, irrespective of thrust demand or of calorific value of that fuel.

The fuel manager may be arranged such that all fuel used for ground operations is taken from the first fuel tank, and/or such that all fuel used for ground operations is SAF or the highest % SAF blend available to the aircraft.

The fuel manager may be arranged such that a fuel with a lower calorific value is supplied to the gas turbine engine at cruise than during climb.

The fuel manager may be arranged such that a fuel with a lower calorific value is supplied to the gas turbine engine at low idle than at high idle.

A first fuel tank of the plurality of fuel tanks may have a higher proportion of sustainable aviation fuel (e.g. 100%) than a second fuel tank of the plurality of fuel tanks. In some cases, more fuel from the second fuel tank may be used at cruise and more fuel from the first tank used at operating points with higher power demands. The higher % SAF fuel may have a higher calorific value.

First and second fuel tanks of the plurality of fuel tanks may contain sustainable aviation fuels of different compositions.

The fan may have a diameter of at least 330 cm.

According to a ninth aspect, there is provided a method of operating an aircraft comprising a gas turbine engine and a plurality of fuel tanks arranged to store fuel to power the gas turbine engine, the method comprising:

arranging each fuel tank of the plurality of fuel tanks to contain a different fuel to be used to power the gas turbine engine, wherein the fuels have different calorific values;

storing information on the fuel contained in each fuel tank; and controlling fuel input to the gas turbine engine in operation (optionally in flight only) by selection of a specific fuel or fuel combination from one or more of the plurality of fuel tanks based on thrust demand of the gas turbine engine such that a fuel with a lower calorific value is supplied to the gas turbine engine at lower thrust demand.

The arranging each fuel tank to contain a different fuel may comprise supplying each fuel tank with a different sustainable aviation fuel, and/or with a blended fuel with a different type or proportion of a sustainable aviation fuel.

The controlling fuel input to the gas turbine engine based on thrust demand may be performed only in flight. Fuel input may be differently controlled for ground-based operations.

According to a tenth aspect, there is provided a method of modifying an aircraft comprising a gas turbine engine and a plurality of fuel tanks arranged to store fuel to power the gas turbine engine, the method comprising:

arranging each fuel tank to contain a different fuel to be used to power the gas turbine engine, wherein the fuels have different calorific values; and providing a fuel manager arranged to store information on the fuel contained in each fuel tank and to control fuel input to the gas turbine engine in operation (optionally in flight only) by selection of a specific fuel or fuel combination from one or more of the plurality of fuel tanks based on thrust demand of the gas turbine engine such that a fuel with a lower calorific value is supplied to the gas turbine engine at lower thrust demand.

The arranging each fuel tank to contain a different fuel may comprise supplying each fuel tank with a different sustainable aviation fuel, and/or with a blended fuel with a different type or proportion of a sustainable aviation fuel.

The arranging each fuel tank to contain a different fuel may comprise adjusting at least one valve so as to fluidly isolate two or more fuel tanks from each other so as to provide separate containment for different fuels.

The fuel manager may be arranged to implement different control for ground-based operations as compared to flight. The control of fuel input to the gas turbine engine based on thrust demand may be performed only in flight. Fuel input may therefore be differently controlled for ground-based operations, e.g. selecting SAF (or a higher % SAF blend) irrespective of calorific value if the choice is between that and a fossil-based fuel (or a lower % SAF blend).

According to an eleventh aspect, there is provided a power system for an aircraft comprising:

a gas turbine engine arranged to burn a fuel so as to provide power to the aircraft;

a plurality of fuel tanks, each arranged to contain a fuel to be used to provide power to the aircraft, wherein at least two tanks of the plurality of fuel tanks contain different fuels, and wherein one or more tanks of the plurality of fuel tanks are arranged to contain only a fuel which is a sustainable aviation fuel; and a fuel manager arranged to store information on the fuel contained in each fuel tank and to control fuel supply so as to take only the sustainable aviation fuel to power at least the majority of operations on the ground.

In some examples, only sustainable aviation fuel may be used to power aircraft operations on the ground, such that all ground-based operations are powered using sustainable aviation fuel.

In other examples, most but not all of the fuel used for ground operations is sustainable aviation fuel, with only small amounts from other sources being used (e.g. less than 10% or less than 5% of the fuel use and/or of the operation time of ground-based operations).

In some examples, especially in examples wherein the sustainable aviation fuel has a higher viscosity at a given temperature than the fuel in another fuel tank, fuel from the another fuel tank may be used for start-up of the engine, and the fuel source may then be switched to the sustainable aviation fuel once the engine is running, e.g. once a certain temperature has been reached. The fuel in the tank used for start-up may be optimised for low-temperature initial use, and/or for other features of start-up operation. In such examples, sustainable aviation fuel may be used for all ground-based operations except for engine start-up if the fuel in the start-up tank is not also SAF, and SAF (optionally different SAFs) may be used for all ground-based operations if it is.

A gas turbine engine of the one or more gas turbine engines may be a gas turbine engine of an Auxiliary Power Unit—APU. The APU may be arranged to be active primarily or only during ground-based operations.

A first fuel tank of the one or more tanks may be arranged to contain a sustainable aviation fuel and may be exclusively dedicated to the APU such that the sustainable aviation fuel from the first fuel tank is not arranged to be provided to any other gas turbine engine of the aircraft. A fuel not certified for use to power flight may therefore be stored in the first fuel tank.

A first fuel tank of the one or more tanks may be arranged to contain a sustainable aviation fuel, and may be arranged to provide fuel to the APU when performing operations on the ground, and to serve as a trim tank in flight.

The APU may not be arranged to provide any propulsive power to the aircraft.

The gas turbine engine may be arranged to provide propulsive power to the aircraft, and may comprise:

an engine core comprising a turbine, a compressor, and a core shaft connecting the turbine to the compressor; and a fan located upstream of the engine core, the fan comprising a plurality of fan blades and being arranged to be driven by an output from the core shaft.

According to a twelfth aspect, there is a provided a propulsion system for an aircraft comprising:

a gas turbine engine, the gas turbine engine optionally comprising:

an engine core comprising a turbine, a compressor, and a core shaft connecting the turbine to the compressor; and a fan located upstream of the engine core, the fan comprising a plurality of fan blades and being arranged to be driven by an output from the core shaft;

a plurality of fuel tanks, each arranged to contain a fuel to be used to provide power to the aircraft, wherein at least two tanks of the plurality of fuel tanks contain different fuels, and wherein one or more tanks of the plurality of fuel tanks are arranged to contain only a fuel which is a sustainable aviation fuel; and a fuel manager arranged to store information on the fuel contained in each fuel tank and to control fuel input to the gas turbine engine so as to use only the sustainable aviation fuel when the aircraft is performing at least the majority of operations on the ground.

Each fuel tank may be arranged to contain a fuel with a different type of sustainable aviation fuel and/or a different proportion of a sustainable aviation fuel. In some implementations, two or more tanks may contain the same fuel.

The sustainable aviation fuel in at least a first fuel tank of the one or more tanks arranged to contain a sustainable aviation fuel may be selected such that the propulsion system can be run on that fuel alone.

The fuel manager may be arranged to control fuel input to the gas turbine engine in flight by selection of a specific fuel or fuel combination from one or more of the plurality of fuel tanks.

The fuel in the one or more tanks arranged to contain a sustainable aviation fuel for use in ground-based operations may have a lower calorific value than any fuel stored in another fuel tank of the plurality of fuel tanks. The fuel in the one or more tanks arranged to contain a sustainable aviation fuel for use in ground-based operations may give lower nvPM emissions than any fuel stored in another fuel tank of the plurality of fuel tanks. The fuel selected for use for ground-based operations may be optimised for ground-based operations, some or all of which may have a relatively low power demand as compared to average in-flight operation, and some or all of which may be required by regulations to meet more stringent emissions criteria.

A first fuel tank of the one or more tanks arranged to contain a sustainable aviation fuel may be smaller than the one or more other fuel tanks. The first fuel tank may be arranged to be used exclusively for ground-based operations of the aircraft. This arrangement may be as described with respect to the sixteenth to twentieth aspects, below. The fuel in the first fuel tank may be selected to have a lower calorific value than any fuel stored in another fuel tank of the plurality of fuel tanks.

The sustainable aviation fuel may be used to power all ground-based operations of the aircraft.

According to a thirteenth aspect, there is provided a method of operating an aircraft comprising a gas turbine engine and a plurality of fuel tanks arranged to store fuel to power the gas turbine engine, the method comprising:
  arranging at least two fuel tanks of the plurality of fuel tanks to store different fuels, wherein one or more tanks of the plurality of fuel tanks are arranged to contain only a fuel which is a sustainable aviation fuel;
  controlling fuel supply so as to use only the sustainable aviation fuel when the aircraft is performing at least the majority of operations on the ground.

The method may further comprise storing information on the fuel contained in each fuel tank. The control may be performed based on the stored information.

The gas turbine engine may be arranged to provide propulsive power to the aircraft, and may comprise:
  an engine core comprising a turbine, a compressor, and a core shaft connecting the turbine to the compressor; and
  a fan located upstream of the engine core, the fan comprising a plurality of fan blades and being arranged to be driven by an output from the core shaft.

The gas turbine engine may be a gas turbine engine of an Auxiliary Power Unit—APU—of the aircraft.

A first fuel tank of the one or more tanks arranged to contain a sustainable aviation fuel may be a trim tank of the aircraft. The sustainable aviation fuel in the first fuel tank may be arranged to be (at least substantially) used up performing the operations on the ground such that the first fuel tank is at least substantially empty and available to receive fuel pumped thereinto in flight.

According to a fourteenth aspect, there is provided a method of modifying an aircraft comprising a gas turbine engine and a plurality of fuel tanks arranged to store fuel to power the gas turbine engine, the method comprising:
  arranging at least two fuel tanks of the plurality of fuel tanks to each store a different fuel, wherein one or more tanks of the plurality of fuel tanks are arranged to contain only a fuel which is a sustainable aviation fuel; and
  providing a fuel manager arranged to control fuel supply so as to use only the sustainable aviation fuel when the aircraft is performing at least the majority of operations on the ground.

The fuel manager may be arranged to store information on the fuel contained in each fuel tank. The fuel manager may be arranged to perform the control of the fuel supply based on the stored information.

The gas turbine engine may be arranged to provide propulsive power to the aircraft, and may comprise:
  an engine core comprising a turbine, a compressor, and a core shaft connecting the turbine to the compressor; and
  a fan located upstream of the engine core, the fan comprising a plurality of fan blades and being arranged to be driven by an output from the core shaft.

The gas turbine engine may be a gas turbine engine of an Auxiliary Power Unit—APU—of the aircraft.

According to a fifteenth aspect, there is provided a power system for an aircraft comprising:
  an Auxiliary Power Unit—APU—comprising a gas turbine engine arranged to burn a fuel so as to provide power to the aircraft; and
  one or more fuel tanks arranged to contain only a fuel which is a sustainable aviation fuel;
  and wherein all fuel used by the APU is the sustainable aviation fuel.

According to a sixteenth aspect, there is provided a power system for an aircraft comprising:
  a gas turbine engine arranged to burn a fuel so as to provide power to the aircraft;
  one or more first fuel tanks arranged to be used to power ground-based operation of the aircraft;
  one or more secondary fuel tanks, each arranged to contain a fuel to be used to power the aircraft in flight; and
  a fuel manager arranged to control fuel supply so as to take fuel from only the one or more first fuel tanks to power at least the majority of ground-based operations.

Benefits may therefore be provided by filling the first fuel tank(s) with a fuel optimised for use in ground-based operations, e.g. for more efficient running of the engine, and/or for reduced emissions. Having one or more first fuel tanks arranged for, and optionally dedicated to, this purpose may facilitate refuelling and operation.

In some examples, only fuel from the first fuel tank(s) may be used to power aircraft operations on the ground, such that all ground-based operations are powered using fuel from the first fuel tank(s).

In other examples, most but not all of the fuel used for ground operations is taken from the first fuel tank, with only small amounts from other sources being used (e.g. less than 10% or less than 5% of the fuel use and/or of the operation time of ground-based operations).

In many examples, a single first fuel tank is provided. However, it will be appreciated that, whilst the discussion below often refers to a single first fuel tank, the disclosure is not limited in that way.

In some examples, especially in examples where the fuel in the first fuel tank has a higher viscosity at a given temperature than the fuel in another fuel tank, fuel from another fuel tank may be used for start-up of the engine, and the fuel source may then be switched to the first fuel tank once the engine is running, e.g. once a certain temperature has been reached. In such examples, fuel from the first fuel tank may be used for all ground-based operations except for engine start-up.

The fuel manager may be further arranged to take fuel only from the one or more secondary fuel tanks for at least the majority of other operations (e.g. climb and cruise). It will be appreciated that any remaining fuel in the first fuel tank may be finished off in flight (alone or as part of a blend); either in the early stages following ground-based operations, or thereafter.

The fuel manager may be arranged to take fuel from the one or more secondary fuel tanks for at least the majority of other operations.

The fuel manager may be arranged to take fuel from only the first fuel tank to power all ground-based operations.

A gas turbine engine of the one or more gas turbine engines may be a gas turbine engine of an Auxiliary Power Unit—APU. The APU may be arranged to be active only during ground-based operations.

The first fuel tank may be arranged to provide fuel to the APU when performing operations on the ground, and to serve as a trim tank in flight.

The APU may not be arranged to provide any propulsive power to the aircraft.

A gas turbine engine of the one or more gas turbine engines may be a gas turbine engine arranged to provide propulsive power to the aircraft. The gas turbine engine may comprise:
  an engine core comprising a turbine, a compressor, and a core shaft connecting the turbine to the compressor; and
  a fan located upstream of the engine core, the fan comprising a plurality of fan blades and being arranged to be driven by an output from the core shaft.

The fuel manager may be arranged to supply fuel only from the one or more secondary fuel tanks to the gas turbine engine in flight, such that the first fuel tank is not used to supply fuel to an engine in flight.

According to a seventeenth aspect, there is provided a propulsion system for an aircraft comprising:
  a gas turbine engine, the gas turbine engine optionally comprising:
    an engine core comprising a turbine, a compressor, and a core shaft connecting the turbine to the compressor; and
    a fan located upstream of the engine core, the fan comprising a plurality of fan blades and being arranged to be driven by an output from the core shaft;
  one or more first fuel tanks arranged to be used to power ground-based operation of the aircraft;
  one or more secondary fuel tanks, each arranged to contain a fuel to be used to power the gas turbine engine in flight; and
  a fuel manager arranged to control fuel input to the gas turbine engine so as to take fuel from only the one or more first fuel tanks to power at least the majority of ground-based operations.

The fuel manager may be further arranged to take fuel only from the one or more secondary fuel tanks for at least the majority of other operations (e.g. climb and cruise).

The first fuel tank may be arranged to contain only a fuel which is a sustainable aviation fuel.

In examples with only one first fuel tank, the first fuel tank may be smaller than the one or more secondary fuel tanks. In examples with multiple first fuel tanks, the total volume of the first fuel tanks may be less than the total volume of the secondary fuel tanks, and optionally smaller than the volume of each secondary fuel tank individually.

The propulsion system may comprise a plurality of secondary fuel tanks. The fuel manager may be arranged to be able to mix fuels from the secondary fuel tanks to power the gas turbine engine in flight, but may not be able to mix fuel from the first fuel tank with fuel from the secondary fuel tanks.

The fuel in the first fuel tank may have a lower calorific value and/or may generate lower levels of nvPM emissions than any fuel stored in the one or more secondary fuel tanks.

According to an eighteenth aspect, there is provided a method of operating an aircraft comprising:
  a gas turbine engine arranged to burn a fuel so as to provide power to the aircraft;
  one or more first fuel tanks arranged to be used to power ground-based operation of the aircraft; and
  one or more secondary fuel tanks, each arranged to contain a fuel to be used to power the aircraft in flight,
  the method comprising:
  controlling fuel supply so as to take fuel from only the one or more first fuel tanks when the aircraft to power at least the majority of ground-based operations.

The method may further comprise taking fuel from only the one or more secondary fuel tanks for at least the majority of other operations.

In some examples, only fuel from the one or more secondary fuel tanks may be used for other operations, such that the first fuel tank is exclusively used for ground-based operations.

The gas turbine engine may be arranged to provide propulsive power to the aircraft, and may comprise:
  an engine core comprising a turbine, a compressor, and a core shaft connecting the turbine to the compressor; and
  a fan located upstream of the engine core, the fan comprising a plurality of fan blades and being arranged to be driven by an output from the core shaft.

The gas turbine engine may be a gas turbine engine of an Auxiliary Power Unit—APU—of the aircraft.

The first fuel tank may be a trim tank of the aircraft. The fuel in the first fuel tank, which may be a sustainable aviation fuel, may be arranged to be used up performing the operations on the ground such that the first fuel tank is at last substantially empty and available to receive fuel pumped thereinto in flight.

According to a nineteenth aspect, there is provided a method of modifying an aircraft comprising one or more gas turbine engines and a plurality of fuel tanks, the method comprising:
  providing one or more first fuel tanks which are fluidly isolated from other (secondary) fuel tanks of the plurality of fuel tanks; and providing a fuel manager arranged to control fuel input to the one or more gas turbine engines so as to take fuel from only the one or more first fuel tanks to power at least the majority of ground-based operations.

The fuel manager may further be arranged to take fuel from only the one or more secondary fuel tanks for at least the majority of other operations.

The first fuel tank(s) may be permanently fluidly isolated from other fuel tanks, or may be reversibly isolatable from the other fuel tanks, e.g. by means of one or more pumps and/or valves.

In some examples, only fuel from the one or more secondary fuel tanks may be used for other operations, such that the first fuel tank is exclusively used for ground-based operations.

According to a twentieth aspect, there is provided a power system for an aircraft comprising:
  an Auxiliary Power Unit—APU—comprising a gas turbine engine arranged to burn a fuel so as to provide power to the aircraft; and
  one or more first fuel tanks which are fluidly isolated from any other fuel tanks of the power system;
  and wherein the one or more first fuel tanks are dedicated to the APU, such that all fuel used by the APU is taken from the one or more first fuel tanks (in normal operation).

It will be appreciated that an aircraft is generally arranged such that the APU can also be provided with fuel from one or more other tanks, for example in case the APU needs to start-up and operate in an emergency during flight, e.g. for non-propulsive purposes such as powering aircraft flight control surfaces after a main engine flame-out and/or providing power for restarting the main engines.

According to a twenty-first aspect, there is provided a power system for an aircraft comprising:
  a gas turbine engine arranged to burn a fuel in a combustor so as to provide power to the aircraft;
  a plurality of fuel tanks arranged to contain a different fuel to be used to provide power to the aircraft, wherein a first fuel tank of the plurality of fuel tanks is arranged to contain a first fuel, and a second tank of the plurality of fuel tanks is arranged to contain a second fuel with a different composition from the first fuel; and
  a fuel manager arranged to store information on the fuel contained in each fuel tank and to control fuel supply so as to take fuel from the second tank for engine start-up, before switching to the first fuel tank.

The second fuel may be selected for its improved start-up properties; for example having a lower viscosity at a given temperature than the fuel in the first fuel tank, so as to facilitate cold start of an engine.

The fuel selected for its improved start-up properties may have a lower viscosity at a given temperature than the fuel in the first tank.

The second fuel may be fossil-derived/petroleum-based.

The fuel manager may be arranged to control the fuel supply so as to switch from taking fuel from the second tank to taking fuel from the first fuel tank when at least one of the following conditions is met:
  (i) the fuel reaches a temperature of 60° C. at the inlet to the combustor;
  (ii) the gas turbine engine has been running for a period of 30 seconds; and
  (iii) the gas turbine engine has reached idle operation.

The first tank may be arranged to contain a sustainable aviation fuel.

The second tank may be arranged to contain a fossil-based hydrocarbon fuel.

The gas turbine engine may be a gas turbine engine of an Auxiliary Power Unit—APU. The APU may be arranged to be active only during ground-based operations, at least in normal operation.

The first fuel tank may be exclusively dedicated to the APU such that fuel from the first fuel tank is not arranged to be provided to any other gas turbine engine of the aircraft.

The first fuel tank may be arranged to provide fuel to the APU when performing operations on the ground, and to serve as a trim tank in flight.

The APU may be arranged not to provide any propulsive power to the aircraft.

Alternatively, the gas turbine engine may be arranged to provide propulsive power to the aircraft.

The gas turbine engine may comprise an engine core comprising a turbine, a compressor, and a core shaft connecting the turbine to the compressor; and a fan located upstream of the engine core, the fan comprising a plurality of fan blades and being arranged to be driven by an output from the core shaft.

The first fuel in the first fuel tank may be selected such that the gas turbine engine can be run on that fuel alone. The second fuel in the second fuel tank may be selected such that the gas turbine engine can be run on that fuel alone in flight, as well as for start-up.

Each fuel tank may be arranged to contain a fuel with a different type or proportion of a sustainable aviation fuel (SAF).

The fuel manager may be arranged to control fuel input to the gas turbine engine in flight by selection of a specific fuel or fuel combination from one or more of the plurality of fuel tanks.

The first fuel may be SAF or a high % SAF blend, and the fuel manager may be arranged to control the fuel supply so as to take fuel from the first fuel tank for the majority of ground-based operations—start-up may be the only exception.

According to a twenty-second aspect, there is provided a method of operating an aircraft comprising a gas turbine engine and a plurality of fuel tanks arranged to store fuel to power the gas turbine engine, the method comprising:
  arranging at least two of the fuel tanks to store a different fuel, wherein a first fuel tank of the plurality of fuel tanks is arranged to contain a first fuel, and a second tank of the plurality of fuel tanks is arranged to contain a second fuel with a different composition from the first fuel; and
  controlling fuel supply so as to take fuel from the second tank for engine start-up, before switching to the first fuel tank.

The method may further comprise storing information on the fuel contained in each fuel tank. The control may be performed based on the stored information.

The gas turbine engine may be arranged to provide propulsive power to the aircraft. The gas turbine engine may comprise an engine core comprising a turbine, a compressor, and a core shaft connecting the turbine to the compressor; and a fan located upstream of the engine core, the fan comprising a plurality of fan blades and being arranged to be driven by an output from the core shaft.

The first fuel tank may be a trim tank of the aircraft. The first fuel may be a sustainable aviation fuel (SAF) or a high % SAF blend and the fuel in the first fuel tank may be arranged to be used up performing operations on the ground (after start-up) such that the first fuel tank is at last substantially empty by the end of climb, if not on take-off, and available to receive fuel pumped thereinto in flight.

According to a twenty-third aspect, there is provided a method of modifying an aircraft comprising a gas turbine engine and a plurality of fuel tanks arranged to store fuel to power the gas turbine engine, the method comprising:

arranging a first fuel tank of the plurality of fuel tanks to contain a first fuel, and a second tank of the plurality of fuel tanks to contain a second fuel with a different composition from the first fuel; and providing a fuel manager arranged to control fuel supply so as to take fuel from the second tank for engine start-up, before switching to the first fuel tank.

The fuel manager may be additionally arranged to store information on the fuel contained in each fuel tank. The control may be performed based on the stored information.

The gas turbine engine may be arranged to provide propulsive power to the aircraft, and may comprise an engine core comprising a turbine, a compressor, and a core shaft connecting the turbine to the compressor; and a fan located upstream of the engine core, the fan comprising a plurality of fan blades and being arranged to be driven by an output from the core shaft.

The gas turbine engine may be a gas turbine engine of an Auxiliary Power Unit—APU—of the aircraft.

According to a twenty-fourth aspect, there is provided a method of operating an aircraft comprising a gas turbine engine and a plurality of fuel tanks arranged to provide fuel to the gas turbine engine, wherein at least two of the fuel tanks contain fuels with different fuel characteristics, the method being performed by processing circuitry and comprising:

obtaining a flight profile for a flight of the aircraft; and determining a fuelling schedule for the flight based on the flight profile and the fuel characteristics, the fuelling schedule governing/dictating the variation with time of how much fuel is drawn from each tank.

The fuelling schedule lists an intended variation with time of how much fuel is drawn from each tank and is intended to be used to instruct a fuelling manager to supply fuel to the gas turbine engine accordingly. The fuelling schedule can therefore be described as governing, dictating or directing fuel use for the flight (optionally for the aircraft in flight only, or also for ground-based operations).

The method may be performed on-wing, e.g. by a fuelling schedule determination module of the aircraft, which may form a part of an electronic engine controller (EEC) of the aircraft. Alternatively, the method may be performed off-wing, and the fuelling schedule provided to the aircraft for implementation.

The fuel characteristics of the fuel comprise at least one of:
i. percentage of sustainable aviation fuel in the fuel;
ii. aromatic hydrocarbon content of the fuel;
iii. multi-aromatic hydrocarbon content of the fuel;
iv. percentage of nitrogen-containing species in the fuel;
v. presence or percentage of a tracer species or trace element in the fuel;
vi. hydrogen to carbon ratio of the fuel;
vii. hydrocarbon distribution of the fuel;
viii. level of non-volatile particulate matter emissions on combustion;
ix. naphthalene content of the fuel;
x. sulphur content of the fuel;
xi. cycloparaffin content of the fuel;
xii. oxygen content of the fuel;
xiii. thermal stability of the fuel;
xiv. level of coking of the fuel;
xv. an indication that the fuel is a fossil fuel; and
xvi. at least one of density, viscosity, calorific value, and heat capacity.

The fuelling schedule may be determined using information from the flight profile including at least one of:
(i) intended altitude; and
(ii) intended route.

The method may further comprise receiving forecast weather conditions for an intended route of the aircraft defined in the flight profile, and the received forecast weather conditions may be used to influence the fuelling schedule.

The determining the fuelling schedule may comprise determining how much sustainable aviation fuel—SAF—is available to the aircraft, and/or which tanks contain SAF or a high % SAF blend, and preferentially scheduling the use of SAF (alone or as part of a blend) for ground-based operations of the aircraft.

The determining the fuelling schedule may comprise determining a calorific value of each fuel onboard the aircraft, and preferentially scheduling the use of a lower calorific value fuel for periods of lower thrust demand.

The method may further comprise controlling fuel input to the gas turbine engine in operation in accordance with the fuelling schedule.

The obtaining and determining steps may be performed off-wing. The method may further comprise providing the fuelling schedule to the aircraft prior to the controlling step.

According to a twenty-fifth aspect, there is provided a propulsion system for an aircraft comprising:

a gas turbine engine, the gas turbine engine optionally comprising:
an engine core comprising a turbine, a compressor, and a core shaft connecting the turbine to the compressor; and
a fan located upstream of the engine core, the fan comprising a plurality of fan blades and being arranged to be driven by an output from the core shaft;

a plurality of fuel tanks arranged to contain fuel to power the gas turbine engine, wherein at least two of the fuel tanks contain fuels with different fuel characteristics; and a fuelling schedule determination module arranged to:
obtain a flight profile for a flight of the aircraft; and
determine a fuelling schedule for the flight based on the flight profile and the fuel characteristics, the fuelling schedule governing the variation with time of how much fuel is drawn from each tank during the flight.

The fuel characteristics of the fuel may comprise one or more of the fuel characteristics listed above for the twenty-fourth aspect.

The fuelling schedule determination module may be arranged to determine the fuelling schedule using information from the flight profile including at least one of:
(i) intended altitude; and
(ii) intended route.

The propulsion system may further comprise a receiver arranged to receive data concerning forecast weather conditions for an intended route of the aircraft, the route being defined in the flight profile. The received forecast weather conditions may be used to influence the fuelling schedule.

The fuelling schedule determination module may be arranged to determine the fuelling schedule based on determining how much sustainable aviation fuel—SAF—is available to the aircraft, and to preferentially schedule the use of SAF for ground-based operations of the aircraft.

The fuelling schedule determination module may be arranged to determine the fuelling schedule based on determining a calorific value of each fuel onboard the aircraft, and to preferentially schedule the use of a lower calorific value fuel for periods of lower thrust demand.

The fuelling schedule determination module may be arranged to control fuel input to the gas turbine engine in operation in accordance with the fuelling schedule.

According to a twenty-sixth aspect, there is provided a non-transitory computer readable medium having stored thereon instructions that, when executed by a processor, cause the processor to:

determine a fuelling schedule for a flight of an aircraft, the aircraft comprising a gas turbine engine and a plurality of fuel tanks arranged to provide fuel to the gas turbine engine, wherein at least two of the fuel tanks contain fuels with different fuel characteristics. The fuelling schedule is determined based on a flight profile for the flight of the aircraft and the fuel characteristics of the fuels available to the aircraft. The fuelling schedule lists/directs the variation with time of how much fuel is drawn from each tank over the course of the flight.

The instructions may be further arranged to cause the processor to control fuel input to the gas turbine engine in operation in accordance with the fuelling schedule. The processor may comprise or consist of an onboard fuelling schedule determination module, and may be or may be a part of an Electronic Engine Controller.

The instructions may be further arranged to cause the processor to provide the fuelling schedule to the aircraft for implementation. The processor may comprise or consist of an off-wing fuelling schedule determination module.

According to a twenty-seventh aspect, there is provided a power system for an aircraft comprising:

one or more gas turbine engines arranged to burn a fuel so as to provide power to the aircraft;

a plurality of fuel tanks each arranged to contain a fuel to be used to provide power to the aircraft, wherein at least two tanks of the plurality of fuel tanks contain different fuels, the different fuels each having a different proportion of a sustainable aviation fuel; and a fuel manager arranged to:
store information on the fuel contained in each fuel tank;
identify which tank contains the fuel with the highest proportion of a sustainable aviation fuel; and
control fuel supply so as to take fuel only from the tank containing the fuel with the highest proportion of a sustainable aviation fuel to power at least the majority of operations on the ground.

The different proportion of a sustainable aviation fuel (SAF) may be from 0% SAF to 100% SAF. The fuel with the highest proportion of a sustainable aviation fuel may be greater than 50% SAF.

A gas turbine engine of the one or more gas turbine engines may be a gas turbine engine of an Auxiliary Power Unit—APU.

A first fuel tank of the plurality of fuel tanks may be arranged to contain the fuel with the highest proportion of a sustainable aviation fuel, and optionally the fuel may be a sustainable aviation fuel (i.e. a fuel for which the proportion of SAF is 100%). The first fuel tank may be exclusively dedicated to the APU such that the fuel from the first fuel tank is not arranged to be provided to any other gas turbine engine of the aircraft.

If a plurality of fuel tanks contain a fuel having the same highest proportion of a sustainable aviation fuel, which tank to use may be selected based on comparing at least one of:
(i) levels of non-volatile particulate matter emissions on combustion of the fuels; and
(ii) hydrogen to carbon ratios of the fuels.

One or more other parameters relating to air quality may also be compared so as to select the fuel likely to provide the best air quality outcomes. Environmental factors (e.g. airport altitude and humidity) may also be considered in this assessment.

The power system may be a propulsion system of the aircraft, and the gas turbine engine (at least one gas turbine engine of the one or more gas turbine engines) may be arranged to provide propulsive power to the aircraft.

The fuel with the highest proportion of a sustainable aviation fuel may be selected such that the propulsion system can be run on that fuel alone.

The fuel with the highest proportion of a sustainable aviation fuel—SAF—may contain more than 50% SAF, and optionally may contain at least 55% SAF.

The fuel manager may be arranged to control fuel input to the gas turbine engine in flight by selection of a specific fuel or fuel combination from one or more of the plurality of fuel tanks.

A first fuel tank of the plurality of fuel tanks may be arranged to contain the fuel with the highest proportion of a sustainable aviation fuel, and may be smaller than the one or more other fuel tanks. The first fuel tank may be arranged to be used exclusively for ground-based operations of the aircraft.

The fuel with the highest proportion of a sustainable aviation fuel, for use in ground-based operations, may have a lower calorific value than any fuel stored in another fuel tank of the plurality of fuel tanks.

The fuel with the highest proportion of a sustainable aviation fuel may be used to power all ground-based operations of the aircraft.

A first fuel tank of the plurality of fuel tanks may be arranged to contain the fuel with the highest proportion of a sustainable aviation fuel and may be arranged to provide fuel to the gas turbine engine when performing operations on the ground, and to serve as a trim tank in flight.

The fuel with the highest proportion of a sustainable aviation fuel—SAF—may be 100% SAF.

According to a twenty-eighth aspect, there is provided a power system for an aircraft comprising:

a gas turbine engine arranged to burn a fuel so as to provide power to the aircraft;

a plurality of fuel tanks each arranged to contain a fuel to be used to provide power to the aircraft, wherein at least two tanks of the plurality of fuel tanks contain different fuels, a first tank containing a fuel which is more than 50% sustainable aviation fuel and a second tank containing a fuel which is less than 50% sustainable aviation fuel; and a fuel manager arranged to:
store information on the fuel contained in each fuel tank; and
control fuel supply so as to only use fuel which is more than 50% a sustainable aviation fuel to power at least the majority of operations on the ground.

The first tank may contain a fuel which is a sustainable aviation fuel (i.e. 100% SAF).

According to a twenty-ninth aspect, there is provided a method of operating an aircraft comprising a gas turbine engine and a plurality of fuel tanks arranged to store fuel to power the gas turbine engine, the method comprising:

arranging two or more fuel tanks of the plurality of fuel tanks to store different fuels, the different fuels each having a different proportion of a sustainable aviation fuel;

identifying which tank contains the fuel with the highest proportion of a sustainable aviation fuel; and controlling fuel supply so as to take fuel only from the tank containing the fuel with the highest proportion of a sustainable aviation fuel when the aircraft is performing at least the majority of operations on the ground.

The method may further comprise storing information on the fuel contained in each fuel tank. The control may be performed based on the stored information.

The gas turbine engine may be arranged to provide propulsive power to the aircraft.

The gas turbine engine may be a gas turbine engine of an Auxiliary Power Unit—APU—of the aircraft.

A first fuel tank of the one or more tanks may be arranged to contain the fuel with the highest proportion of a sustainable aviation fuel. This first fuel tank may be arranged to function as a trim tank of the aircraft—the fuel in the first fuel tank may therefore be arranged to be (at least substantially) used up performing the operations on the ground such that the first fuel tank is at last substantially empty and available to receive fuel pumped thereinto in flight.

According to a thirtieth aspect, there is provided a method of modifying an aircraft comprising a gas turbine engine and a plurality of fuel tanks arranged to store fuel to power the gas turbine engine, the method comprising:

arranging two or more fuel tanks of the plurality of fuel tanks to store different fuels, the different fuels each having a different proportion of a sustainable aviation fuel; and providing a fuel manager arranged to:

identify which tank contains the fuel with the highest proportion of a sustainable aviation fuel; and control fuel supply so as to take fuel only from the tank containing the fuel with the highest proportion of a sustainable aviation fuel when the aircraft is performing at least the majority of operations on the ground.

The fuel manager may be arranged to store information on the fuel contained in each fuel tank. The fuel manager may be arranged to perform the tank identification and control of the fuel supply based on the stored information.

As noted elsewhere herein, the present disclosure may relate to a gas turbine engine. Such a gas turbine engine may comprise an engine core comprising a turbine, a combustor, a compressor, and a core shaft connecting the turbine to the compressor. Such a gas turbine engine may comprise a fan (having fan blades) located upstream of the engine core. Alternatively, in some examples, the gas turbine engine may comprise a fan located downstream of the engine core. Thus, the gas turbine engine may be an open rotor or a turboprop engine.

Where the gas turbine engine is an open rotor or a turboprop engine, the gas turbine engine may comprise two contra-rotating propeller stages attached to and driven by a free power turbine via a shaft. The propellers may rotate in opposite senses so that one rotates clockwise and the other anti-clockwise around the engine's rotational axis. Alternatively, the gas turbine engine may comprise a propeller stage and a guide vane stage configured downstream of the propeller stage. The guide vane stage may be of variable pitch. Accordingly, high-pressure, intermediate pressure, and free power turbines respectively may drive high and intermediate pressure compressors and propellers by suitable interconnecting shafts. Thus, the propellers may provide the majority of the propulsive thrust.

Where the gas turbine engine is an open rotor or a turboprop engine, one or more of the propeller stages may be driven by a gearbox of the type described.

Arrangements of the present disclosure may be particularly, although not exclusively, beneficial for fans that are driven via a gearbox. Accordingly, the gas turbine engine may comprise a gearbox that receives an input from the core shaft and outputs drive to the fan so as to drive the fan at a lower rotational speed than the core shaft. The input to the gearbox may be directly from the core shaft, or indirectly from the core shaft, for example via a spur shaft and/or gear. The core shaft may rigidly connect the turbine and the compressor, such that the turbine and compressor rotate at the same speed (with the fan rotating at a lower speed).

The gas turbine engine as described and/or claimed herein may have any suitable general architecture. For example, the gas turbine engine may have any desired number of shafts that connect turbines and compressors, for example one, two or three shafts. Purely by way of example, the turbine connected to the core shaft may be a first turbine, the compressor connected to the core shaft may be a first compressor, and the core shaft may be a first core shaft. The engine core may further comprise a second turbine, a second compressor, and a second core shaft connecting the second turbine to the second compressor. The second turbine, second compressor, and second core shaft may be arranged to rotate at a higher rotational speed than the first core shaft.

In such an arrangement, the second compressor may be positioned axially downstream of the first compressor. The second compressor may be arranged to receive (for example directly receive, for example via a generally annular duct) flow from the first compressor.

The gearbox may be arranged to be driven by the core shaft that is configured to rotate (for example in use) at the lowest rotational speed (for example the first core shaft in the example above). For example, the gearbox may be arranged to be driven only by the core shaft that is configured to rotate (for example in use) at the lowest rotational speed (for example only be the first core shaft, and not the second core shaft, in the example above). Alternatively, the gearbox may be arranged to be driven by any one or more shafts, for example the first and/or second shafts in the example above.

The gearbox may be a reduction gearbox (in that the output to the fan is a lower rotational rate than the input from the core shaft). Any type of gearbox may be used. For example, the gearbox may be a "planetary" or "star" gearbox, as described in more detail elsewhere herein. The gearbox may have any desired reduction ratio (defined as the rotational speed of the input shaft divided by the rotational speed of the output shaft), for example greater than 2.5, for example in the range of from 3 to 4.2, or 3.2 to 3.8, for example on the order of or at least 3, 3.1, 3.2, 3.3, 3.4, 3.5, 3.6, 3.7, 3.8, 3.9, 4, 4.1 or 4.2. The gear ratio may be, for example, between any two of the values in the previous sentence. Purely by way of example, the gearbox may be a "star" gearbox having a ratio in the range of from 3.1 or 3.2 to 3.8. In some arrangements, the gear ratio may be outside these ranges.

In any gas turbine engine as described and/or claimed herein, fuel of a given composition or blend is provided to a combustor, which may be provided axially downstream of the fan and compressor(s). For example, the combustor may be directly downstream of (for example at the exit of) the second compressor, where a second compressor is provided. By way of further example, the flow at the exit to the combustor may be provided to the inlet of the second turbine, where a second turbine is provided. The combustor may be provided upstream of the turbine(s).

The or each compressor (for example the first compressor and second compressor as described above) may comprise any number of stages, for example multiple stages. Each stage may comprise a row of rotor blades and a row of stator vanes, which may be variable stator vanes (in that their angle of incidence may be variable). The row of rotor blades and the row of stator vanes may be axially offset from each other.

The or each turbine (for example the first turbine and second turbine as described above) may comprise any number of stages, for example multiple stages. Each stage may comprise a row of rotor blades and a row of stator vanes. The row of rotor blades and the row of stator vanes may be axially offset from each other.

Each fan blade may be defined as having a radial span extending from a root (or hub) at a radially inner gas-washed location, or 0% span position, to a tip at a 100% span position. The ratio of the radius of the fan blade at the hub to the radius of the fan blade at the tip may be less than (or on the order of) any of: 0.4, 0.39, 0.38, 0.37, 0.36, 0.35, 0.34, 0.33, 0.32, 0.31, 0.3, 0.29, 0.28, 0.27, 0.26, or 0.25. The ratio of the radius of the fan blade at the hub to the radius of the fan blade at the tip may be in an inclusive range bounded by any two of the values in the previous sentence (i.e. the values may form upper or lower bounds), for example in the range of from 0.28 to 0.32. These ratios may commonly be referred to as the hub-to-tip ratio. The radius at the hub and the radius at the tip may both be measured at the leading edge (or axially forwardmost) part of the blade. The hub-to-tip ratio refers, of course, to the gas-washed portion of the fan blade, i.e. the portion radially outside any platform.

The radius of the fan may be measured between the engine centreline and the tip of a fan blade at its leading edge. The fan diameter (which may simply be twice the radius of the fan) may be greater than (or on the order of) any of: 220 cm, 230 cm, 240 cm, 250 cm (around 100 inches), 260 cm, 270 cm (around 105 inches), 280 cm (around 110 inches), 290 cm (around 115 inches), 300 cm (around 120 inches), 310 cm, 320 cm (around 125 inches), 330 cm (around 130 inches), 340 cm (around 135 inches), 350 cm, 360 cm (around 140 inches), 370 cm (around 145 inches), 380 (around 150 inches) cm, 390 cm (around 155 inches), 400 cm, 410 cm (around 160 inches) or 420 cm (around 165 inches). The fan diameter may be in an inclusive range bounded by any two of the values in the previous sentence (i.e. the values may form upper or lower bounds), for example in the range of from 240 cm to 280 cm or 330 cm to 380 cm.

The rotational speed of the fan may vary in use. Generally, the rotational speed is lower for fans with a higher diameter. Purely by way of non-limitative example, the rotational speed of the fan at cruise conditions may be less than 2500 rpm, for example less than 2300 rpm. Purely by way of further non-limitative example, the rotational speed of the fan at cruise conditions for an engine having a fan diameter in the range of from 220 cm to 300 cm (for example 240 cm to 280 cm or 250 cm to 270 cm) may be in the range of from 1700 rpm to 2500 rpm, for example in the range of from 1800 rpm to 2300 rpm, for example in the range of from 1900 rpm to 2100 rpm. Purely by way of further non-limitative example, the rotational speed of the fan at cruise conditions for an engine having a fan diameter in the range of from 330 cm to 380 cm may be in the range of from 1200 rpm to 2000 rpm, for example in the range of from 1300 rpm to 1800 rpm, for example in the range of from 1400 rpm to 1800 rpm.

In use of the gas turbine engine, the fan (with associated fan blades) rotates about a rotational axis. This rotation results in the tip of the fan blade moving with a velocity $U_{tip}$. The work done by the fan blades 13 on the flow results in an enthalpy rise dH of the flow. A fan tip loading may be defined as $dH/U_{tip}^2$, where dH is the enthalpy rise (for example the 1-D average enthalpy rise) across the fan and $U_{tip}$ is the (translational) velocity of the fan tip, for example at the leading edge of the tip (which may be defined as fan tip radius at leading edge multiplied by angular speed). The fan tip loading at cruise conditions may be greater than (or on the order of) any of: 0.28, 0.29, 0.30, 0.31, 0.32, 0.33, 0.34, 0.35, 0.36, 0.37, 0.38, 0.39 or 0.4 (all values being dimensionless). The fan tip loading may be in an inclusive range bounded by any two of the values in the previous sentence (i.e. the values may form upper or lower bounds), for example in the range of from 0.28 to 0.31, or 0.29 to 0.3.

Gas turbine engines in accordance with the present disclosure may have any desired bypass ratio, where the bypass ratio is defined as the ratio of the mass flow rate of the flow through the bypass duct to the mass flow rate of the flow through the core at cruise conditions. In some arrangements the bypass ratio may be greater than (or on the order of) any of the following: 10, 10.5, 11, 11.5, 12, 12.5, 13, 13.5, 14, 14.5, 15, 15.5, 16, 16.5, 17, 17.5, 18, 18.5, 19, 19.5 or 20. The bypass ratio may be in an inclusive range bounded by any two of the values in the previous sentence (i.e. the values may form upper or lower bounds), for example in the range of form 12 to 16, 13 to 15, or 13 to 14. The bypass duct may be substantially annular. The bypass duct may be radially outside the core engine. The radially outer surface of the bypass duct may be defined by a nacelle and/or a fan case.

The overall pressure ratio of a gas turbine engine as described and/or claimed herein may be defined as the ratio of the stagnation pressure upstream of the fan to the stagnation pressure at the exit of the highest pressure compressor (before entry into the combustor). By way of non-limitative example, the overall pressure ratio of a gas turbine engine as described and/or claimed herein at cruise may be greater than (or on the order of) any of the following: 35, 40, 45, 50, 55, 60, 65, 70, 75. The overall pressure ratio may be in an inclusive range bounded by any two of the values in the previous sentence (i.e. the values may form upper or lower bounds), for example in the range of from 50 to 70.

Specific thrust of an engine may be defined as the net thrust of the engine divided by the total mass flow through the engine. In some examples, specific thrust may depend, for a given thrust condition, upon the specific composition of fuel provided to the combustor. At cruise conditions, the specific thrust of an engine described and/or claimed herein may be less than (or on the order of) any of the following: 110 $Nkg^{-1}$ s, 105 $Nkg^{-1}$ s, 100 $Nkg^{-1}$ s, 95 $Nkg^{-1}$ s, 90 $Nkg^{-1}$ s, 85 $Nkg^{-1}$ s or 80 $Nkg^{-1}$ s. The specific thrust may be in an inclusive range bounded by any two of the values in the previous sentence (i.e. the values may form upper or lower bounds), for example in the range of from 80 $Nkg^{-1}$ s to 100 $Nkg^{-1}$ s, or 85 $Nkg^{-1}$ s to 95 $Nkg^{-1}$ s. Such engines may be particularly efficient in comparison with conventional gas turbine engines.

A gas turbine engine as described and/or claimed herein may have any desired maximum thrust. Purely by way of non-limitative example, a gas turbine as described and/or claimed herein may be capable of producing a maximum thrust of at least (or on the order of) any of the following: 160 kN, 170 kN, 180 kN, 190 kN, 200 kN, 250 kN, 300 kN, 350 kN, 400 kN, 450 kN, 500 kN, or 550 kN. The maximum thrust may be in an inclusive range bounded by any two of the values in the previous sentence (i.e. the values may form upper or lower bounds). Purely by way of example, a gas turbine as described and/or claimed herein may be capable of producing a maximum thrust in the range of from 330 kN to 420 kN, for example 350 kN to 400 kN. The thrust referred to above may be the maximum net thrust at standard atmospheric conditions at sea level plus 15 degrees C. (ambient pressure 101.3 kPa, temperature 30 degrees C.), with the engine static.

In use, the temperature of the flow at the entry to the high pressure turbine may be particularly high. This temperature, which may be referred to as TET, may be measured at the exit to the combustor, for example immediately upstream of the first turbine vane, which itself may be referred to as a nozzle guide vane. In some examples, TET may depend, for a given thrust condition, upon the specific composition of fuel provided to the combustor. At cruise, the TET may be at least (or on the order of) any of the following: 1400K, 1450K, 1500K, 1550K, 1600K or 1650K. The TET at cruise may be in an inclusive range bounded by any two of the values in the previous sentence (i.e. the values may form upper or lower bounds). The maximum TET in use of the engine may be, for example, at least (or on the order of) any of the following: 1700K, 1750K, 1800K, 1850K, 1900K, 1950K or 2000K. The maximum TET may be in an inclusive range bounded by any two of the values in the previous sentence (i.e. the values may form upper or lower bounds), for example in the range of from 1800K to 1950K. The maximum TET may occur, for example, at a high thrust condition, for example at a maximum take-off (MTO) condition.

A fan blade and/or aerofoil portion of a fan blade described and/or claimed herein may be manufactured from any suitable material or combination of materials. For example at least a part of the fan blade and/or aerofoil may be manufactured at least in part from a composite, for example a metal matrix composite and/or an organic matrix composite, such as carbon fibre. By way of further example at least a part of the fan blade and/or aerofoil may be manufactured at least in part from a metal, such as a titanium based metal or an aluminium based material (such as an aluminium-lithium alloy) or a steel based material. The fan blade may comprise at least two regions manufactured using different materials. For example, the fan blade may have a protective leading edge, which may be manufactured using a material that is better able to resist impact (for example from birds, ice or other material) than the rest of the blade. Such a leading edge may, for example, be manufactured using titanium or a titanium-based alloy. Thus, purely by way of example, the fan blade may have a carbon-fibre or aluminium based body (such as an aluminium lithium alloy) with a titanium leading edge.

A fan as described and/or claimed herein may comprise a central portion, from which the fan blades may extend, for example in a radial direction. The fan blades may be attached to the central portion in any desired manner. For example, each fan blade may comprise a fixture which may engage a corresponding slot in the hub (or disc). Purely by way of example, such a fixture may be in the form of a dovetail that may slot into and/or engage a corresponding slot in the hub/disc in order to fix the fan blade to the hub/disc. By way of further example, the fan blades maybe formed integrally with a central portion. Such an arrangement may be referred to as a bladed disc or a bladed ring. Any suitable method may be used to manufacture such a bladed disc or bladed ring. For example, at least a part of the fan blades may be machined from a block and/or at least part of the fan blades may be attached to the hub/disc by welding, such as linear friction welding.

The gas turbine engines described and/or claimed herein may or may not be provided with a variable area nozzle (VAN). Such a variable area nozzle may allow the exit area of the bypass duct to be varied in use. The general principles of the present disclosure may apply to engines with or without a VAN.

The fan of a gas turbine as described and/or claimed herein may have any desired number of fan blades, for example 14, 16, 18, 20, 22, 24 or 26 fan blades.

As used herein, the terms idle, taxi, take-off, climb, cruise, descent, approach, and landing have the conventional meaning and would be readily understood by the skilled person. Thus, for a given gas turbine engine for an aircraft, the skilled person would immediately recognise each term to refer to an operating phase of the engine within a given mission of an aircraft to which the gas turbine engine is designed to be attached.

In this regard, ground idle may refer to an operating phase of the engine where the aircraft is stationary and in contact with the ground, but where there is a requirement for the engine to be running. During idle, the engine may be producing between 3% and 9% of the available thrust of the engine. In further examples, the engine may be producing between 5% and 8% of available thrust. In yet further examples, the engine may be producing between 6% and 7% of available thrust. Taxi may refer to an operating phase of the engine where the aircraft is being propelled along the ground by the thrust produced by the engine. During taxi, the engine may be producing between 5% and 15% of available thrust. In further examples, the engine may be producing between 6% and 12% of available thrust. In yet further examples, the engine may be producing between 7% and 10% of available thrust. Take-off may refer to an operating phase of the engine where the aircraft is being propelled by the thrust produced by the engine. At an initial stage within the take-off phase, the aircraft may be propelled whilst the aircraft is in contact with the ground. At a later stage within the take-off phase, the aircraft may be propelled whilst the aircraft is not in contact with the ground. During take-off, the engine may be producing between 90% and 100% of available thrust. In further examples, the engine may be producing between 95% and 100% of available thrust. In yet further examples, the engine may be producing 100% of available thrust.

Climb may refer to an operating phase of the engine where the aircraft is being propelled by the thrust produced by the engine. During climb, the engine may be producing between 75% and 100% of available thrust. In further examples, the engine may be producing between 80% and 95% of available thrust. In yet further examples, the engine may be producing between 85% and 90% of available thrust. In this regard, climb may refer to an operating phase within an aircraft flight cycle between take-off and the arrival at cruise conditions. Additionally or alternatively, climb may refer to a nominal point in an aircraft flight cycle between take-off and landing, where a relative increase in altitude is required, which may require an additional thrust demand of the engine.

As used herein, cruise conditions have the conventional meaning and would be readily understood by the skilled person. Thus, for a given gas turbine engine for an aircraft, the skilled person would immediately recognise cruise conditions to mean the operating point of the engine at mid-cruise of a given mission (which may be referred to in the industry as the "economic mission") of an aircraft to which the gas turbine engine is designed to be attached. In this regard, mid-cruise is the point in an aircraft flight cycle at which 50% of the total fuel that is burned between top of climb and start of descent has been burned (which may be approximated by the midpoint—in terms of time and/or distance—between top of climb and start of descent. Cruise conditions thus define an operating point of, the gas turbine engine that provides a thrust that would ensure steady state operation (i.e. maintaining a constant altitude and constant Mach Number) at mid-cruise of an aircraft to which it is designed to be attached, taking into account the number of engines provided to that aircraft. For example where an engine is designed to be attached to an aircraft that has two engines of the same type, at cruise conditions the engine provides half of the total thrust that would be required for steady state operation of that aircraft at mid-cruise.

In other words, for a given gas turbine engine for an aircraft, cruise conditions are defined as the operating point of the engine that provides a specified thrust (required to provide—in combination with any other engines on the aircraft—steady state operation of the aircraft to which it is designed to be attached at a given mid-cruise Mach Number) at the mid-cruise atmospheric conditions (defined by the International Standard Atmosphere according to ISO 2533 at the mid-cruise altitude). For any given gas turbine engine for an aircraft, the mid-cruise thrust, atmospheric conditions and Mach Number are known, and thus the operating point of the engine at cruise conditions is clearly defined.

Purely by way of example, the forward speed at the cruise condition may be any point in the range of from Mach 0.7 to 0.9, for example 0.75 to 0.85, for example 0.76 to 0.84, for example 0.77 to 0.83, for example 0.78 to 0.82, for example 0.79 to 0.81, for example on the order of Mach 0.8, on the order of Mach 0.85 or in the range of from 0.8 to 0.85. Any single speed within these ranges may be part of the cruise condition. For some aircraft, the cruise conditions may be outside these ranges, for example below Mach 0.7 or above Mach 0.9.

Purely by way of example, the cruise conditions may correspond to standard atmospheric conditions (according to the International Standard Atmosphere, ISA) at an altitude that is in the range of from 10000 m to 15000 m, for example in the range of from 10000 m to 12000 m, for example in the range of from 10400 m to 11600 m (around 38000 ft), for example in the range of from 10500 m to 11500 m, for example in the range of from 10600 m to 11400 m, for example in the range of from 10700 m (around 35000 ft) to 11300 m, for example in the range of from 10800 m to 11200 m, for example in the range of from 10900 m to 11100 m, for example on the order of 11000 m. The cruise conditions may correspond to standard atmospheric conditions at any given altitude in these ranges.

Purely by way of example, the cruise conditions may correspond to an operating point of the engine that provides a known required thrust level (for example a value in the range of from 30 kN to 35 kN) at a forward Mach number of 0.8 and standard atmospheric conditions (according to the International Standard Atmosphere) at an altitude of 38000 ft (11582 m). Purely by way of further example, the cruise conditions may correspond to an operating point of the engine that provides a known required thrust level (for example a value in the range of from 50 kN to 65 kN) at a forward Mach number of 0.85 and standard atmospheric conditions (according to the International Standard Atmosphere) at an altitude of 35000 ft (10668 m).

In use, a gas turbine engine described and/or claimed herein may operate at the cruise conditions defined elsewhere herein. Such cruise conditions may be determined by the cruise conditions (for example the mid-cruise conditions) of an aircraft to which at least one (for example 2 or 4) gas turbine engine may be mounted in order to provide propulsive thrust.

Furthermore, the skilled person would immediately recognise either or both of descent and approach to refer to an operating phase within an aircraft flight cycle between cruise and landing of the aircraft. During either or both of descent and approach, the engine may be producing between 20% and 50% of available thrust. In further examples, the engine may be producing between 25% and 40% of available thrust. In yet further examples, the engine may be producing between 30% and 35% of available thrust. Additionally or alternatively, descent may refer to a nominal point in an aircraft flight cycle between take-off and landing, where a relative decrease in altitude is required, and which may require a reduced thrust demand of the engine.

According to an aspect, there is provided an aircraft comprising a gas turbine engine as described and/or claimed herein. The aircraft according to this aspect is the aircraft for which the gas turbine engine has been designed to be attached. Accordingly, the cruise conditions according to this aspect correspond to the mid-cruise of the aircraft, as defined elsewhere herein.

According to an aspect, there is provided a method of operating a gas turbine engine as described and/or claimed herein. The operation may be at the cruise conditions as defined elsewhere herein (for example in terms of the thrust, atmospheric conditions and Mach Number).

According to an aspect, there is provided a method of operating an aircraft comprising a gas turbine engine as described and/or claimed herein. The operation according to this aspect may include (or may be) operation at the mid-cruise of the aircraft, as defined elsewhere herein.

The skilled person will appreciate that except where mutually exclusive, a feature or parameter described in relation to any one of the above aspects may be applied to any other aspect. Furthermore, except where mutually exclusive, any feature or parameter described herein may be applied to any aspect and/or combined with any other feature or parameter described herein.

BRIEF DESCRIPTION OF THE DRAWINGS

Embodiments will now be described by way of example only, with reference to the Figures, in which.

DETAILED DESCRIPTION OF THE DISCLOSURE

Figure 1:
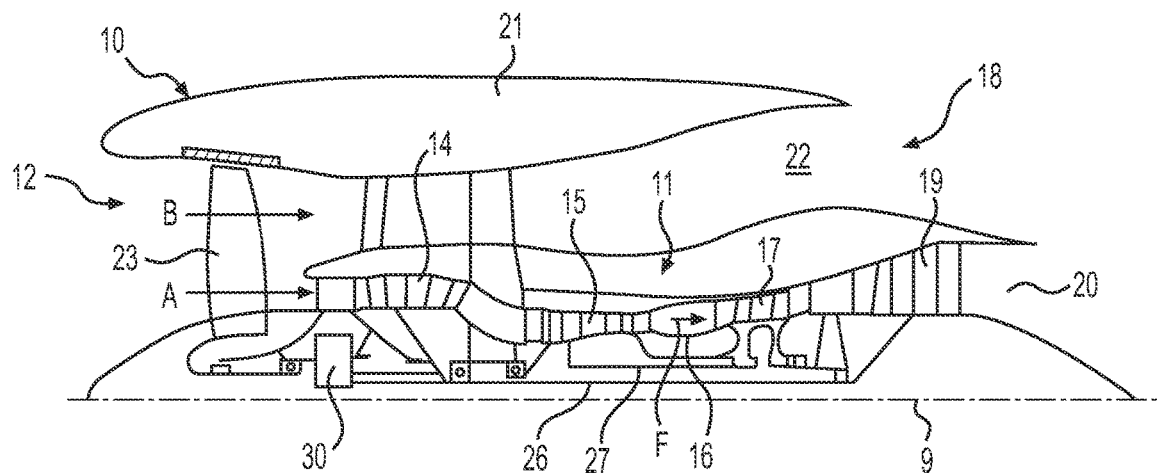
FIG. 1 is a sectional side view of a gas turbine engine.

FIG. 1 illustrates a gas turbine engine 10 having a principal rotational axis 9. The engine 10 comprises an air intake 12 and a propulsive fan 23 that generates two airflows: a core airflow A and a bypass airflow B. The gas turbine engine 10 comprises a core 11 that receives the core airflow A. The engine core 11 comprises, in axial flow series, a low pressure compressor 14, a high-pressure compressor 15, combustion equipment 16, a high-pressure turbine 17, a low pressure turbine 19 and a core exhaust nozzle 20. A nacelle 21 surrounds the gas turbine engine 10 and defines a bypass duct 22 and a bypass exhaust nozzle 18. The bypass airflow B flows through the bypass duct 22. The fan 23 is attached to and driven by the low pressure turbine 19 via a shaft 26 and an epicyclic gearbox 30.

In use, the core airflow A is accelerated and compressed by the low pressure compressor 14 and directed into the high pressure compressor 15 where further compression takes place. The compressed air exhausted from the high pressure compressor 15 is directed into the combustion equipment 16 where it is mixed with fuel F and the mixture is combusted. The resultant hot combustion products then expand through, and thereby drive, the high pressure and low pressure turbines 17, 19 before being exhausted through the nozzle 20 to provide some propulsive thrust. The high pressure turbine 17 drives the high pressure compressor 15 by a suitable interconnecting shaft 27. The fan 23 generally provides the majority of the propulsive thrust. The epicyclic gearbox 30 is a reduction gearbox.

Figure 2:
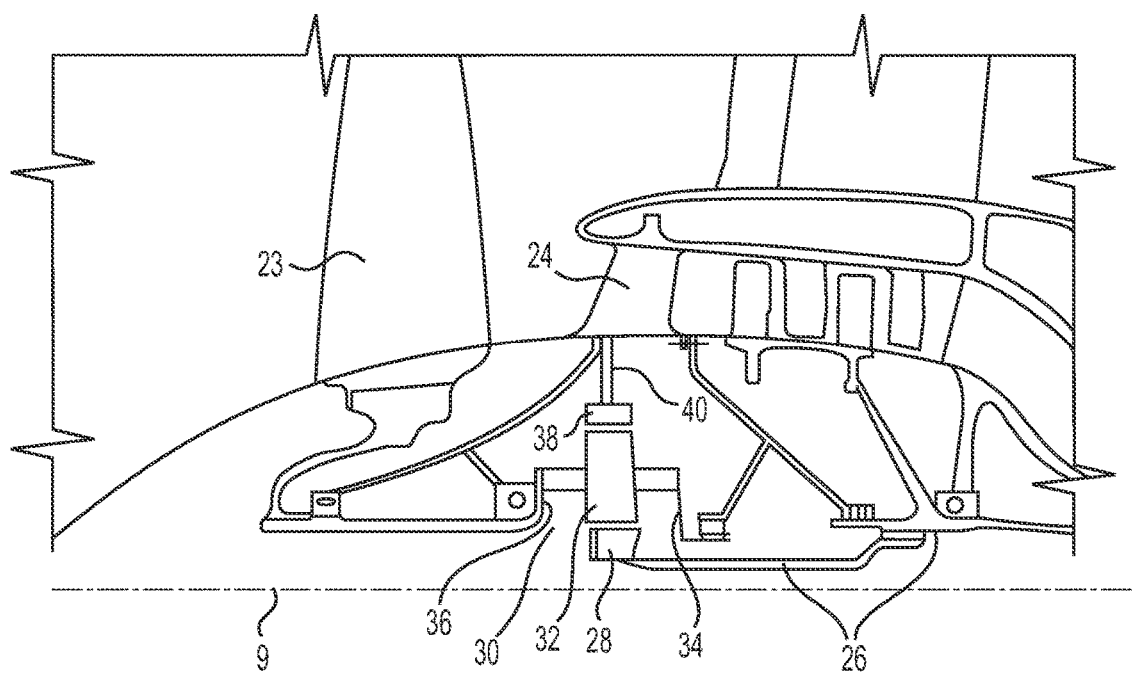
FIG. 2 is a close up sectional side view of an upstream portion of a gas turbine engine.

An exemplary arrangement for a geared fan gas turbine engine 10 is shown in FIG. 2. The low pressure turbine 19 (see FIG. 1) drives the shaft 26, which is coupled to a sun wheel, or sun gear, 28 of the epicyclic gear arrangement 30. Radially outwardly of the sun gear 28 and intermeshing therewith is a plurality of planet gears 32 that are coupled together by a planet carrier 34. The planet carrier 34 constrains the planet gears 32 to precess around the sun gear 28 in synchronicity whilst enabling each planet gear 32 to rotate about its own axis. The planet carrier 34 is coupled via linkages 36 to the fan 23 in order to drive its rotation about the engine axis 9. Radially outwardly of the planet gears 32 and intermeshing therewith is an annulus or ring gear 38 that is coupled, via linkages 40, to a stationary supporting structure 24.

Note that the terms "low pressure turbine" and "low pressure compressor" as used herein may be taken to mean the lowest pressure turbine stages and lowest pressure compressor stages (i.e. not including the fan 23) respectively and/or the turbine and compressor stages that are connected together by the interconnecting shaft 26 with the lowest rotational speed in the engine (i.e. not including the gearbox output shaft that drives the fan 23). In some literature, the "low pressure turbine" and "low pressure compressor" referred to herein may alternatively be known as the "intermediate pressure turbine" and "intermediate pressure compressor". Where such alternative nomenclature is used, the fan 23 may be referred to as a first, or lowest pressure, compression stage.

Figure 3:
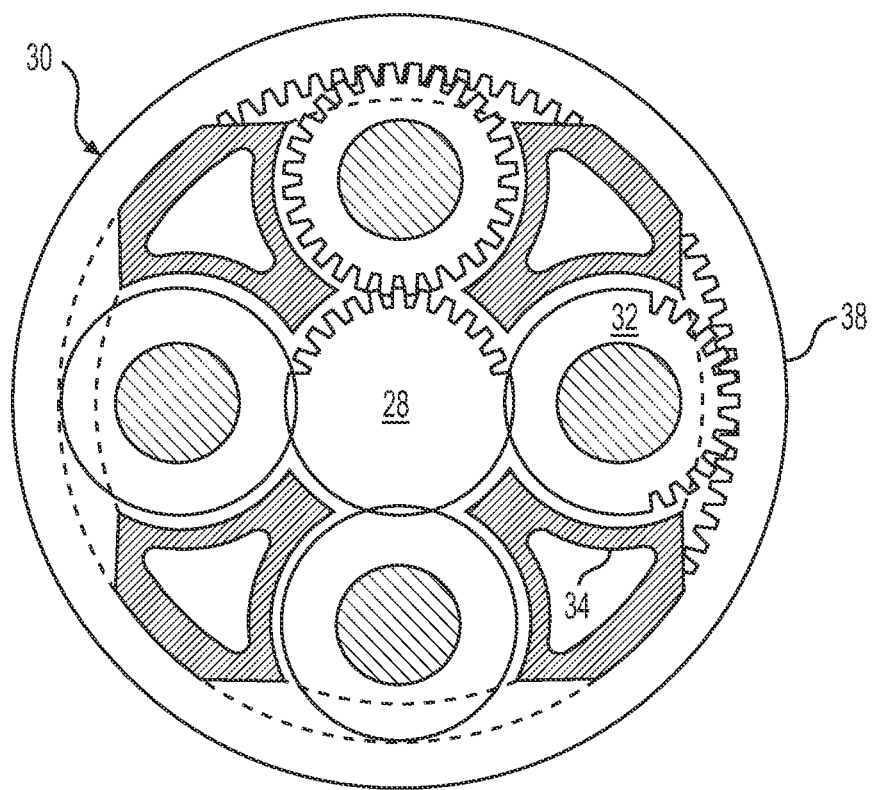
FIG. 3 is a partially cut-away view of a gearbox for a gas turbine engine.

The epicyclic gearbox 30 is shown by way of example in greater detail in FIG. 3. Each of the sun gear 28, planet gears 32 and ring gear 38 comprise teeth about their periphery to intermesh with the other gears. However, for clarity only exemplary portions of the teeth are illustrated in FIG. 3. There are four planet gears 32 illustrated, although it will be apparent to the skilled reader that more or fewer planet gears 32 may be provided within the scope of the claimed invention. Practical applications of a planetary epicyclic gearbox 30 generally comprise at least three planet gears 32.

The epicyclic gearbox 30 illustrated by way of example in FIGS. 2 and 3 is of the planetary type, in that the planet carrier 34 is coupled to an output shaft via linkages 36, with the ring gear 38 fixed. However, any other suitable type of epicyclic gearbox 30 may be used. By way of further example, the epicyclic gearbox 30 may be a star arrangement, in which the planet carrier 34 is held fixed, with the ring (or annulus) gear 38 allowed to rotate. In such an arrangement the fan 23 is driven by the ring gear 38. By way of further alternative example, the gearbox 30 may be a differential gearbox in which the ring gear 38 and the planet carrier 34 are both allowed to rotate.

It will be appreciated that the arrangement shown in FIGS. 2 and 3 is by way of example only, and various alternatives are within the scope of the present disclosure. Purely by way of example, any suitable arrangement may be used for locating the gearbox 30 in the engine 10 and/or for connecting the gearbox 30 to the engine 10. By way of further example, the connections (such as the linkages 36, 40 in the FIG. 2 example) between the gearbox 30 and other parts of the engine 10 (such as the input shaft 26, the output shaft and the fixed structure 24) may have any desired degree of stiffness or flexibility. By way of further example, any suitable arrangement of the bearings between rotating and stationary parts of the engine (for example between the input and output shafts from the gearbox and the fixed structures, such as the gearbox casing) may be used, and the disclosure is not limited to the exemplary arrangement of FIG. 2. For example, where the gearbox 30 has a star arrangement (described above), the skilled person would readily understand that the arrangement of output and support linkages and bearing locations would typically be different to that shown by way of example in FIG. 2.

Accordingly, the present disclosure extends to a gas turbine engine having any arrangement of gearbox styles (for example star or planetary), support structures, input and output shaft arrangement, and bearing locations.

Optionally, the gearbox may drive additional and/or alternative components (e.g. the intermediate pressure compressor and/or a booster compressor).

Other gas turbine engines to which the present disclosure may be applied may have alternative configurations. For example, such engines may have an alternative number of compressors and/or turbines and/or an alternative number of interconnecting shafts. By way of further example, the gas turbine engine shown in FIG. 1 has a split flow nozzle 18, 20 meaning that the flow through the bypass duct 22 has its own nozzle 18 that is separate to and radially outside the core engine nozzle 20. However, this is not limiting, and any aspect of the present disclosure may also apply to engines in which the flow through the bypass duct 22 and the flow through the core 11 are mixed, or combined, before (or upstream of) a single nozzle, which may be referred to as a mixed flow nozzle. One or both nozzles (whether mixed or split flow) may have a fixed or variable area.

Whilst the described example relates to a turbofan engine, the disclosure may apply, for example, to any type of gas turbine engine, such as an open rotor (in which the fan stage is not surrounded by a nacelle) or turboprop engine, for example. In some arrangements, the gas turbine engine 10 may not comprise a gearbox 30.

The geometry of the gas turbine engine 10, and components thereof, is defined by a conventional axis system, comprising an axial direction (which is aligned with the rotational axis 9), a radial direction (in the bottom-to-top direction in FIG. 1), and a circumferential direction (perpendicular to the page in the FIG. 1 view). The axial, radial and circumferential directions are mutually perpendicular.

The fuel F provided to the combustion equipment 16 may comprise a fossil-based hydrocarbon fuel, such as Kerosene. Thus, the fuel F may comprise molecules from one or more of the chemical families of n-alkanes, iso-alkanes, cycloalkanes, and aromatics. Additionally or alternatively, the fuel F may comprise renewable hydrocarbons produced from biological or non-biological resources, otherwise known as sustainable aviation fuel (SAF). In each of the provided examples, the fuel F may comprise one or more trace elements including, for example, sulphur, nitrogen, oxygen, inorganics, and metals.

Functional performance of a given composition, or blend of fuel for use in a given mission, may be defined, at least in part, by the ability of the fuel to service the Brayton cycle of the gas turbine engine 10. Parameters defining functional performance may include, for example, specific energy; energy density; thermal stability; and, emissions including particulate matter. A relatively higher specific energy (i.e. energy per unit mass), expressed as MJ/kg, may at least partially reduce take-off weight, thus potentially providing a relative improvement in fuel efficiency. A relatively higher energy density (i.e. energy per unit volume), expressed as MJ/L, may at least partially reduce take-off fuel volume, which may be particularly important for volume-limited missions or military operations involving refuelling. A relatively higher thermal stability (i.e. inhibition of fuel to degrade or coke under thermal stress) may permit the fuel to sustain elevated temperatures in the engine and fuel injectors, thus potentially providing relative improvements in combustion efficiency. Reduced emissions, including particulate matter, may permit reduced contrail formation, whilst reducing the environmental impact of a given mission. Other properties of the fuel may also be key to functional performance. For example, a relatively lower freeze point (° C.) may allow long-range missions to optimise flight profiles; minimum aromatic concentrations (%) may ensure sufficient swelling of certain materials used in the construction of o-rings and seals that have been previously exposed to fuels with high aromatic contents; and, a maximum surface tension (mN/m) may ensure sufficient spray break-up and atomisation of the fuel.

The ratio of the number of hydrogen atoms to the number of carbon atoms in a molecule may influence the specific energy of a given composition, or blend of fuel. Fuels with higher ratios of hydrogen atoms to carbon atoms may have higher specific energies in the absence of bond strain. For example, fossil-based hydrocarbon fuels may comprise molecules with approximately 7 to 18 carbons, with a significant portion of a given composition stemming from molecules with 9 to 15 carbons, with an average of 12 carbons.

ASTM International (ASTM) D7566, Standard Specification for Aviation Turbine Fuels Containing Synthesized Hydrocarbons (ASTM 2019c) approves a number of sustainable aviation fuel blends comprising between 10% and 50% sustainable aviation fuel (the remainder comprising one or more fossil-based hydrocarbon fuels, such as Kerosene), with further compositions awaiting approval. However, there is an anticipation in the aviation industry that sustainable aviation fuel blends comprising up to (and including) 100% sustainable aviation fuel (SAF) will be eventually approved for use.

Sustainable aviation fuels may comprise one or more of n-alkanes, iso-alkanes, cyclo-alkanes, and aromatics, and may be produced, for example, from one or more of synthesis gas (syngas); lipids (e.g. fats, oils, and greases); sugars; and alcohols. Thus, sustainable aviation fuels may comprise either or both of a lower aromatic and sulphur content, relative to fossil-based hydrocarbon fuels. Additionally or alternatively, sustainable aviation fuels may comprise either or both of a higher iso-alkane and cyclo-alkane content, relative to fossil-based hydrocarbon fuels. Thus, in some examples, sustainable aviation fuels may comprise either or both of a density of between 90% and 98% that of kerosene and a calorific value of between 101% and 105% that of kerosene.

Owing at least in part to the molecular structure of sustainable aviation fuels, sustainable aviation fuels may provide benefits including, for example, one or more of a higher energy density; higher specific energy; higher specific heat capacity; higher thermal stability; higher lubricity; lower viscosity; lower surface tension; lower freeze point; lower soot emissions; and, lower $CO_2$ emissions, relative to fossil-based hydrocarbon fuels (e.g. when combusted in the combustion equipment 16). Accordingly, relative to fossil-based hydrocarbon fuels, such as Kerosene, sustainable aviation fuels may lead to either or both of a relative decrease in specific fuel consumption, and a relative decrease in maintenance costs.

Figure 4:
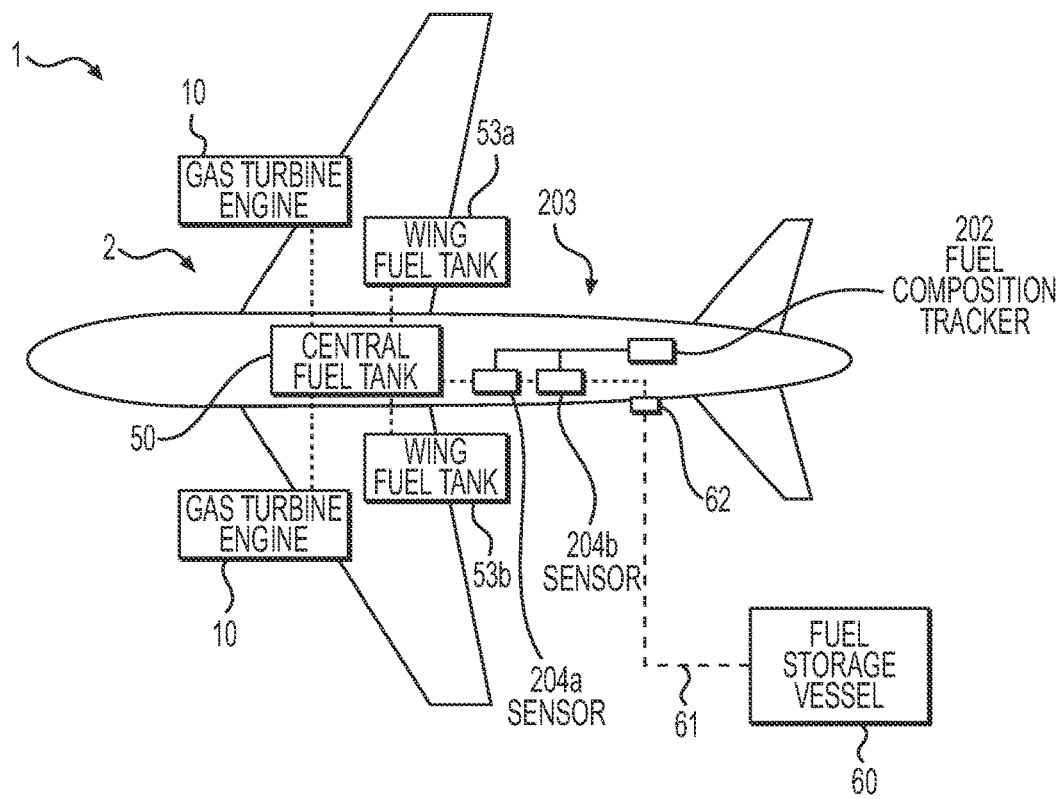
FIG. 4 is a schematic view of an aircraft including a fuel composition tracker.
Figure 7:
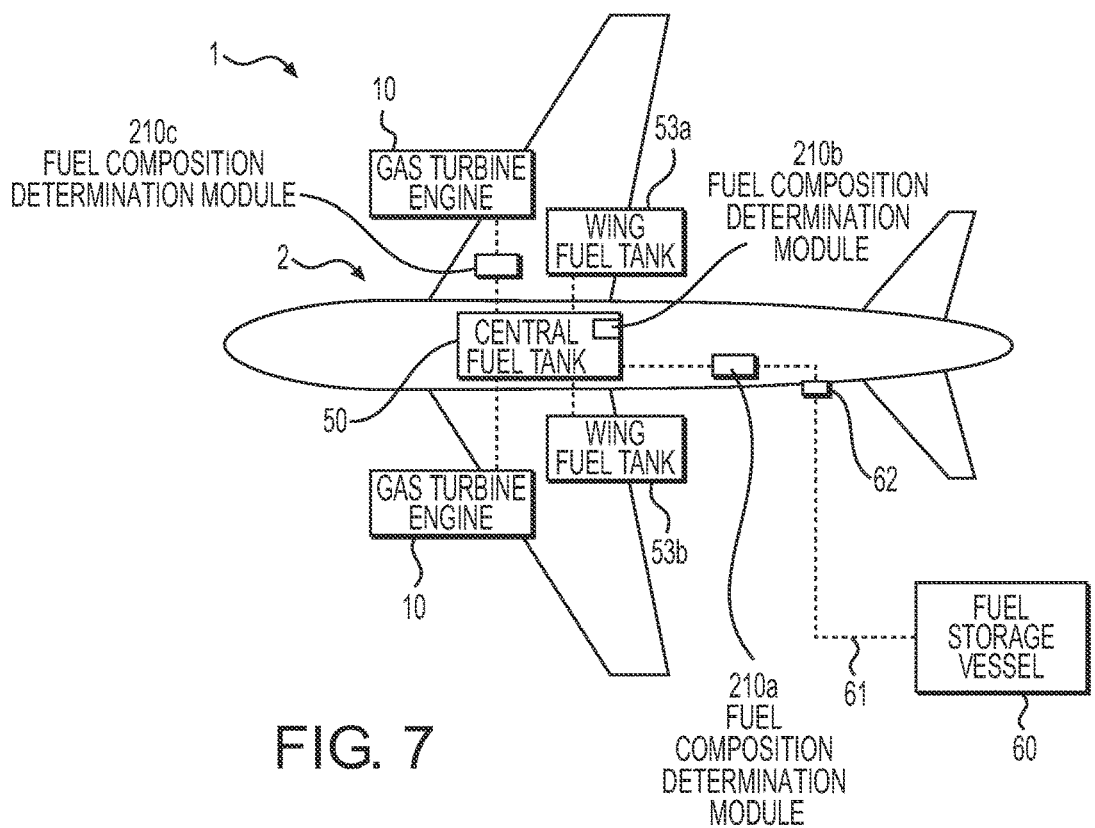
FIG. 7 is a schematic view of an aircraft including a fuel composition determination module.

As depicted in FIGS. 4 and 7, an aircraft 1 may comprise multiple fuel tanks 50, 53; for example a larger, primary fuel tank 50 located in the aircraft fuselage, and a smaller fuel tank 53a, 53b located in each wing. In other examples, an aircraft 1 may have only a single fuel tank 50, and/or the wing fuel tanks 53 may be larger than the central fuel tank 50, or no central fuel tank may be provided (with all fuel instead being stored in the aircraft's wings)—it will be appreciated that many different tank layouts are envisaged and that the examples pictured are provided for ease of description and not intended to be limiting.

FIG. 4 and FIG. 7 show an aircraft 1 with a propulsion system 2 comprising two gas turbine engines 10. The gas turbine engines 10 are supplied with fuel from a fuel supply system onboard the aircraft 1. The fuel supply system of the examples pictured comprises a single fuel source.

For the purposes of the present application the term "fuel source" means either 1) a single fuel tank or 2) a plurality of fuel tanks which are fluidly interconnected. Each fuel source is arranged to provide a separate source of fuel i.e. a first fuel source may contain a first fuel having a different characteristic or characteristics from a second fuel contained in a second fuel source. First and second fuel sources are therefore not fluidly coupled to each other so as to separate the different fuels (at least under normal running conditions).

In the present examples, the first (and, in these examples, only) fuel source comprises a centre fuel tank 50, located primarily in the fuselage of the aircraft 1 and a plurality of wing fuel tanks 53a, 53b, where at least one wing fuel tank is located in the port wing and at least one wing fuel tank is located in the starboard wing for balancing. All of the tanks 50, 53 are fluidly interconnected in the example shown, so forming a single fuel source. Each of the centre fuel tank 50 and the wing fuel tanks 53 may comprise a plurality of fluidly interconnected fuel tanks.

In another example, the wing fuel tanks 53a, 53b may not be fluidly connected to the central tank 50, so forming a separate, second fuel source. For balancing purposes, one or more fuel tanks in the port wing may be fluidly connected to one or more fuel tanks in the starboard wing. This may be done either via a centre fuel tank (if that tank does not form part of the other fuel source), or bypassing the centre fuel tank(s), or both (for maximum flexibility and safety).

In another example, the first fuel source comprises wing fuel tanks 53 and a centre fuel tank 50, while a second fuel source comprises a further separate centre fuel tank. Fluid interconnection between wing fuel tanks and the centre fuel tank of the first fuel source may be provided for balancing of the aircraft 1.

In some examples, the allocation of fuel tanks 50, 53 available on the aircraft 1 may be constrained such that the first fuel source and the second fuel source are each substantially symmetrical with respect to the aircraft centre line. In cases where an asymmetric fuel tank allocation is permitted, a suitable means of fuel transfer is generally provided between fuel tanks of the first fuel source and/or between fuel tanks of the second fuel source such that the position of the aircraft's centre of mass can be maintained within acceptable lateral limits throughout the flight.

An aircraft 1 may be refuelled by connecting a fuel storage vessel 60, such as that provided by an airport fuel truck, or a permanent pipeline, to a fuel line connection port 62 of the aircraft, via a fuel line 61. A desired amount of fuel may be transferred from the fuel storage vessel 60 to the one or more tanks 50, 53 of the aircraft 1. Especially in examples with more than one fuel source, in which different tanks 50, 53 are to be filled with different fuels, multiple fuel line connection ports 62 may be provided instead of one, and/or valves may be used to direct fuel appropriately.

Aircraft generally refuel at multiple different airports, for example at the beginning and end of a long-distance flight. Whilst there are standards with which all aviation fuels must be compliant, as mentioned above, different aviation fuels have different compositions, for example depending on their source (e.g. different petroleum sources, biofuels or other synthetic aviation fuels (often described as sustainable aviation fuels—SAFs), and/or mixtures of petroleum-based fuels, and other fuels) and on any additives included (e.g. such as antioxidants and metal deactivators, biocides, static reducers, icing inhibitors, corrosion inhibitors) and any impurities. As well as varying between airports and fuel suppliers, fuel composition of the available aviation fuel may vary between batches even for a given airport or fuel supplier. Further, fuel tanks 50, 53 of aircraft 1 are usually not emptied before being topped up for a subsequent flight, resulting in mixtures of different fuels within the tanks— effectively a fuel with a different composition resulting from the mixture.

The inventors appreciated that, as different fuels can have different properties, whilst still conforming to the standards, knowledge of the fuel(s) available to an aircraft 1 can allow more efficient, tailored, control of the aircraft 1, and more specifically of the aircraft's propulsion system 2 (i.e. the one or more gas turbine engines 10 of the aircraft 1, and associated controls and components). Knowledge of the fuel can therefore be used as a tool to improve aircraft performance, so monitoring fuel composition can provide benefits.

In various examples, an active infinite summing approach may be taken, to keep track of varying fuel composition of a fuel within a fuel tank 50, 53 with time, after multiple refills. For this approach, it is assumed that all aviation fuels are fully miscible, and that a homogeneous mixture is formed within a fuel tank 50, 53 at least in aircraft operation (partitioning of fuels in-tank due to differences in densities may be seen in static tanks, when a less dense fuel is added on top of a more dense fuel, but such partitioning would not be expected to remain in flight, as movements of the tank and vibrations of the system will induce mixing). A record may be kept for each fuel tank, in examples in which the aircraft 1 has multiple fuel tanks 50, 53.

Such an approach comprises obtaining one or more fuel characteristics of any fuel already present in the fuel tank 50, 53 prior to refuelling.

As used herein, the term "fuel characteristics" refers to intrinsic or inherent fuel properties such as fuel composition, not variable properties such as volume or temperature. Examples of fuel characteristics include one or more of:

i. the percentage of sustainable aviation fuel (SAF) in the fuel, or an indication that the fuel is a fossil fuel, for example fossil kerosene, or that the fuel is a pure SAF fuel;

ii. parameters of a hydrocarbon distribution of the fuel, such as:
   the aromatic hydrocarbon content of the fuel, and optionally also/alternatively the multi-aromatic hydrocarbon content of the fuel;
   the hydrogen to carbon ratio (H/C) of the fuel;
   % composition information for some or all hydrocarbons present;

iii. the presence or percentage of a particular element or species, such as:
   the percentage of nitrogen-containing species in the fuel;
   the presence or percentage of a tracer species or trace element in the fuel;
   naphthalene content of the fuel;

sulphur content of the fuel;
cycloparaffin content of the fuel;
oxygen content of the fuel;

iv. one or more properties of the fuel in use in a gas turbine engine 10, such as:
   level of non-volatile particulate matter (nvPM) emissions or $CO_2$ emissions on combustion;
   level of coking of the fuel;

v. one or more properties of the fuel itself, independent of use in an engine 10 or combustion, such as:
   thermal stability of the fuel (e.g. thermal breakdown temperature); and
   one or more physical properties such as density, viscosity, calorific value, freeze temperature, and/or heat capacity.

The fuel characteristics to be tracked may be selected based on which properties of the fuel are most relevant to changes which may be made to the propulsion system 2.

The obtaining fuel characteristics of any fuel already present in the fuel tank 50, 53 prior to refuelling may comprise one or more of:

(i) physically and/or chemically detecting one or more features or parameters of the composition of the fuel already present in the fuel tank 50, 53 (this may allow direct detection of the fuel characteristics, and/or may allow the fuel characteristics to be determined using the detection results), and/or detecting one or more tracer elements or compounds added to the fuel to facilitate its identification (e.g. a dye);

(ii) obtaining the result of an earlier determination performed using an active infinite summing approach as described herein, for example by retrieving one or more fuel characteristic values from a local data store on-board the aircraft 1;

(iii) receiving data, for example from an input provided at a user interface, or data transmitted to the aircraft 1.

In some examples, multiple different methods may be performed to obtain the fuel characteristics—for example, different methods may be used for different characteristics, and/or different methods may be used for the same characteristic as a check. In some examples, the obtaining the one or more fuel characteristics of any fuel already present in the fuel tank 50, 53 prior to refuelling may comprise obtaining stored fuel characteristic data, and chemically or physically detecting one or more parameters of any fuel already present in the fuel tank 50, 53 prior to refuelling, and checking this against the stored fuel characteristic data. The input to the calculating step described below may therefore be verified based on the one or more detected parameters. If there is a mis-match between the stored fuel characteristic and the corresponding detected parameter, an alert may be provided.

As mentioned above, for this approach it is generally assumed that the fuels are perfectly miscible, forming a homogeneous mixture within the tanks 50, 53. However, if there is any possibility of imperfect mixing of fuels within the tank 50, 53 (e.g. after a long period of no movement for a fuel mix known to contain fuels of differing densities), fuel composition coming out of the fuel tank 50, 53 on its way to the engine 10, 44 may be examined. If the measured, calculated, or otherwise determined fuel characteristics of fuel leaving the tank 50, 53 differ from those of the homogeneous mixture expected to be in the tank 50, 53, a possible issue with imperfect mixing may be flagged in some scenarios (e.g. if there is a significant density difference between the fuel already in the tank and the newly-added fuel, which could result in stratification) instead of, or as well as, flagging possible errors in understanding of the overall tank contents.

Fuel characteristics may be detected in various ways, both direct (e.g. from sensor data corresponding to the fuel characteristic in question) and indirect (e.g. by inference or calculation from other characteristics or measurements, or by reference to data for a specific detected tracer in the fuel). The characteristics may be determined as relative values as compared to another fuel, or as absolute values. For example, one or more of the following detection methods may be used:

The aromatic or cycloparaffin content of the fuel can be determined based on measurements of the swell of a sensor component made from a seal material such as a nitrile seal material.

Trace substances or species, either present naturally in the fuel or added to act as a tracer, may be used to determine fuel characteristics such as the percentage of sustainable aviation fuel in the fuel or whether the fuel is kerosene.

Measurements of the vibrational mode of a piezoelectric crystal exposed to the fuel can be used as the basis for the determination of various fuel characteristics including the aromatic content of the fuel, the oxygen content of the fuel, and the thermal stability or the coking level of the fuel—for example by measuring the build-up of surface deposits on the piezoelectric crystal which will result in a change in vibrational mode.

Various fuel characteristics may be determined by collecting performance parameters of the gas turbine engine 10 during a first period of operation (such as during take-off), and optionally also during a second period of operation (e.g. during cruise), and comparing these collected parameters to expected values if using fuel of known properties.

Various fuel characteristics including the aromatic hydrocarbon content of the fuel can be determined based on sensor measurements of the presence, absence, or degree of formation of a contrail by the gas turbine 10 during its operation.

Fuel characteristics including the aromatic hydrocarbon content can be determined based on a UV-Vis spectroscopy measurement performed on the fuel.

Various fuel characteristics including the sulphur content, naphthalene content, aromatic hydrogen content and hydrogen to carbon ratio may be determined by measurement of substances present in the exhaust gases emitted by the gas turbine engine 10 during its use.

Calorific value of the fuel may be determined in operation of the aircraft 1 based on measurements taken as the fuel is being burned—for example using fuel flow rate and shaft speed or change in temperature across the combustor 16.

Various fuel characteristics may be determined by making an operational change arranged to affect operation of the gas turbine engine 10, sensing a response to the operational change; and determining the one or more fuel characteristics of the fuel based on the response to the operational change.

Various fuel characteristics may be determined in relation to fuel characteristics of a first fuel by changing a fuel supplied to the gas turbine engine 10 from the first fuel to a second fuel, and determining the one or more fuel characteristics of the second fuel based on a change in a relationship between T30 and one of T40 and T41 (the relationship being indicative of the temperature rise across the combustor 16). The characteristics may be determined as relative values as compared to the first fuel, or as absolute values, e.g. by reference to known values for the first fuel.

(As used herein, T30, T40 and T41, and any other numbered pressures and temperatures, are defined using the station numbering listed in standard SAE AS755, in particular:

T30=High Pressure Compressor (HPC) Outlet Total Temperature;

T40=Combustion Exit Total Temperature;

T41=High Pressure Turbine (HPT) Rotor Entry Total Temperature.)

In the examples currently being described, the amount of fuel present in the tank 50, 53 prior to refuelling (e.g. mass, volume, and/or % full) is also noted, for example being automatically detected and recorded in computational storage/memory onboard the aircraft 1.

In addition to obtaining one or more fuel characteristics of any fuel already present in the fuel tank 50, 53 prior to refuelling, one or more fuel characteristics of a fuel to be added to the fuel tank 50, 53 on refuelling are also obtained.

The obtaining fuel characteristics of the fuel to be added to the fuel tank 50, 53 on refuelling may comprise one or more of:

(i) physically and/or chemically detecting one or more features of the composition of the fuel (e.g. in a testing unit off-wing, or as the fuel is transported to a fuel tank on-wing, or indeed in use in the gas turbine engine 10), so allowing direct detection of the fuel characteristics or providing data from which they can be determined, as mentioned above, and/or detecting one or more tracer elements or compounds added to the fuel to facilitate its identification (e.g. a dye);

(iii) receiving data, for example from an input provided at a user interface, or data transmitted to the aircraft, e.g. by scanning a barcode associated with the fuel delivery.

As for obtaining fuel characteristics of fuel already in the tank 50, 53, in some examples, multiple different methods maybe performed to obtain the fuel characteristics of the resultant fuel mixture—for example, different methods may be used for different characteristics, and/or different methods may be used for the same characteristic as a check. Any suitable detection method(s) as mentioned above may be used. Assuming that the assumption of even mixing applies, fuel characteristics of fuel leaving the tank 50, 53 and entering the engine 10 may be determined as a means of validating the outcome of calculating 2006 the fuel characteristics of the mixture.

In the examples currently being described, an amount of fuel added to the tank 50, 53 on refuelling (e.g. explicitly by mass added, or volume added, and/or implicitly by change in mass, volume, or % full) is also noted (e.g. being automatically detected, or provided by a fuel supplier, and recorded in computational storage/memory onboard the aircraft 1).

One or more fuel characteristics of the resultant fuel in the fuel tank 50, 53 after refuelling are then calculated using the data on any fuel initially in the tank, and the data on the fuel added to the tank. Such calculations may be performed for each fuel source separately—for example, a first fuel source may be empty prior to refuelling and so contain only the new fuel, and a second fuel source may not be empty prior to refuelling and may contain a mixture of the old and new fuels after refuelling. In such cases, burning fuel from the first fuel source in the gas turbine engine 10 may allow fuel characteristics of the new fuel to be determined, and fuel characteristics of the mixture in the second fuel source may then be calculated using the determined characteristics for the new fuel, the blend percentage, and data on the older fuel.

Current fuel characteristic data for the fuel in the tank may be stored, updating the recorded fuel characteristics of the fuel present in the fuel tank 50, 53 following each refuelling of the aircraft 1. Optionally, a continuous record of fuel compositions used with time may be kept; alternatively, only a current fuel composition may be stored.

Figure 6:
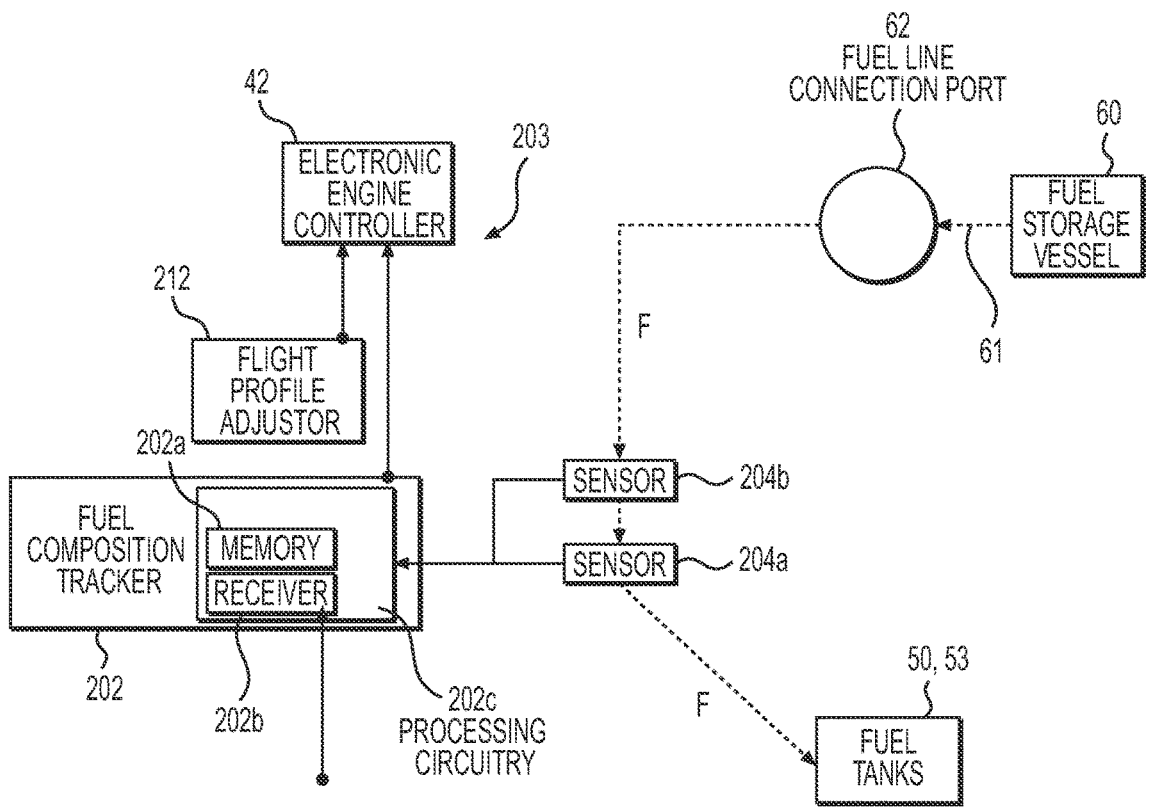
FIG. 6 is a schematic view of an aircraft fuel composition tracking system, in context with a fuel supply line and on-board tank, indicating optional use as a fuel composition determination module.

A fuel composition tracker 202 may be used to record and store fuel composition data, and optionally also to receive the fuel characteristics of the fuel to be added on refuelling, and calculate updated fuel composition data. The fuel composition tracker 202 may be provided as a separate fuel composition tracking unit 202, as shown in FIGS. 4 and 6, or as a module built into the propulsion system 2, and/or as software and/or hardware incorporated into the pre-existing aircraft control systems, e.g. as a part of an electronic engine controller (EEC) 42.

In the example shown, two sensors 204a, 204b are provided, each arranged to physically and/or chemically detect one or more features of the composition of the fuel being added to the fuel tank 50, 53 on refuelling. The sensors 204 and the fuel composition tracker 202 together may be described as a fuel composition tracking system 203, as shown in FIG. 6.

In alternative examples, no such sensors 204 may be provided (for example, a barcode associated with the fuel storage vessel 60 may be read and the corresponding data on the fuel provided to the fuel composition tracker 202), or more or fewer sensors may be provided.

Some examples may further comprise chemically or physically detecting one or more parameters of the resultant fuel in the fuel tank 50, 53 after refuelling. The detected parameters may then be compared to one or more of the calculated fuel characteristics, to verify the result. If there is a mis-match between the calculated fuel characteristic and the corresponding detected parameter, an alert may be provided.

An active infinite summing approach as described herein could be used continually throughout the lifetime of an aircraft 1 (or between services in which a fuel tank 50, 53 may be drained). However, it may be beneficial to re-baseline the fuel composition data at intervals.

Re-baselining may comprise chemically and/or physically determining one or more parameters of the fuel in the fuel tank 50, 53, and using the determined values to replace the stored fuel characteristics for the fuel in the fuel tank.

In some examples, the chemically and/or physically determining one or more parameters of the fuel in the fuel tank 50, 53 for baselining may be performed by extracting a sample of the fuel from the fuel tank for off-wing testing; for example, it may be sent to a laboratory for analysis, or provided to a ground-based testing station available at an airport. In other examples, on-wing, and optionally in situ, testing methods may be used.

Re-baselining (i.e. chemically and/or physically determining one or more parameters of the fuel in the fuel tank 50, 53 and using the determined values to replace the stored fuel characteristics for the fuel in the fuel tank) may be performed in response to a trigger event. A trigger event may be a threshold amount of time having elapsed since a previous (chemical and/or physical) determination of the one or more parameters of the fuel in the fuel tank, or a threshold number of refuelling events and/or flights having been reached since a previous (chemical and/or physical) determination of the one or more parameters of the fuel in the fuel tank.

Additionally or alternatively, a trigger event may be the detection of a discrepancy between one or more of the calculated characteristics and a detected parameter—for example when a calculated value differs from a detected value by an amount exceeding a threshold or tolerance value. In some examples, an alert is provided (e.g. an audible and/or visible alarm, and/or a message sent to the pilot or another party) on detection of such a discrepancy—a decision may then be taken as to whether to re-baseline immediately, or to accept that uncertainty in fuel composition may mean being unable to operate most efficiently for the next flight(s) until an opportunity to re-baseline becomes available. Smart control of the propulsion system 2 based on fuel characteristics may be disabled until the next re-baselining event.

Once the one or more fuel characteristics of the resultant fuel in the fuel tank 50, 53 after refuelling have been determined, the propulsion system 2 can be controlled based on the calculated fuel characteristics.

For example:

An operating parameter of a heat management system of the aircraft (e.g. a fuel-oil heat exchanger) may be changed, or the temperature of fuel supplied to the combustor 16 of the engine 10 can be changed.

When more than one fuel is stored aboard an aircraft 1, a selection of which fuel to use for which operations (e.g. for ground-based operations as opposed to flight, for low-temperature start-up, or for operations with different thrust demands) may be made based on fuel characteristics such as % SAF, nvPM generation potential, viscosity, and calorific value. A fuel delivery system may therefore be controlled appropriately based on the fuel characteristics.

One or more flight control surfaces of the aircraft 1 may be adjusted so as to change route and/or altitude based on knowledge of the fuel.

The spill percentage of a fuel pump (i.e. the proportion of pumped fuel recirculated instead of being passed to the combustor) may be changed, e.g. based on the % SAF of the fuel. The pump and/or one or more valves may therefore be controlled appropriately based on the fuel characteristics.

Changes to the scheduling of variable-inlet guide vanes (VIGVs) may be made based on fuel characteristics. The VIGVs may therefore be moved, or a movement of the VIGVs be cancelled, as appropriate based on the fuel characteristics.

A propulsion system 2 for an aircraft may therefore comprise a fuel composition tracking system 203 arranged to:

store 2002 current fuel characteristic data, the fuel characteristic data comprising one or more fuel characteristics of fuel present in the fuel tank 50, 53;

obtain 2004 one or more fuel characteristics of a fuel added to the fuel tank 50, 53 on refuelling; and calculate 2006 updated values for the one or more fuel characteristics of the fuel in the fuel tank 50, 53 after refuelling.

The obtaining 2004 of the one or more fuel characteristics of a fuel added to the fuel tank 50, 53 on refuelling may be performed before, during, or after the refuelling itself, for example using an off-wing testing unit, fuel line sensors, or gas turbine engine performance sensors, respectively, or indeed receiving data electronically from a third party.

FIG. 6 shows an example of a fuel composition tracking system 203, in the context of a refuelling event in which a fuel F is supplied to a fuel tank 50, 53. Arrows with dashed lines in FIG. 6 indicate fuel flow, whereas solid lines indicate electronic communication.

The fuel composition tracking system 203 comprises a fuel composition tracker 202. The fuel composition tracker 202 of the example being described comprises memory 202a (which may also be referred to as computational storage) arranged to store the current fuel characteristic data, and processing circuitry 202c arranged to calculate updated values for the one or more fuel characteristics of the fuel in the fuel tank 50, 53 after refuelling. The calculated values may then replace the previously-stored fuel characteristic data in the memory, and/or may be time- and/or date-stamped and added to the memory. A log of fuel characteristic data with time may therefore be assembled.

The fuel composition tracker 202 of the example shown also includes a receiver 202b arranged to receive data relating to fuel composition and/or requests for fuel composition information. The fuel composition tracker 202 of the example shown forms a part of, or is in communication with, an electronic engine controller (EEC) 42. The EEC 42 may be arranged to issue propulsion system control commands based on the calculated fuel characteristics. It will be appreciated that an EEC 42 may be provided for each gas turbine engine 10 of the aircraft 1, and that the role played by the EEC in or for the fuel composition tracker 202 may be just a small part of the functionality of the EEC. Indeed, the fuel composition tracker 202 may be provided by the EEC, or may comprise an EEC module distinct from the engine's EEC 42 in various implementations. In alternative examples, the fuel composition tracker 202 may not comprise any engine control functionality, and may instead simply supply fuel composition data on demand, to be used as appropriate by another system. Optionally, the fuel composition tracker 202 may supply a proposed change in engine control functionality for approval by a pilot; the pilot may then implement the proposed change directly, or approve or reject the automatic making of the proposed change.

Figure 5:
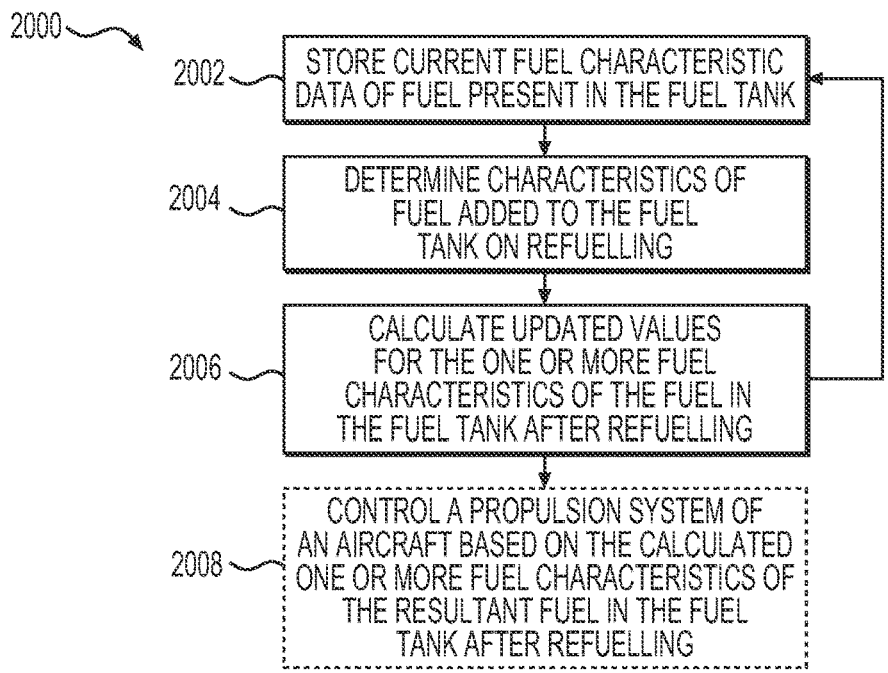
FIG. 5 is a schematic representation of a fuel identification method.

The method 2000 performed is illustrated in FIG. 5. At step 2002, current fuel characteristic data, comprising one or more fuel characteristics of fuel present in the fuel tank 50, 53, are stored, optionally in memory of a fuel composition tracker 202. These data may be provided for storage in any suitable way, for example being manually entered, e.g. via a graphical user interface in communication with the fuel composition tracker 202, electronically communicated to the fuel composition tracker 202, e.g. by wired or wireless communication from a barcode scanner following reading of a barcode (or equivalently any other type of optically- or otherwise-readable code, such as a QR code), and/or determined from sensor data. It will be appreciated that, if the tank 50, 53 is currently empty, null values or equivalent may be stored.

At step 2004, characteristics of a fuel added to the fuel tank 50, 53 on refuelling are determined. The determination may be performed by the fuel composition tracker 202 itself, e.g. by interpreting sensor data, or fuel characteristics determined elsewhere may be provided to the fuel composition tracker 202.

At step 2006, updated values for the one or more fuel characteristics of the fuel in the fuel tank 50, 53 after refuelling are calculated, optionally by the fuel composition tracker 202, using the stored fuel characteristic data (if any/if not null) and the obtained fuel characteristics.

The method 2000 may then be iterated on or after each refuelling event, returning to step 2002, with the updated values replacing the stored values (or being added to storage as part of a log), and proceeding accordingly.

The method 2000 may further comprise controlling 2008 a propulsion system 2 of an aircraft 1 based on the calculated one or more fuel characteristics of the resultant fuel in the fuel tank 50, 53 after refuelling. Updated values may be used to influence that control after each refuelling event. The controlling 2008 may be performed automatically in response to the determination of fuel properties, or after approval by a pilot, following the pilot being notified of a proposed change. In some examples, the same method 2000 may include automatically making some changes, and requesting others, depending on the nature of the change. In particular, changes which are "transparent" to the pilot—such as internal changes within engine flows which do not affect engine power output and would not be noticed by a pilot—may be made automatically, whereas any changes which the pilot would notice may be notified to the pilot (i.e. a notification appearing that the change will happen unless the pilot directs otherwise) or suggested to the pilot (i.e. the change will not happen without positive input from the pilot). In implementations in which a notification or suggestion is provided to a pilot, this may be provided on a cockpit display of the aircraft and/or as an audible alarm, and/or sent to a separate device such as a portable tablet or other computing device.

In examples in which an aircraft 1 has multiple fuel tanks 50, 53 which are all fluidly linked such that the fuels in all of the tanks 50, 53 are equivalent, a single set of fuel composition data may be stored and updated. In examples in which an aircraft 1 has multiple fuel tanks 50, 53 which are not fluidly linked, such that there may be differences between fuels in the different tanks 50, 53, a separate set of fuel composition data may be stored and updated for each tank. In such cases, a determination of which fuel is being supplied to the gas turbine engine 10 may be performed prior to the making or suggestion of any propulsion system control changes.

The inventors also appreciated that, as different fuels can have different properties, whilst still conforming to the standards, knowledge of the fuel(s) available to an aircraft 1 can allow more efficient, tailored, control of the flight profile. For example, a fuel with a higher hydrogen to carbon ratio may allow the formation of contrails at higher threshold temperatures/lower altitudes, and a choice may be made to fly at a slightly higher altitude (e.g. 100 m to 200 m higher), or to move to an adjacent discrete flight level (generally separated by 2000 feet vertical distance by current policies) to compensate for the otherwise-increased contrail formation. Additionally or alternatively, a different route may be selected to travel through slightly warmer or less humid air so as to reduce contrail formation. Knowledge of the fuel can therefore be used as a tool to improve aircraft performance, for example by reducing contrail formation. It will be appreciated that contrail formation is described here by way of example only, and is not intended to be limiting. Advance knowledge of the fuel for a flight of an aircraft 1 may therefore be used for advance planning and tailoring of details of the flight profile, so improving environmental outcomes and/or aircraft performance.

One or more fuel characteristics of a fuel arranged to be provided to a gas turbine engine 10 of an aircraft may therefore be determined. The fuel characteristics may include one or more of the fuel characteristics listed above.

The determination may be performed in many different ways. For example:
- a bar code of a fuel to be added to a fuel tank 50, 53 of the aircraft 1 may be scanned to read data of the fuel, or a tracer substance (e.g. a dye) identified and fuel properties looked up based on that tracer;
- data may be manually entered, or transmitted to the aircraft 1;
- a fuel sample may be extracted for ground-side analysis prior to take-off;
- fuel properties may be inferred from measurements of the propulsion system activity during one or more periods of aircraft operation, e.g. engine warm-up (including any engine use prior to movement of the aircraft 1) taxi, take-off, climb and/or cruise; and/or
- one or more fuel properties may be detected in-flight, for example using in-line sensors and/or other measurements.

The fuel characteristics may therefore be chemically and/or physically detected, determined from other sensed data, or otherwise determined.

In some examples, combinations of these techniques may be used to determine and/or verify one or more fuel characteristics, for example using one or more of the example detection techniques described above.

In some examples, such as those shown in FIGS. 4 and 7 described above, the aircraft 1 may have only a single fuel tank 50 (which may be in the form of a pair of linked wing tanks rather than a central tank), and/or may have multiple fuel tanks 50, 53 which each contain the same fuel, and/or are fluidly linked, or fluidly connected to the gas turbine engine 10, such that only a single fuel type is supplied to the gas turbine engine 10 between refuelling events—i.e. the fuel characteristics may remain constant throughout a flight.

In other examples, the aircraft 1 may have a plurality of fuel tanks 50, 53 which contain fuels of different compositions, and the propulsion system 2 may comprise an adjustable fuel delivery system, allowing a selection to be made of which tank(s), and therefore what fuel/fuel blend, to use. In such examples, the fuel characteristics may vary over the course of a flight, and a specific fuel or fuel blend may be selected to improve operation at certain flight stages or in certain external conditions.

Once one or more fuel characteristics have been determined, a flight profile may be selected, changed, or adjusted based on those fuel characteristics. In many examples, external data—for example weather data such as humidity and temperature data, and time data such as day vs. night—may be used in combination with the determined fuel characteristics to select or adjust the flight profile.

For example, the method implemented may comprise receiving forecast weather conditions for an intended route of the aircraft 1. These received forecast weather conditions may be used to make or influence changes in planned route and/or altitude, or used to guide planning of the route and/or altitude.

As used herein, the term "flight profile" refers to the operational characteristics (e.g. height/altitude, power setting, flight path angle, airspeed, and the like) of an aircraft 1 as it flies along a flight track, and also to the trajectory/flight track (route) itself. Changes of route are therefore included in the term "flight profile" as used herein.

In examples in which some or all of the fuel characteristics are inferred from measurements of the propulsion system activity during early stages of aircraft operation, for example start-up/engine warm-up, taxi, take-off and climb, or otherwise measured on-wing, the flight profile during cruise may be adjusted even if knowledge of the fuel characteristics is not available in time to guide the flight profile in the earlier stages of operation.

In examples in which some or all of the fuel characteristics are determined prior to take-off (e.g. on refuelling, or by analysis of the propulsion system 2 during taxiing), the flight profile for take-off and/or climb may also be adjusted; for example a take-off time, direction, and/or steepness of ascent may be selected to avoid higher-humidity regions or time periods.

In either case, the future course and/or operational characteristics of the aircraft 1 can be adjusted based on the determined fuel characteristics—advance planning of how to control the aircraft 1 based on the available fuel, and in particular of a specific flight trajectory (in particular, route and altitude), can therefore be performed.

A propulsion system 2 for an aircraft 1 may therefore comprise a fuel composition determination module 210 arranged to determine 2052 one or more fuel characteristics of the fuel arranged to be provided to the gas turbine engine 10; and a flight profile adjustor 212 arranged to propose or initiate a change to the planned flight profile based on the one or more fuel characteristics of the fuel.

In some examples, the fuel characteristics may be determined a period of time before a flight is due to commence and planned changes to the flight profile may then be proposed to a pilot and/or air traffic controller or other authority (optionally via an automated system), so as to obtain approval of the changes prior to take-off. In other examples, the changes made may be minor enough to not require sign-off from air traffic control, nor indeed from the pilot, and may be implemented automatically. An automated notification or proposal of the change may be provided to air traffic control and/or to the pilot, as appropriate. The notification or proposal may be provided on a cockpit display of the aircraft 1, and/or sent to a separate device such as a portable tablet or other computing device.

If the fuel composition is known far enough in advance of the flight, one or more appropriate authorities with whom a flight plan has been filed may also be notified of a change in flight plan, or a new flight plan may be filed with them.

Examples in which fuel composition may be known for certain well in advance of a flight might include cases where an aircraft 1 carries enough fuel for its current flight from a first airport to a second, and for its next intended flight onwards (or back to the first airport) from the second airport. A decision to carry excess fuel, rather than refuelling at the second airport, may be taken to enable a fast turnaround at the second airport or to avoid high fuel prices at the second airport, or indeed if a fuel composition available at the second airport is not desirable. Thus, after loading fuel at the first airport, any changes that might need to be made for the second flight from the second airport may be determined before or during the first flight, and a filed flight plan for the second flight may be replaced or adjusted accordingly.

Various different locations and types of fuel composition determination module 210 may be used depending on when, where, and how, fuel composition is to be determined. For example, fuel composition may be determined for fuel when it first enters the aircraft 1, via a fuel line connection port 62, with a fuel composition determination module 210a optionally located along a fuel supply line within the aircraft 1, leading from the fuel line connection port 62 to a tank 50, 53. It will be appreciated that if fuel composition data are provided to the aircraft 1, manually or electronically, on refuelling, no sensing or measurement of the incoming fuel may be required and the fuel composition determination module 210a may be located wherever is convenient and arranged to receive that data. Alternatively (or additionally), fuel composition may be determined for fuel within a tank 50, 53, with a fuel composition determination module 210b optionally located in or adjacent a tank 50, 53 within the aircraft 1. Alternatively (or additionally), fuel composition may be determined for fuel approaching a combustor 16 of the gas turbine engine 10, with a fuel composition determination module 210c optionally located near a fuel feed line from the fuel tank 50, 53 to the combustor 16, or using any other approach described above. In some examples, one or more fuel characteristic sensors may be provided integrally with processing circuitry and/or memory of the fuel composition determination module 210. In alternative examples, one or more fuel characteristic sensors may be located remotely from, and be in communication with, processing circuitry and/or memory of the fuel composition determination module 210. In alternative or additional examples, one or more fuel characteristics may be communicated to the fuel composition determination module 210, which may in such cases not comprise one or more sensors. The location of processing circuitry and/or memory of the fuel composition determination module 210 may vary accordingly. It will be appreciated that, whilst FIG. 7 shows three fuel composition determination modules 210a, b, c, these are provided to demonstrate possible locations only—just a single fuel composition determination module 210 may be provided in other examples. A second fuel composition determination module 210 may be provided in some examples, to provide a redundant check, and/or to determine fuel composition of a different fuel source, in examples in which an aircraft 1 comprises one or more fuel tanks 50, 53 which are not fluidly linked.

In some examples, fuel composition may be detected when the aircraft 1 is refuelled. The fuel composition determination module 210a in such examples may be or comprise a fuel composition tracker 202.

In such examples, a fuel composition tracker 202 as shown in FIG. 6 may be used to record and store fuel composition data, and optionally also to receive the fuel characteristics of the fuel to be added on refuelling, and calculate updated fuel composition data as described above. Arrows with dashed lines in FIG. 6 indicate fuel flow, whereas solid lines indicate electronic communication.

The active infinite summing approach described above may therefore be used in conjunction with the flight profile adaptation approach currently being described, or either approach may be used in isolation. The flight profile adjustor 212 shown in FIG. 6 may not be present in examples in which the flight profile adaptation approach currently being described is not implemented.

As mentioned above with respect to the earlier examples, the fuel composition tracker 202 may be provided as a separate fuel composition tracking unit 202, as shown in FIG. 6, or as a module built into the propulsion system 2, and/or as software and/or hardware incorporated into the pre-existing aircraft control systems, e.g. the EEC 42.

In the example shown, two sensors 204a, 204b are provided, each arranged to physically and/or chemically detect one or more features of the fuel being added to the fuel tank 50, 53 on refuelling. The sensors 204 and the fuel composition tracker 202 together may be described as a fuel composition tracking system 203, as shown in FIG. 6.

The fuel composition tracking system 203 comprises a fuel composition tracker 202. The fuel composition tracker 202 of the example being described comprises memory 202a arranged to store the current fuel characteristic data, and processing circuitry 202c arranged to calculate updated values for the one or more fuel characteristics of the fuel in the fuel tank 50, 53 after refuelling. The calculated values may then replace the previously stored fuel characteristic data in the memory, and/or may be time- and/or date-stamped and added to the memory. A log of fuel characteristic data with time may therefore be assembled.

The fuel composition tracker 202 of the example shown also includes a receiver 202b arranged to receive data relating to fuel composition and/or requests for fuel composition information. The fuel composition determination module 210 may therefore comprise a receiver 202b arranged to receive data relating to fuel composition, from which one or more fuel characteristics can be determined (either directly by extraction, or by calculation, optionally in conjunction with data from another source).

The fuel composition determination module 210 may therefore comprise, or have access to the output of, one or more sensors 204 arranged to provide data relating to one or more fuel characteristics. The sensor data may provide one or more fuel characteristics directly, or may allow one or more fuel characteristics to be obtained by calculation, optionally in conjunction with data from another source. In alternative examples, no such sensors 204 may be provided (for example, a barcode associated with the fuel storage vessel 60 may be read and the corresponding data on the fuel provided to the fuel composition tracker 202), or more or fewer sensors may be provided.

Data from the fuel composition tracker 202 may be used to change the planned flight profile, based on the one or more fuel characteristics.

A flight profile adjustor 212 may be used to change the planned flight profile based on the one or more fuel characteristics of the fuel, based on data provided by the fuel composition tracker 202 and optionally also other data. The flight profile adjustor 212 may be provided as a separate flight profile adjusting unit 212 built into the propulsion system 2, and/or as software and/or hardware incorporated into the pre-existing aircraft control systems, such as the EEC 42. Fuel composition tracking abilities (e.g. tracker 202) may be provided as part of the same unit or package.

Figure 8:
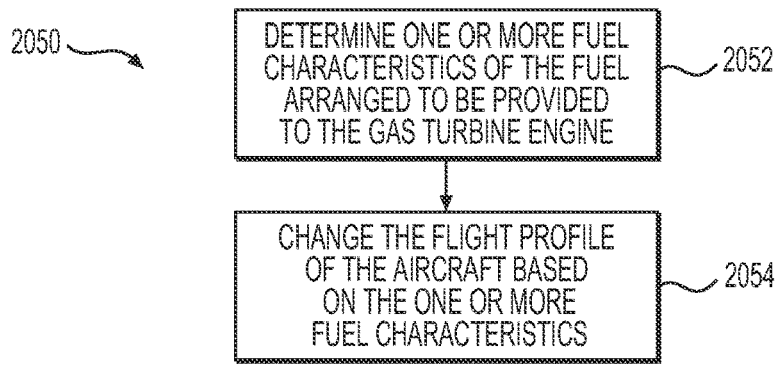
FIG. 8 is a schematic representation of an aircraft operation method.

The flight profile control method 2050 performed is illustrated in FIG. 8. At step 2052, one or more fuel characteristics of the fuel arranged to be provided to the gas turbine engine 10 are determined, optionally using any of the methods described above.

At step 2054, the flight profile of the aircraft 1 is changed based on the one or more fuel characteristics. The change in flight profile may be or comprise a change to one or more of trajectory, route, angle of attack, and altitude.

A flight profile adjustor 212 may be used to initiate and/or effect the change in flight profile. In some examples, the flight profile adjustor 212 may change the flight profile itself, and, in some implementations, may additionally control implementation of that change, for example recording a planned change and then providing a command to one or more flight control surfaces of the aircraft 1 so as to change altitude at the appropriate time. In other examples, the flight profile adjustor 212 may seek approval for the planned change, and/or may not itself send instructions to cause the change in flight profile. The flight profile adjustor 212 may therefore provide a notification or suggestion of a proposed change in flight profile to the pilot and/or another authority regarding the planned change, for approval. A notification or suggestion may be provided to a pilot on a cockpit display of the aircraft, and/or sent to a separate device such as a portable tablet or other computing device, for example. In some examples, the same flight profile adjustor 212 may automatically make some changes, and request approval of others, depending on the nature of the change (e.g. whether or not the planned change is significant enough to need authorisation from air traffic control, or another authority). The flight profile adjustor 212 may therefore propose and/or initiate a change 2054 to a flight profile of the aircraft 1 based on the at least one fuel characteristic.

The inventors also appreciated that knowledge of the one or more fuel characteristics selected and determined in any of the ways described above may be used to suggest, guide, or make in-flight adjustments to the propulsion system 2, so as to further improve aircraft performance. For example, a fuel with a higher heat capacity may be used for more engine cooling than a fuel with a lower heat capacity, and a fuel with a higher calorific value may allow a lower flow rate of fuel to be supplied to the combustor for the same power output. Knowledge of the fuel can therefore be used as a tool to improve aircraft performance in flight. As compared to the advance planning and flight profile changes described above, real-time or near-real-time decisions may be made and implemented, and these decisions may only affect the internal workings of the engine 10 rather than changing route and/or altitude, for example.

In some examples, the aircraft 1 may have only a single fuel tank 50, and/or may have multiple fuel tanks 50, 53 which each contain the same fuel, and/or are fluidly linked, or fluidly connected to the gas turbine engine 10, such that only a single fuel type is supplied to the gas turbine engine 10 between refuelling events—i.e. the fuel characteristics may remain constant throughout a flight. In such examples, fuel properties do not change during a flight, but external conditions (e.g weather, altitude) and internal conditions (e.g. thrust demand) do, and changes may be made (i) initially when the fuel characteristics are first determined or processed, and/or (ii) based on what is appropriate for that fuel given condition changes.

In other examples, the aircraft 1 may have a plurality of fuel tanks 50, 53 which contain fuels of different compositions, and the propulsion system 2 may comprise an adjustable fuel delivery system, allowing a selection to be made of which tank(s) 50, 53, and therefore what fuel/fuel blend, to use. In such examples, the fuel characteristics may vary over the course of a flight, and a specific fuel or fuel blend may be selected to improve operation at certain flight stages or in certain external conditions. In such examples, changes to propulsion system control may also be made when the fuel changes e.g. due to a determination that one fuel is nearly running out, or to the selection of a different fuel or fuel blend. (It will be appreciated that, in general, a fuel system may be arranged to never let a tank 50, 53 run completely dry, as that could lead to an engine 10 flaming-out—however, a tank may be allowed to be fully emptied if its fuel is being provided as part of a blend; one or more other fuels of the blend may have their flow rate increased to ensure the engine 10 is never short of fuel.) A change of fuel may therefore be a response to a propulsion system control change, and may provoke one or more further propulsion system control changes.

In examples in which direct detection is used for one or more fuel characteristics, or in which the fuel characteristics are calculated from detected parameters, the detection may be performed in the or each tank 50, 53 (and fuel characteristics for a resultant fuel blend from different tanks may then be calculated where appropriate), and/or on approach to engine 10, e.g. in a pipe containing a blended mix from multiple tanks. In some examples, the detection may be performed on the fuel immediately before entering engine 10, or more specifically the combustor 16, to ensure that the correct fuel/fuel blend is identified and that the data are as up-to-date as possible (near real-time).

Once one or more fuel characteristics have been determined for fuel currently being provided to the gas turbine engine 10, control of the propulsion system 2 may be adjusted based on the determined fuel characteristics.

Additional data may be used in conjunction with the determined fuel characteristics to adjust control of the propulsion system 2. For example, data of current conditions around the aircraft 1 may be received (either from a provider, such as a third-party weather-monitoring company, or from on-board detectors). These received data (e.g. weather data, temperature, humidity, presence of a contrail, etc.) may be used to make or influence changes in propulsion system control. Instead of, or as well as, using "live" or near-live weather data, forecast weather data for the aircraft's route may also be used to estimate current conditions.

Examples of propulsion system changes which may be made based on the fuel characteristics include any or all of the control examples described above, such as adjusting VIGV scheduling.

A propulsion system 2 for an aircraft 1 may therefore comprise a fuel composition determination module 210 arranged to determine 2052 one or more fuel characteristics of the fuel arranged to be provided to the gas turbine engine 10; and an electronic engine controller 42 arranged to issue propulsion system control commands based on the determined fuel characteristics. The fuel composition tracker 202 of the example shown may be part of, or have access to, an electronic engine controller (EEC) 42 arranged to issue propulsion system control commands based on the fuel characteristics. In some cases, the EEC may issue recommendations for pilot approval (or approval by another authority), and may then issue a propulsion system control command subject to that approval. It will be appreciated that an EEC 42 may be provided for each gas turbine engine 10 of the aircraft 1, and that the role played by the EEC for the fuel composition tracker 202 may be just a small part of the functionality of the EEC. Indeed, the fuel composition tracker 202 may be provided by the EEC, or may comprise an EEC module distinct from the engine's EEC 42 in various implementations. In alternative examples, the fuel composition tracker 202 may not comprise any engine control functionality, and may instead simply supply fuel composition data on demand, to be used as appropriate by another system.

Various different locations and types of fuel composition determination module 210 and associated fuel characteristic sensors may be used depending on when, where, and how, fuel composition is to be determined. For example, as described above with respect to the flight profile control method 2050 shown in FIG. 8.

In some examples, fuel composition may be detected when the aircraft 1 is refuelled. The fuel composition determination module 210a in such examples may be or comprise a fuel composition tracker 202.

The active infinite summing approach described above may therefore be used in conjunction with the flight profile adaptation approach described above, and/or with the in-flight adjustment approach currently being described, or any of the three may be used in isolation. As mentioned above, the flight profile adjustor 212 shown in FIG. 6 may not be present in examples in which the flight profile adaptation approach described above is not implemented.

The fuel composition tracker 202 and fuel composition tracking system 203 may be as described above.

Data from the fuel composition tracker 202 may be used to change the planned flight profile and/or to guide or make in-flight adjustments to the propulsion system 2, based on the one or more fuel characteristics.

A propulsion system 2 for an aircraft 1 may therefore comprise a fuel composition tracker 202, or other fuel composition determination module 210, arranged to record and store fuel composition data, and optionally also to receive the fuel characteristics of the fuel to be added on refuelling, and calculate updated fuel composition data. The fuel composition determination module 210 may be provided as a separate fuel composition tracking unit built into the propulsion system, and/or as software and/or hardware incorporated into the pre-existing aircraft control systems.

Data from the fuel composition determination module 210 may be used to adjust control of the propulsion system 2, based on the one or more fuel characteristics.

A propulsion system controller 42, also referred to as an electronic engine controller 42, may be used to adjust control of the propulsion system 2 based on the one or more fuel characteristics of the fuel, using data provided by the fuel composition determination module 210 and optionally other data. It will be appreciated that the propulsion system controller 42 may control propulsion system elements which may or may not be considered as components of the engine 10 itself, such as one or more flight control surfaces. The term "electronic engine controller" (EEC) 42 as used synonymously herein is not intended to be limited in that sense. The propulsion system controller 42 may be provided as a separate propulsion system controlling unit 42 built into the propulsion system 2, as a part of the fuel composition determination module 210, and/or as software and/or hardware incorporated into the pre-existing aircraft control systems. Fuel composition tracking abilities may be provided as part of the same unit or package.

The propulsion system controller 42 may make changes to the propulsion system 2 directly or may provide a notification or suggestion to the pilot (or other authority) regarding the change, for approval. A notification or suggestion may be provided to a pilot on a cockpit display of the aircraft, and/or sent to a separate device such as a portable tablet or other computing device. In some examples, the same propulsion system controller 42 may automatically make some changes, and request others, depending on the nature of the change. In particular, as mentioned above, changes which are "transparent" to the pilot—such as internal changes within engine flows which do not affect engine power output and would not be noticed by a pilot—may be made automatically, whereas any changes which the pilot would notice may be notified to the pilot (i.e. a notification appearing that the change will happen unless the pilot directs otherwise) or suggested to the pilot (i.e. the change will not happen without positive input from the pilot).

Figure 9:
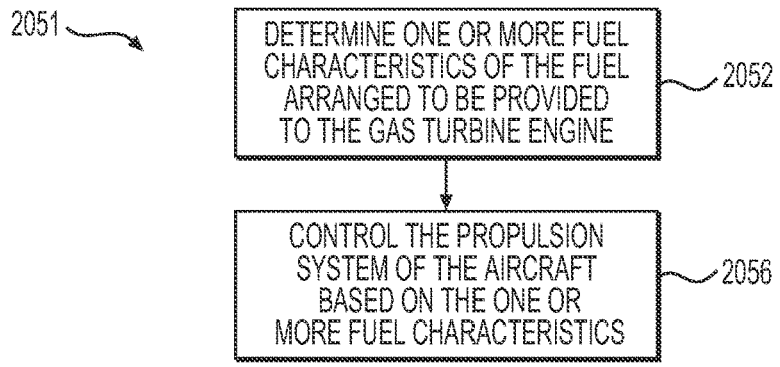
FIG. 9 is a schematic representation of another aircraft operation method.

The method 2051 performed is illustrated in FIG. 9. At step 2052, one or more fuel characteristics of the fuel arranged to be provided to the gas turbine engine 10 are determined. The fuel characteristics may be or comprise any of those listed above, and may be selected based on which characteristics have the most significant effects on optimal propulsion system control. At step 2056, the propulsion system 2 of the aircraft 1 is controlled based on the one or more fuel characteristics. The control actions taken may be or comprise any of those listed above.

A propulsion system controller 42 may therefore be used to initiate and/or effect the control of the propulsion system 2. In some examples, the propulsion system controller 42 may make a change automatically, for example by providing a command to cause a change in position of one or more variable inlet guide vanes of the aircraft propulsion system 2 in response to an assessment of fuel characteristics (and optionally of other conditions). In other examples, the propulsion system controller 42 may not automatically send instructions to control the propulsion system 2, but may instead provide a proposed change in propulsion system control for approval, based on one or more fuel characteristics.

The inventors also appreciated that, as different fuels can have different properties whilst still conforming to the standards, knowledge of the fuel(s) available to an aircraft 1 can allow more efficient, tailored, control of the propulsion system 2. For example, changing to a fuel with a higher calorific value may allow for a constant rate of fuel supply to the combustor 16 whilst still providing a higher power output. Selection of a specific fuel based on the intended or current aircraft operations can therefore be used as a tool to improve aircraft performance. In particular, calorific value of a fuel may be considered.

Below, this approach is described with respect to two aircraft fuel source arrangements different from that shown in FIG. 4. It will be appreciated that any of the approaches described herein may be used with any suitable fuel supply system, and that the examples pictured and described in detail are not intended to be limiting.

Figure 10:
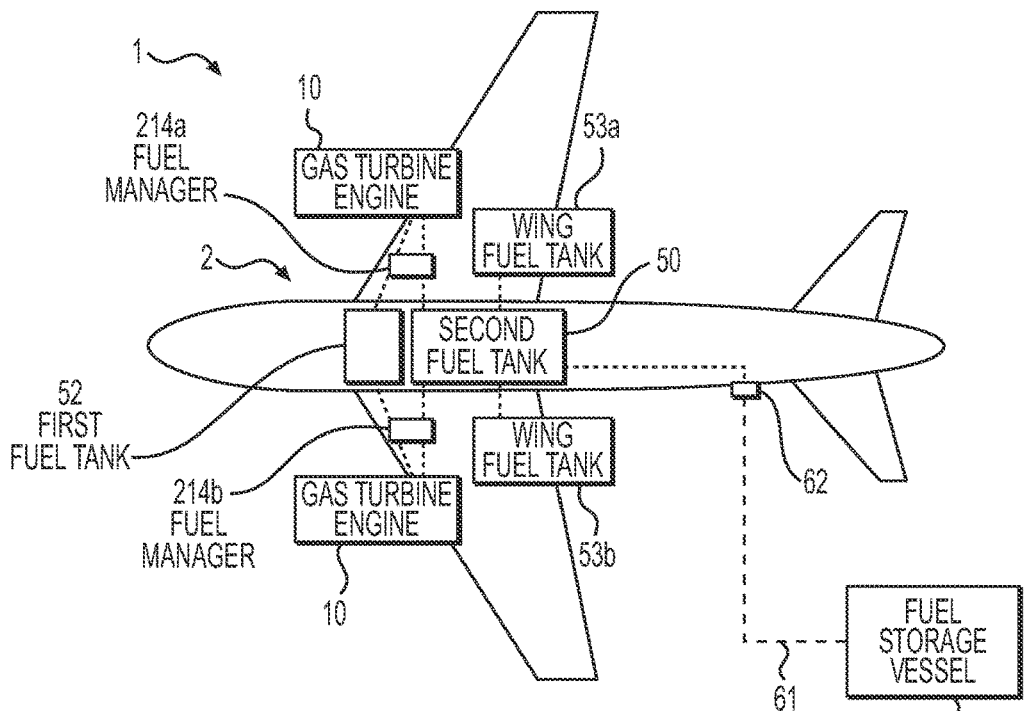
FIG. 10 is a schematic view of an aircraft including a fuel manager.
Figure 14:
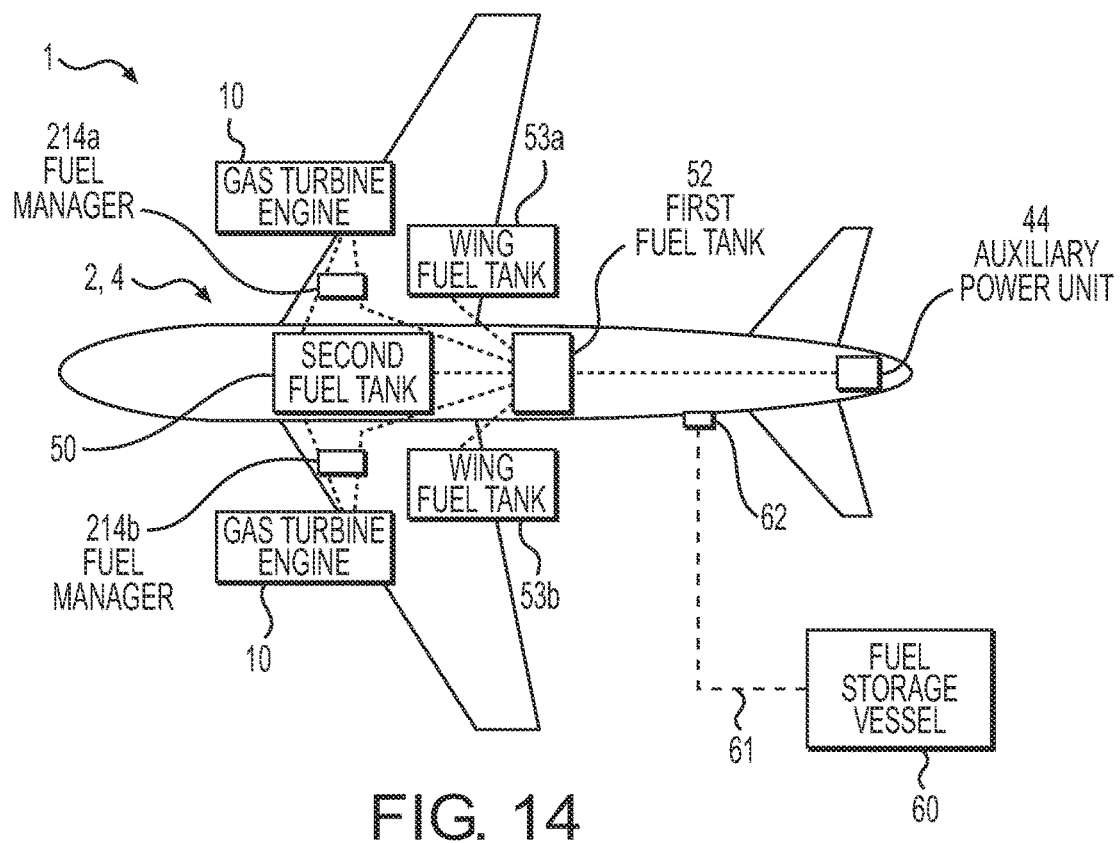
FIG. 14 is a schematic view of an aircraft with a different tank arrangement from that shown in FIG. 4, FIG. 7, or FIG. 10, including a fuel manager and a trim tank.

In particular, as depicted in FIG. 10 and FIG. 14, an aircraft 1 may comprise multiple fuel tanks 50, 52, 53; for example, a first fuel tank 52 and a second, larger, fuel tank 50, each located in the aircraft fuselage, and a smaller fuel tank 53a, 53b located in each wing. In other examples, only two fuel tanks 50, 52, or more fuel tanks, may be provided. Fuel tank sizes, shapes, and locations may vary; for example, all fuel may be stored in tanks 53 in the wings.

FIG. 10 shows an aircraft 1 with a propulsion system 2 comprising two gas turbine engines 10. The gas turbine engines 10 are supplied with fuel from a fuel supply system onboard the aircraft 1. The fuel supply system of the example pictured comprises two fuel sources. Each of the fuel sources is arranged to provide a separate source of fuel i.e. they are fluidly isolated and the first fuel source may contain a first fuel having a different characteristic or characteristics from a second fuel contained in the second fuel source. For example, the fuels may have different compositions and/or different origins, e.g. one being a fossil-derived fuel such as Jet-A, another being paraffinic SAF, non-paraffinic SAF, a paraffinic SAF with a different composition, or a blend. First and second fuel sources are therefore not fluidly coupled to each other, so as to separate the different fuels (at least under normal running conditions). A fuel source may be a single tank or made up of multiple fluidly interconnected tanks, and may be referred to as a fuel tank even when it in fact comprises multiple interlinked tanks.

In the present example, the first fuel source is the first fuel tank 52. In other examples, the first fuel source may comprise multiple interlinked tanks.

In the present example, the second fuel source comprises a centre fuel tank 50, located primarily in the fuselage of the aircraft and a plurality of wing fuel tanks 53a, 53b, where at least one wing fuel tank is located in the port wing and at least one wing fuel tank is located in the starboard wing for balancing. All of the tanks 50, 53 except the first fuel tank 52 are fluidly interconnected in the example shown in FIG. 10, so forming a single, second, fuel source. Each of the centre fuel tank and the wing fuel tanks may comprise a plurality of fluidly interconnected fuel tanks.

In another example, the wing fuel tanks 53a, 53b may not be fluidly connected to the central tank 50, so forming a separate, third, fuel source. For balancing purposes, one or more fuel tanks in the port wing may be fluidly connected to one or more fuel tanks in the starboard wing as described above. In the example of FIG. 10, however, fluid interconnection between wing fuel tanks 53 and the centre fuel tank 50 of the second fuel source is provided for balancing of the aircraft 1.

The example shown in FIG. 14 is generally similar to that shown in FIG. 10, but the differences are described below.

In the example shown in FIG. 14, the first fuel tank 52 is smaller than the second fuel tank 50. The first fuel tank 52 of this implementation is located further towards the rear of the fuselage. The first fuel tank 52 may therefore be used as a trim tank 52 in flight—it will be appreciated that, as is known in the art, a trim tank 52 can be used to provide control of the centre of gravity in the longitudinal axis of the aircraft 1; the aircraft is "trimmed" by pumping fuel into (or out of) a trim tank. One or more pumps, valves, sensors, controls, and similar may be provided to control the trimming operation. In other implementations, the first fuel tank 52 may not be a trim tank; its connections to other fuel tanks 50, 53, may differ or not be present in such other implementations. A trim tank 52 is therefore fluidly connected to at least one other fuel tank 50, 53 of an aircraft 1 so as to allow trimming to be performed in flight. This is a controllable fluid connection, so the first tank 52 can be isolated from the other tanks 50, 53 and used as a separate fuel source when desired.

In addition to the propulsion system 2 described with respect to FIG. 10, a power system 4 of the implementation shown in FIG. 14 includes an Auxiliary Power Unit (APU) 44. The APU 44 is a gas turbine engine smaller than those 10 on the wings of the aircraft 1, and is arranged to provide electrical power to systems of the aircraft 1; for example, lighting, heating, air conditioning and/or similar. The APU 44 may be, for example, an APU in Honeywell's 331 Series, such as the HGT1700 auxiliary power unit (APU). In some implementations, the APU 44 may be certified for in-flight use; in other implementations, it may be certified for ground use only. An aircraft APU 44 is generally arranged to be started using one or more aircraft batteries so as to provide electrical power as well as optionally bleed air for air conditioning and for engine start. The APU 44 of the implementation shown is located towards the rear of the fuselage, and is not arranged to provide any propulsive power to the aircraft 1. In alternative implementations, the APU may be differently located (e.g. within a nacelle 21 of the aircraft 1), and/or may provide some propulsive power.

In the example shown in FIG. 14, the first fuel tank 52 is arranged to supply fuel to the APU 44. In this example, the first fuel tank 52 is also arranged to supply fuel directly to the main gas turbine engines 10, although these connections may not be present in some implementations, or, alternatively, the first fuel tank 52 may be arranged to supply fuel directly to the main gas turbine engines 10 and not to the APU 44 in some implementations.

In alternative implementations, the first fuel tank 52 may be a dedicated APU fuel tank, and may not be fluidly interconnected to the main gas turbine engines 10, nor to any other fuel tank. In some such examples, a fuel manager 214 as described below may not be used for the APU fuel supply.

In various implementations, a plurality of fuel line connection ports 62 may be provided, optionally to facilitate supply of different fuels to different tanks/fuel sources 50, 52, 53. Alternatively or additionally, a fuel supply management system may direct incoming fuel from the same port 62 to different tanks, as appropriate. In particular, in the examples being described, the first tank 52 can be fuelled directly from a fuel supply rather than having to be filled by transfer from another fuel tank 50, 53 of the aircraft 1. In FIG. 14, internal fuel lines from the port(s) 62 to the tanks are not shown, for clarity. In FIG. 10, one internal fuel line is shown (to the larger tank 50); it will be appreciated that at least a second fuel line to the first fuel tank 52 would generally also be provided but that is not shown for clarity.

In examples of the present invention, the aircraft 1 has a plurality of fuel tanks 50, 52, 53, and in particular, at least two different fuel sources and optionally more. At least two of the fuel tanks are arranged to contain different fuels—i.e. fuels with at least one difference in the fuel characteristics—and in particular, to contain fuels with different calorific values.

One or more fuel characteristics of each fuel stored onboard the aircraft 1 may be determined. The determined fuel characteristics may include one or more of the example fuel characteristics listed above.

The determination may be performed in many different ways. For example:
- a barcode of a fuel to be added to a fuel tank 50, 52, 53 of the aircraft 1 may be scanned to read data of the fuel, or a tracer substance (e.g. a dye) identified and fuel properties looked up based on that tracer;
- data may be manually entered, or transmitted to the aircraft 1;
- a fuel sample may be extracted for ground-side analysis prior to take-off;
- fuel properties may be inferred from measurements of the propulsion system activity during one or more periods of aircraft operation, e.g. engine warm-up, taxi, take-off, climb and/or cruise; and/or
- one or more fuel properties may be detected in-flight, for example using in-line sensors and/or other measurements, and any of the detection approaches described above.

The fuel characteristics may therefore be chemically and/or physically detected, or otherwise determined, by any suitable means described herein. In some examples, combinations of these techniques may be used to determine and/or verify one or more fuel characteristics.

Calorific values (also referred to as heating values) of the fuels may be directly determined—for example by measuring or inferring the energy released when a certain volume or mass of the fuel is combusted in the gas turbine engine 10—or calculated from other fuel parameters; e.g. looking at the hydrocarbon distribution of the fuel and the calorific value of each constituent hydrocarbon type. Alternatively, or additionally so as to provide verification, the calorific value may be determined using external data, such as a look-up table for a tracer substance in the fuel, or data encoded in a barcode associated with the fuel.

In some examples, every fuel tank 50, 52, 53 of the aircraft 1 may be arranged to contain a fuel with a different calorific value; i.e. every fuel tank may be a separate fuel source.

As used herein, the term "calorific value" denotes the lower heating value (also known as net calorific value) of the fuel, unless otherwise specified. The net calorific value is defined as the amount of heat released by combusting a specified quantity of the fuel, generally in units of J/kg, assuming that the latent heat of vaporisation of water in the reaction products is not recovered (i.e. that produced water remains as water vapour after combustion).

In some examples, two or more tanks 50, 52 of the aircraft may be arranged to contain fuels with a different type or proportion of a sustainable aviation fuel, the fuels having different calorific values.

The propulsion system 2 comprises an adjustable fuel delivery system 220, allowing a selection to be made of which source(s)/tank(s) 50, 52, 53, and therefore what fuel or fuel blend, to use. In such examples, the fuel characteristics may vary over the course of a flight, and a specific fuel or fuel blend may be selected to improve operation at certain flight stages or in certain external conditions.

A first fuel tank 52 of the plurality of fuel tanks 50, 52, 53 may have a higher proportion of sustainable aviation fuel (SAF) than a second fuel tank 50 of the plurality of fuel tanks and may have a higher calorific value than a fossil-based fuel, or SAF-fossil blend, in another, second, fuel tank. More fuel from the second tank 50 may be used at cruise and more fuel from the first tank 52 may be used at operating points with higher power demands (e.g. take-off and climb).

In other examples, the first fuel tank 52 may contain a fuel with a lower calorific value than that in another tank 50. More fuel from the first tank 52 may be used at cruise and more fuel from the second tank 50 may be used at operating points with higher power demands (e.g. take-off and climb).

One fuel tank 52 of the plurality of fuel tanks may be arranged to contain only a fuel which is a sustainable aviation fuel (SAF)—that tank may contain 100% pure SAF, or SAF with one or more additives, but does not contain any fossil-based fuel. (As used herein, "SAF" means a pure sustainable aviation fuel, containing no fuel of a fossil/petroleum origin (but optionally one or more additives, e.g. an icing inhibitor); the term "SAF blend" or "blended fuel" may be used for a mixture including both SAF and fuel of a petroleum origin.) The SAF in that tank 52 may be selected such that the propulsion system 2 can be run on that fuel alone (for example, for ground operations, or in case of an emergency in flight, or if/when fuel regulations change such that flight on SAF fuel alone is generally permitted).

In such examples, the fuel tank 52 containing the sustainable aviation fuel only may therefore be arranged to be used to power the aircraft 1 when the aircraft is performing operations on the ground. Optionally, all fuel, or at least the majority of fuel, used for ground operations may be arranged to be taken from the fuel tank 52 containing the sustainable aviation fuel, for example to meet airport requirements for emissions and/or use of SAF. A SAF blend fuel with a high % SAF may be used in place of SAF in other implementations.

It will be appreciated that use of SAF (either alone or in a mixed fuel) may provide a significant reduction in non-volatile particulate matter (nvPM) emissions at idle conditions—the percentage reduction may be greater than 90% at those conditions in some cases. It is thought that the percentage reduction in nvPM for SAF use is greater at idle than at high power demands, as soot (nvPM) creation is linked more closely to the fuel aromatic content at those low power conditions compared to at higher power demands where other soot formation mechanisms come into play—SAFs generally have a lower aromatic content than petroleum-derived aviation fuels. As such, if a total amount of the SAF is limited, using the SAF for ground-based operations/operations around the airport instead of elsewhere in a flight cycle may provide an increased benefit in reduction of nvPM production. Additionally, airport air quality may be improved. Similarly, in-flight, a larger benefit from using SAF may be found if the SAF is used for lower-power parts of the flight envelope.

For the same reasons, SAF may be selected to be used in an auxiliary power unit (APU) of the aircraft 1 at the gate of an airport.

However, SAFs often have a higher calorific value than traditional jet fuels—in such cases, different control of fuel input to the gas turbine engine 10 may therefore be used for ground-based operations (where reductions in nvPM may be prioritised) as compared to in flight (where matching calorific value to thrust may be prioritised), if only a limited amount of SAF is available. In scenarios in which fuels with similar nvPM properties but different calorific values are available onboard an aircraft 1, the same control may be used throughout operation; both for ground-based operations and in flight.

In examples with a SAF-only tank 52, that fuel tank 52 may be smaller than the one or more other fuel tanks 50, 53, for example, the first fuel tank 52 may represent 3% to 20%, and optionally 5% to 10%, of the total available tank volume of the aircraft 1. Optionally, that tank 52 may be arranged to be used exclusively for ground-based operations of the aircraft 1. A selection between the other tanks 50, 53 based on calorific value may then be made in flight based on engine thrust.

In implementations such as that shown in FIG. 14, in which a trim tank 52 is present on the aircraft 1 and is used as the first fuel tank 52, fuel would be drawn from the trim tank 52, which therefore decreases in mass due to the loss of fuel, during ground-based operations, for example on-stand operations, warm-up, and optionally during one or more of taxi, and take-off roll. In particular, if the trim tank 52 is filled with SAF (or a high % SAF mixed fuel), the air quality advantages obtained by using that SAF from the trim tank 52 for the APU 44 while on the stand may be obtained, and that SAF may additionally be used for the main gas turbine engines 10 during warm-up, taxi, take-off, and possibly some of climb (optionally as a mix with another fuel), until the trim-tank 52 is empty. In some cases, the amount of fuel in the trim tank 52 may be selected such that the trim tank 52 is at least substantially empty by take-off, so that it may get (partially) refilled during climb, so as to enable its use for trimming the aircraft 1 even during climb. In other examples, it may be used for trimming the aircraft 1 only later in the flight. Fuel from a different fuel source 50, 53 may be used thereafter. Such implementations may be of particular utility when the aircraft 1 is conducting missions towards the limit of its payload-range capability; allowing all fuel tanks to be filled to their fullest capacity initially whilst still providing trim tank capacity promptly after take-off/before the trim tank 52 is usually used.

As such, by the time the aircraft 1 gets airborne, the first fuel tank 52 would be relatively light, if not completely empty, and would not affect centre of mass significantly. The first fuel tank 52 is therefore available for normal use as a trim tank 52 for at least the cruise part of the flight—fuel from one or more of the other fuel sources 50, 53 can be pumped into it when ready to reduce drag during cruise, and optionally also during climb (after at least substantially emptying the first fuel tank 52 at the latest part way into climb).

The amount of fuel initially in the trim tank 52 may be selected to enable that fuel to be fully used up well before the aircraft 1 reaches its cruise altitude. More particularly, in such implementations, the amount of fuel supplied to the first fuel tank 52 on filling may be calculated so as to be at least substantially used up by the time the aircraft 1 takes off, and optionally more specifically by the time the aircraft rotates (rotation being what happens towards the end of the take-off roll when the nose wheel of the aircraft 1 leaves the ground, but the main landing gear is still on the ground. In the moments following rotation, the aircraft 1 gains speed and then the main landing gear also leaves the ground). The fuel in the first fuel tank 52 of such examples may be selected based on its air quality and pollution effects, and may or may not have a lower calorific value than the fuel(s) in other tanks 50, 53.

In examples in which the first fuel tank 52 is used as a trim tank 52, an onboard fuel manager 214 may be arranged to detect the fuel level in the first fuel tank 52 and automatically switch supply to a different tank (irrespective of how much additional nvPM may be caused) if it detects imminent running-dry of that tank 52, to avoid any fuel supply interruption to the engine 10, 44. It will be appreciated that having a relatively small amount of fuel remaining in the trim tank 52 would not prevent it from being used as such, and/or that the fuel manager 214 may be arranged to pump fuel out of the trim tank 52 and into a different tank before the take-off run commences, optionally following a negative result to a check that the trim tank 52 is sufficiently empty for the fore/aft centre of gravity to be within acceptable limits.

In some implementations, the fuel manager 214 may be arranged to automatically switch from the first fuel tank 52 to another, optionally larger, tank 50, 53 before commencing the take-off roll, to eliminate the possibility of the first tank 52 running dry during the take-off roll and/or climb-out.

In some implementations, the fuel manager 214 may be arranged to request or enforce more engine idle time before commencing a take-off run to ensure that the trim tank 52 is sufficiently empty for use, if trimming of the aircraft 1 is expected to be needed during the take-off run and/or if no spare capacity is available for fuel to be pumped out of the trim tank 52.

In examples in which detection is used to determine one or more fuel characteristics, the detection may be performed in each tank 50, 52, 53 (or in one tank of each fuel source), and fuel characteristics for a resultant fuel blend from different tanks may then be calculated where appropriate based on blend ratios. Alternatively or additionally, the detection may be performed on approach to the engine 10, e.g. in a pipe/fuel line which may contain a blended mix from multiple tanks.

Where data are collected for a fuel blend, e.g. on approach to the engine 10, data may be recorded as the blend is changed (by taking more or less fuel from a given tank 50, 52) so as to determine the composition of fuel in each tank 50, 52, 53 individually. This determination may allow fuel selection or blend to be tailored in-flight, e.g. using different fuels as appropriate for different parts of a flight envelope, even when fuel composition is not known on take-off. Further, in some implementations such a determination may be performed during engine warm-up, and/or in the early stages of taxi, so that fuel selection for the rest of the taxiing may be adjusted as appropriate, for example selecting a fuel or fuel blend with maximum nvPM benefits whilst still at the airport.

In some examples, detection may be performed on the fuel immediately before entering the engine 10/combustor 16, optionally to ensure that the correct fuel/fuel blend is identified (e.g. as a check of the intended composition if this is already known) and that the data on fuel being burned are as up-to-date as possible (near real-time).

Once the calorific value of each fuel available for supply to the gas turbine engine 10 has been determined, by any suitable method, a single fuel (from a single tank) or fuel blend (from multiple tanks) may be selected and provided to the gas turbine engine 10, based on a thrust demand of the gas turbine engine 10. In particular, a fuel (single fuel or blend) with a lower calorific value may be supplied to the gas turbine engine 10 at lower thrust demand. Correspondingly, a fuel (single fuel or blend) with a higher calorific value may be supplied to the gas turbine engine 10 at higher thrust demand. The fuel control based on calorific value may be performed in flight only in some scenarios, allowing fuel supply for ground-based operations to be controlled differently (e.g. prioritising reduction of nvPM generation over matching calorific value to power demand).

It will be appreciated that thrust demand may be determined using any one or more approaches known in the art, for example based on fuel flow rate and/or power lever angle in the cockpit, or one or more other pilot settings, and optionally taking account of outside air density, or a proxy for it such as altitude, ambient temperature, and/or pressure. Use of fuel flow rate alone may be insufficient due to differences in fuel flow ranges at altitude as compared to on the ground.

The variation in calorific value of the fuel corresponding to thrust demand may facilitate maintenance of a more constant fuel flow rate, and/or more even fuel pump and spill operation in flight. In general, the fuel mass flow rate varies widely between different parts of the flight for an aircraft 1, so differences in fuel calorific value are not big enough to compensate for differences in fuel energy flow requirements between climb and initial cruise, for example. However, during a level cruise segment where the aircraft 1 is burning off fuel at a constant altitude, the thrust requirement may decline slowly over a sustained period, and fuel flow calorific value adjustments may allow an approximately constant flow to be maintained. A substantially constant fuel flow rate may therefore be maintained in certain portions of aircraft operation by implementing the approach disclosed herein. Further, maxima in fuel flow rate may be reduced, and/or minima in fuel flow rate may be increased, by choosing a fuel with a suitable calorific value at the corresponding points of aircraft operation. The "more constant fuel flow rate" may therefore refer to a decrease in the maximum spread of fuel flow rates across an entire engine operation envelope/flight envelope.

It will be appreciated that pump speed is generally linked to shaft speed in some aircraft 1, with a spill ratio being adjusted as required for a given speed, such that fuel flow rate to the combustor 16 is controlled by a fuel delivery system 220 (e.g. comprising a hydro-mechanical unit, HMU) comprising multiple components, rather than by a fuel pump alone. This more even operation may be beneficial in terms of providing a suitable flow of fuel through the system, for example for lubrication, for fueldraulics, and for heat transfer, even at very low power demands. Use of a lower calorific value fuel in the engine 10 at lower power demands can assist with heat management, as the higher flow rate of fuel passing through the engine provides more of a heat transfer medium. Further, it can be difficult to run large engines 10 smoothly at low idle thrust using standard fuels—being able to switch to a fuel with a lower calorific value could therefore improve performance at low idle thrust.

Figure 11:
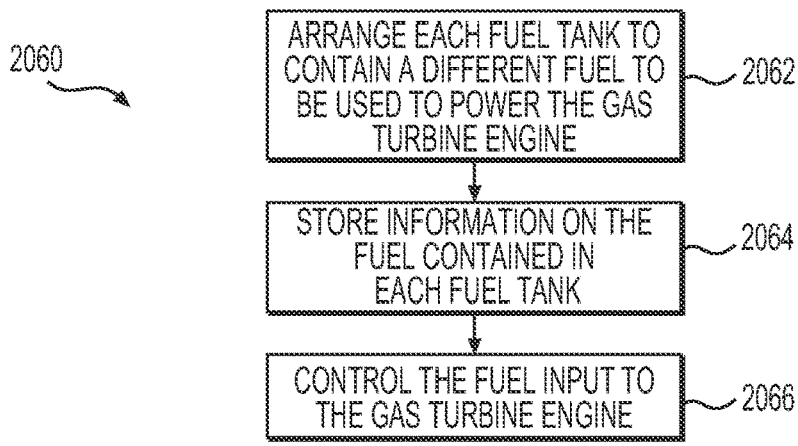
FIG. 11 is a schematic representation of another aircraft operation method.

A method 2060 of operating an aircraft 1 comprising a gas turbine engine 10 and a plurality of fuel tanks 50, 52, 53 arranged to store fuel to power the gas turbine engine 10 is shown in FIG. 11.

The method 2060 comprises arranging 2062 each fuel source/tank 50, 52 of the plurality of fuel tanks to contain a different fuel to be used to power the gas turbine engine 10, wherein the fuels have different calorific values. In some examples, one or more of the fuel tanks 50, 52 may be part of a separate set of interlinked fuel tanks. In other examples, each fuel tank 50, 52 may be a stand-alone, single-tank, fuel source.

The method 2060 further comprises storing 2064 information on the fuel contained in each fuel tank 50, 52, optionally in memory of an on-board fuel manager 214.

The method 2060 further comprises controlling 2066 the fuel input to the gas turbine engine 10 by selection of a specific fuel or fuel combination from one or more of the plurality of fuel tanks 50, 52. The control 2066 may be performed only in flight, or throughout aircraft operation. The selection is made based on thrust demand of the gas turbine engine 10 such that a fuel with a lower calorific value is supplied to the gas turbine engine 10 at lower thrust demand (e.g. ground operations (if implemented on the ground), descent, cruise), and a fuel with a higher calorific value is supplied to the gas turbine engine 10 at higher thrust demand (e.g. climb).

Even for an example with only two separate fuel sources 50, 52, a range of different fuel calorific values may be provided by dynamically blending the two fuels to different levels, depending on thrust demand. In some arrangements, the method 2060 comprises switching between two, three, four, or five fuels, and/or pre-set blends, with determined calorific values, depending on thrust demand. In other arrangements, the blend may be changed as a function of thrust demand, optionally continuously (within limits of precision of the fuel pump and/or other flow controllers).

Additional data may be used in conjunction with the determined fuel characteristics to adjust control of the propulsion system 2. For example, the method may comprise receiving data of current conditions around the aircraft 1 (either from a provider, such as a third-party weather-monitoring company, or from on-board detectors). These received data (e.g. weather data, temperature, humidity, presence of a contrail, etc.) may be used to make or influence changes in the composition of fuel supplied to the gas turbine engine 10. Instead of, or as well as, using "live" or near-live weather data, forecast weather data for the aircraft's route may also be used to estimate current conditions.

A propulsion system 2 for an aircraft 1 may therefore comprise a fuel manager 214 arranged to store information on the fuel contained in each fuel tank 50, 52 and to control fuel input to the main gas turbine engine(s) 10, and optionally also to an APU 44, in operation. The fuel manager 214 may be provided as part of a fuel delivery system 220 arranged to allow control and adjustment of the fuel supplied to the gas turbine engine 10.

Figure 12:
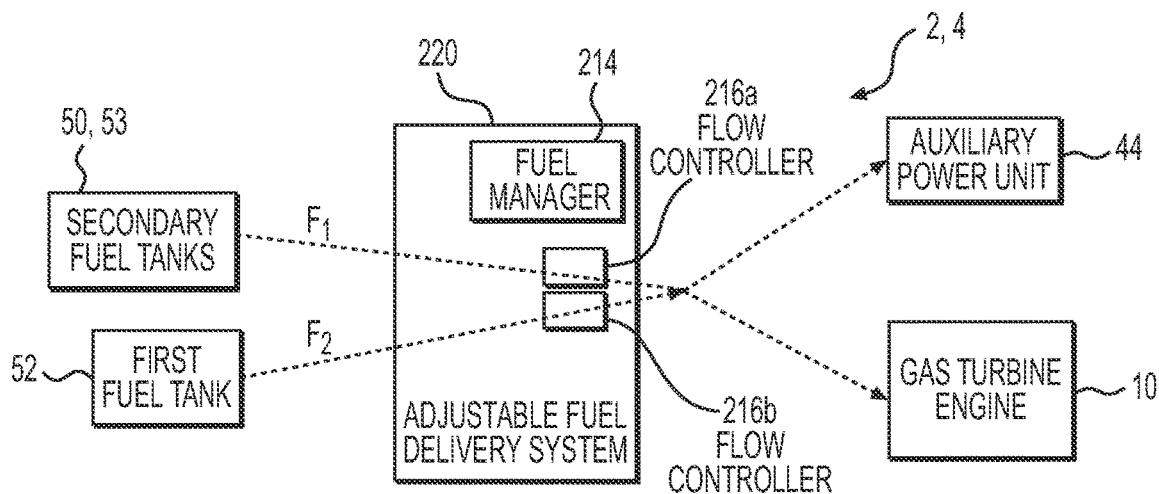
FIG. 12 is a schematic view of an aircraft fuel delivery system, in context with a fuel tank and gas turbine engine.

The fuel delivery system 220, as shown in FIG. 12, may comprise one or more flow controllers 216, such as valves and pumps, arranged to be controlled by the fuel manager 214 so as to control fuel input to the main gas turbine engine(s) 10, and optionally also to an APU 44. For example, one flow controller 216a, 216b may be provided between each fuel source and each engine 10. Such arrangements may allow different fuels to be supplied to different engines 10 of the same aircraft propulsion system 2.

Optionally, the fuel manager 214 may additionally receive other data (in addition to fuel characteristic data), and use that other data and the fuel characteristic data to determine a desired fuel or fuel blend for the gas turbine engine 10. The fuel manager 214 may be provided as a separate fuel management unit 214 built into the propulsion system 2, and/or as software and/or hardware incorporated into the pre-existing aircraft control systems (e.g. into the EEC 42). In some examples, the fuel composition data may be stored separately from the circuitry performing the fuel supply management and retrieved when required—wherever the data are stored, that storage can be thought of as a part of the fuel manager 214, whether or not it is integral therewith or indeed physically connected thereto in any way.

The broader term "power system" 4 may be used for the propulsion system 2 to ensure that implementations in which the fuel is additionally or alternatively supplied to an APU 44 are captured, as propulsive power may not always be provided by such power systems 4, e.g. while performing at-gate operations whilst the aircraft 1 is stationary (it will also be appreciated that the main gas turbine engines 10 can also be used to provide non-propulsive power in many implementations).

The fuel manager 214 may be arranged to select a specific fuel or fuel combination from one or more of the plurality of fuel tanks 50, 52, 53 based on thrust demand of the gas turbine engine 10. In particular, a fuel with a lower calorific value is supplied to the gas turbine engine 10 at lower thrust demand, and vice versa. A fuel with a higher calorific value may therefore be used at high-power stages of the flight envelope, such as during take-off. Calorific value of the fuel may be adjusted linearly with a % increase or decrease in thrust demand in some scenarios, within an available range.

The fuel manager 214 may be arranged such that a fuel with a lower calorific value is supplied to the gas turbine engine 10 at cruise as compared to that supplied during climb. Optionally, a fuel with a still lower calorific value may be supplied to the gas turbine engine 10 at ground idle or low idle—this same fuel may also be supplied to the APU 44 in some implementations.

It will be appreciated that the term "low idle" is a generic term generally used for the idle setting for either ground or flight idle when the engine is operating to one of its minimum limiters (e.g. minimum speed, pressure, and/or temperature limits), set within the EEC 42, with the throttle lever position being in the idle detent position.

The idle power level in flight can vary significantly depending on factors such as altitude, power offtake, customer bleed, and anti-icing demands; the term "low idle" therefore covers a range of power/thrust demands.

Idle operation whilst the aircraft 1 is operating on the ground is referred to as 'ground idle' and idle operation whilst the aircraft 1 is operating in flight is referred to 'flight idle'.

High idle is a more specific term, referring to conditions where the aircraft 1 is in an approach landing configuration and idle is raised above flight low idle for the purposes of achieving adequate thrust response if required for a go-around. Whilst the throttle remains in the idle detent condition, there is an increased thrust level, and high idle can only apply in flight (not for operations on the ground). In some implementations, a fuel with a higher calorific value may be supplied to the gas turbine engine 10 at high idle than at low idle, and a fuel with a still higher calorific value may be supplied when the thrust demand rises above that for high idle.

The fuel manager 214 may make changes to the fuel supply directly, or may provide a suggestion or notification to the pilot regarding the change, for approval (e.g. as described above for the propulsion system controller 42, noting that the fuel manager 214 may be a part of, or in communication with, the propulsion system controller 42). In some examples, the same fuel manager 214 may automatically make some changes, and request others, depending on the nature of the change.

In some examples, an aircraft 1 may be modified to perform the method 2060 described above, optionally by installing an adjustable fuel delivery system 220.

Figure 13:
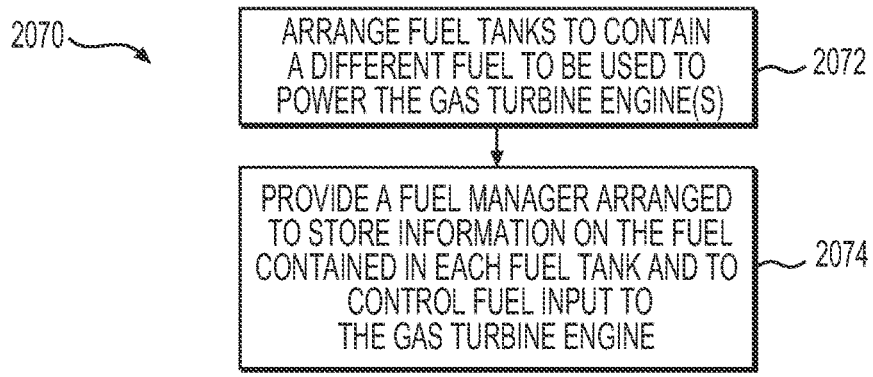
FIG. 13 is a schematic representation of an aircraft modification method.

A method 2070 of modifying an aircraft 1 in such a way is shown in FIG. 13. The original aircraft 1 comprises a gas turbine engine 10, which, in the example being described, comprises an engine core 11 comprising a turbine 19, a compressor 14, and a core shaft 26 connecting the turbine to the compressor. The aircraft 1 also comprises a plurality of fuel tanks 50, 52 and a fan 23 located upstream of the engine core, the fan comprising a plurality of fan blades and being arranged to be driven by an output from the core shaft. The aircraft 1 may also comprise an APU 44.

The method 2070 comprises arranging 2072 each fuel tank 50, 52, 53 (or at least two fuel tanks of a plurality of fuel tanks) to contain a different fuel to be used to power the gas turbine engine(s) 10, 44, wherein the fuels have different calorific values.

In some cases, the aircraft 1 may already comprise a plurality of fuel tanks 50, 52, 53 arranged to store fuel to power the gas turbine engine 10; in such examples, the step 2072 of arranging the fuel tanks may simply comprise filling the tanks selectively with different fuels. In cases in which the aircraft 1 previously only had a single fuel tank 50, a new fuel tank 52 may be added so as to provide a plurality of fuel tanks. In cases in which the aircraft 1 previously only had a single fuel source, albeit comprised of multiple tanks, a new fuel tank 52 may be added and/or fuel lines may be adjusted such that the original tanks 50, 53 are no longer all fluidly interconnected, so providing at least two separate fuel sources. The arranging step 2072 may therefore vary depending on the initial aircraft configuration.

The method 2070 further comprises providing 2074 a fuel manager 214 arranged to store information on the fuel contained in each fuel tank 50, 52, 53 and to control fuel input to the gas turbine engine 10. The fuel manager 214 may operate only in flight. In examples in which it operates both in flight and during ground-based operations, the control strategy it employs may differ between flight and ground-based operations in some examples. In other examples, for example where all available fuels have acceptably low nvPM emissions, fuel control based on thrust and calorific value may additionally be performed during ground-based operations.

The storage and control functions may be performed by separate entities or the same entity; it will be appreciated that the fuel manager 214 may therefore be a distributed system or a single unit or module. The step of providing 2074 the fuel manager 214 may comprise or consist of installing software in extant memory, to be executed using extant systems, in some examples. In other examples, a new physical unit or module may be mounted onto the propulsion system 2, optionally including one or more flow controllers 216 and/or replacement fuel line sections as appropriate to achieve the desired fuel flow and mixing control.

The fuel manager 214 is arranged to control fuel input to the gas turbine engine 10 by selection of a specific fuel or fuel combination from one or more of the plurality of fuel tanks 50, 52, 53 based on thrust demand of the gas turbine engine 10 such that a fuel with a lower calorific value is supplied to the gas turbine engine 10 at lower thrust demand, and vice versa. This control may be performed throughout aircraft operation, or only at certain stages (e.g. only in flight, or only during cruise).

The inventors also appreciated that current standards mean that (pure) SAF cannot be used in commercial flight, but SAF could be used for ground-based operations, for example to reduce airport emissions. Similarly, there may be advantages to using such a sustainable aviation fuel for ground-based operations even when it can also be used in flight, for example to maximise environmental benefits from a limited available amount of SAF. Further, if fuels which are not pure SAF but instead have a proportion of SAF are available to the aircraft 1, using the fuel(s) with the highest % SAF for ground-based operations may correspondingly reduce airport emissions and so improve air quality. Re-design of the aircraft's fuel system may therefore allow technical and environmental benefits of SAF to be realised, whether or not the SAF is provided as part of a blend.

If only a relatively small amount of pure SAF or a high-percentage SAF blend is available to an aircraft 1 (the rest of the fuel being either petroleum-based fuel or a lower-percentage SAF blend), the most benefit from that SAF (or high-percentage SAF blend) may therefore be obtained by using that fuel in and around the airport, where power demand is relatively low (noting nvPM generation discussions above).

For the same reasons, this SAF or high % SAF blend, optionally stored in a first fuel tank 52 as described above, may be used in the auxiliary power unit (APU) 44 of the aircraft 1, e.g. at the gate of an airport.

Whilst it will be appreciated that a synthetic fuel could be made to exactly mimic a traditional kerosene fuel, one or more fuel characteristics of SAF stored onboard the aircraft 1 may differ from the fuel characteristics of the one or more other fuels stored onboard the aircraft 1, in other tanks.

The fuel characteristics may include one or more of the fuel characteristics described above, and may be determined using any of the approaches described above, including by any of the example detection techniques listed.

If two or more different SAFs, or two or more different SAF blends with the same % SAF, are available to the aircraft 1, one or more other fuel characteristics—such as the hydrogen to carbon ratio (H/C) of the fuel or level of non-volatile particulate matter (nvPM) emissions on combustion—may be used to select between the two or more fuels with the same % SAF. One or more other parameters likely to influence air quality around an exhaust from the aircraft 1 may also be compared so as to select the fuel likely to provide the best air quality outcomes. Environmental factors (e.g. airport altitude and humidity) may also be considered in this assessment.

Figure 18:
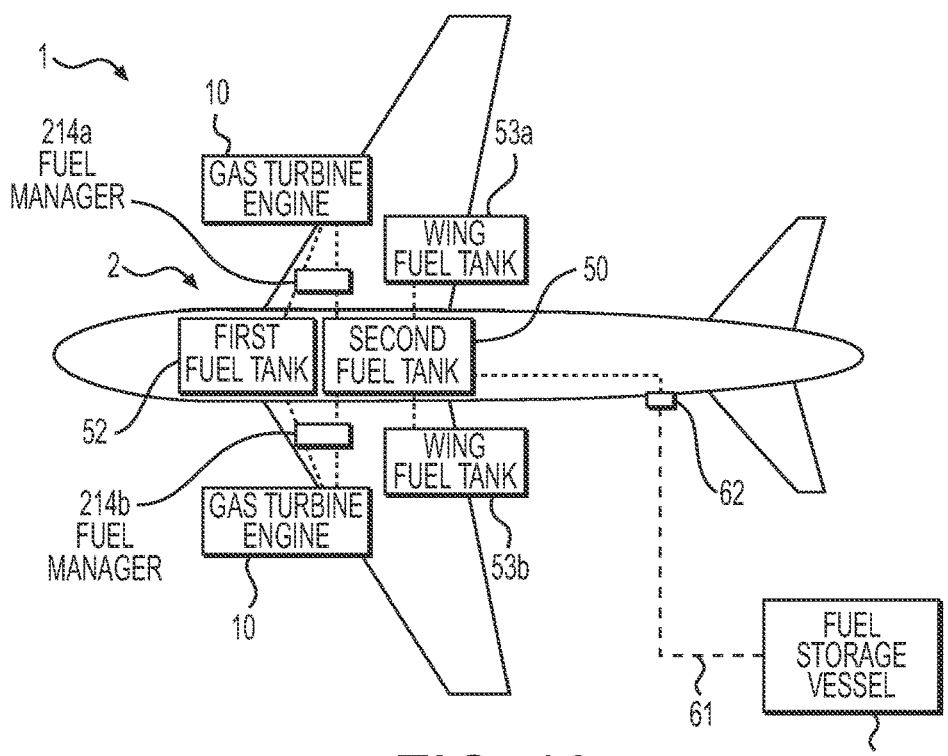
FIG. 18 is a schematic view of an aircraft with a different tank arrangement from that shown in FIG. 14.

In the present examples, described with respect to FIGS. 14 and 18, the first fuel source is the first fuel tank 52. In other examples, the first fuel source may comprise multiple interlinked tanks.

In the example being described, the first fuel tank 52 is arranged to contain only a fuel which is a pure sustainable aviation fuel (SAF), i.e. 100% sustainably sourced and not kerosene derived/of fossil origin. In other examples, multiple fuel tanks of a plurality of fuel tanks may all contain SAF—any one of the subset of fuel tanks containing SAF may therefore be used to supply SAF; it will be appreciated that the example of just one fuel tank 52 containing SAF is described here by way of non-limiting example only.

In other examples, the first fuel tank 52 is arranged to contain a fuel which is a SAF blend with a higher % SAF than that in any other fuel tank 50, 53. In other examples, multiple fuel tanks of a plurality of fuel tanks may all contain a SAF blend with the same % SAF, such that there are multiple first fuel tanks 52—any one of the first fuel tanks may therefore be used to supply fuel for at least the majority of ground-based operations; it will be appreciated that the example of just one first fuel tank 52 is described here by way of non-limiting example only. One or more second fuel tanks 50, 53 contain one or more fuels with a lower % SAF (optionally 0% SAF) and are used for other operations.

The example shown in FIG. 18 is generally similar to that shown in FIG. 14, but the differences are described below. (In FIG. 18, one internal fuel line is shown—to the larger tank 50; it will be appreciated that at least a second fuel line to the first fuel tank 52 would generally also be provided but that is not shown for clarity—similarly, no such fuel lines are shown in FIG. 14 for clarity, but would generally be present.)

In the examples currently being described, the aircraft 1 has a plurality of fuel tanks 50, 52, 53, and in particular, at least two fuel sources/separate tanks 50, 52, and optionally more. Each fuel tank 50, 52 is arranged to store a fuel to be used to power one or more gas turbine engines 10, 44 of the aircraft. One of the fuel tanks 52—referred to as the first fuel tank 52—is arranged to contain only a fuel which is a sustainable aviation fuel (SAF), or to contain a high % SAF fuel blend. In some implementations, such as that shown in FIG. 18, this first fuel tank 52 is arranged to only ever contain the SAF or high % SAF blend, and may always be isolated from the other fuel source(s) 50, 53. In other implementations, such as that shown in FIG. 14, this first fuel tank 52 is arranged to contain the SAF or high % SAF blend initially, and to be fluidly isolated from the other fuel source(s) 50, 53 whilst that fuel is being used (e.g. for ground-based operations), but may then be fluidly connected to one or more other fuel sources 50, 53 in flight (e.g. by opening one or more valves), and may have a different fuel from a different fuel source 50, 53 pumped into it (e.g. to serve as a trim tank 52).

The first fuel tank 52 of such examples is therefore arranged to contain only a fuel which is a sustainable aviation fuel (SAF), or high % SAF blend, at least during ground-based operations. In implementation in which the fuel is 100% SAF, the SAF in that tank 52 may be selected such that the propulsion system 2 can be run on that fuel alone (for example, for ground operations, in case of an emergency in flight, or if fuel regulations change such that flight on 100% SAF is generally permitted), or may be tailored for use in an APU 44 only and not suitable for combustion in a main gas turbine engine 10. The fuel tank 52 containing the sustainable aviation fuel only may therefore be arranged to be used to power the aircraft 1 when the aircraft is performing operations on the ground. Optionally, the first fuel tank 52 may be used to supply SAF to the gas turbine engine 10, but optionally only during ground-based operations. Alternatively, the first fuel tank 52 may be used to supply SAF to the gas turbine engine 10 as part of a blend in flight, or may be arranged to supply SAF only to the APU 44.

In implementations in which the fuel in the first fuel tank(s) 52 is not pure SAF, more flexible use may be made of that fuel in flight even under current regulations at the time of writing.

In some implementations, the first fuel tank 52 may be used to supply fuel to both the main gas turbine engine 10 and the APU 44.

In some of the examples being described, all fuel used for ground operations is sustainable aviation fuel or the highest % SAF blend available, and all fuel used for ground operations is therefore taken from the first fuel tank 52 (in examples with multiple first tanks, any one or more of those tanks may be used). In other examples, most of the fuel used for ground operations is SAF or the highest % SAF blend available, with only small amounts from other sources being used (e.g. less than 10% or less than 5% of the fuel use and/or of the operation time, or using fuel from another source only for initial engine start-up).

It will be appreciated that, if a first fuel tank 52 runs out of fuel, a second fuel tank 50, 53 with the highest % SAF blend amongst the second fuel tanks may be reclassified as a first fuel tank and used for remaining ground-based operations.

A fuel manager 214 may be arranged to control fuel input to the gas turbine engine(s) 10, 44 so as to take only fuel from the one or more first fuel tanks 52 when the aircraft 1 is performing at least the majority of operations on the ground. As used herein, "operations on the ground" generally refers to operations prior to take-off, and may include one or more of:

Start-up of the engine itself;
Heating, lighting, air conditioning and/or other non-propulsive demands, whilst the aircraft 1 is stationary (e.g. at a gate) or moving;
Taxiing of the aircraft 1; and
Initiation of take-off roll, optionally including raising a nose wheel, if appropriate.

The first fuel tank 52 (or another one or more fuel tanks containing SAF or the high % SAF blend, in other examples) may therefore be used to provide some or all of the fuel used by the aircraft power system 4 on-stand (e.g. at a gate), and during warm-up, taxi, and take-off roll.

Beneficially, this may meet airport requirements for emissions and/or use of SAF.

If, once the operations on the ground are complete, there is still some fuel left in one or more of the first fuel tanks 52, optionally it could be reserved for use at the destination airport for further ground operations on landing, including landing roll and taxi-in.

Any leftover fuel in the one or more first fuel tanks 52 may additionally or alternatively be used for the early part of climb (on take-off) and/or the final part of approach (on landing)—i.e. for one or more non-ground parts of the flight that are nonetheless close to the ground and therefore relevant to local air quality and human health. Use of SAF on approach to a destination airport (as opposed to on take-off) may be of particular nvPM benefit, as the power requirement is lower and so the reduction in nvPM achievable by use of SAF higher.

A selection may be made based on the amount of SAF available, the SAF blend types available, and a priority order for SAF usage in the various parts of the aircraft's operations.

The fuel manager 214 may be arranged to control fuel input to the propulsive gas turbine engine(s) 10 in flight by selection of a specific fuel or fuel combination from one or more of the plurality of fuel tanks 50, 52.

The first fuel tank 52 of the plurality of fuel tanks 50, 52, arranged to contain only the fuel with the highest % SAF (which may be SAF) may be smaller than the one or more other fuel tanks 50, 53. For example, the first fuel tank 52 may represent 3% to 20%, and optionally 5% to 10%, of the total available tank volume of the aircraft 1. Optionally, that tank 52 may be arranged to be used exclusively for ground-based operations of the aircraft 1.

Each fuel tank 50, 52, 53 onboard the aircraft 1 may be arranged to contain a fuel of a different type (e.g. petroleum-origin fuel or SAF, or different SAF varieties), and some tanks may contain blended fuels with a proportion of a sustainable aviation fuel mixed with a traditional jet fuel or other petroleum-origin fuel. In some examples, two or more tanks 50, 52 may contain the same fuel, provided that at least two different fuels are available from the fuel tanks on the aircraft 1 overall. In some examples, at least one tank 52 contains SAF—i.e. purely a sustainable aviation fuel, not a blend.

In implementations such as that shown in FIG. 14, in which a trim tank 52 is present on the aircraft 1 and is used as the first fuel tank 52, the approach and benefits relating to SAF use described above may also be obtained.

The propulsion system 2 of the examples being described again comprises an adjustable fuel delivery system 220, allowing a selection to be made of which tank(s) 50, 52, and therefore what fuel or fuel blend, to use. In such examples, the fuel characteristics may vary over the course of a journey (including both flight and the ground-based operations at the beginning and/or end of a journey)—a specific fuel or fuel blend may be selected to improve operation at certain flight stages or in certain external conditions.

In examples in which detection is used for one or more fuel characteristics (either by direct detection, or by inference from detected parameters), e.g. to discover or verify which tank contains the highest % SAF fuel, any of the detection approaches described above may be implemented. In other examples, no detection may be performed and supplied data on fuel composition may be relied upon instead—that data may be simply SAF proportions, e.g. "100% SAF" vs. "Other", or % SAF for each tank, or may include more detailed fuel characteristic information. In other examples, no fuel data at all may be supplied—instead, each tank 50, 52, 53 may be identified as a "SAF-only" tank or a "non-SAF-only" tank, or as a "Highest % SAF" tank or "Other" tank, and the method may rely on the tanks 50, 52, 53 being correctly filled accordingly.

In some examples, calorific values for each available fuel may be calculated or provided, and a fuel or fuel blend supplied based on thrust demand as described above (optionally also considering altitude in flight)—some of the fuel from the first tank 52 may be used alone and/or in one or more blends in such examples. In examples with only one first tank 52, control based on calorific value may be performed in flight only. In examples with more than one first tank 52, a selection between first tanks may be made based on calorific value for different thrust requirements during ground-based operations, too.

Figure 15:
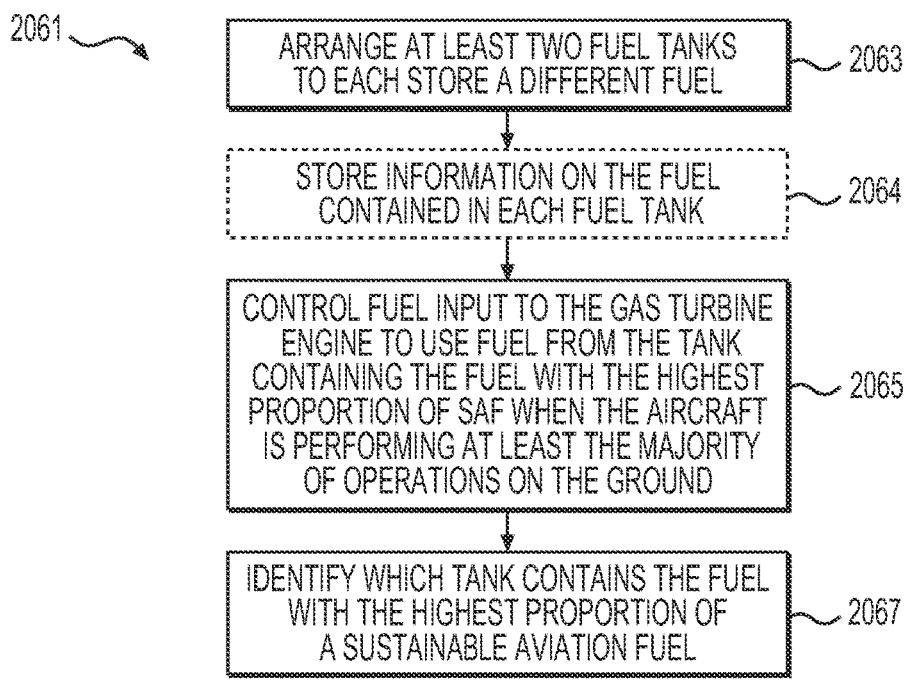
FIG. 15 is a schematic representation of another aircraft operation method.

A method 2061 of operating an aircraft 1 comprising a gas turbine engine 10, 44 and a plurality of fuel tanks 50, 52 arranged to store fuel to power the gas turbine engine 10, 44 is shown in FIG. 15.

The method 2061 comprises arranging 2063 at least two fuel tanks 50, 52 of the plurality of fuel tanks to each store a different fuel, in particular, fuels with different proportions of SAF. A first fuel tank 52 contains fuel with a higher proportion of SAF than that in a second fuel tank 50, 53. A first fuel tank 52 of the plurality of fuel tanks may be arranged to contain only a fuel which is a sustainable aviation fuel.

This arranging step 2063 may comprise fluidly isolating one or more tanks from each other, if required, so as to allow different fuels to be stored in different tanks (e.g. by closing valves). This arranging step 2063 may comprise filling the tanks 50, 52, 53 appropriately.

In some examples, one or more of the fuel tanks 50, 52 may be part of a separate set of interlinked fuel tanks. In other examples, each fuel tank 50, 52 may be a stand-alone, single-tank, fuel source.

In some examples, the fuel in the first fuel tank 52 has a % SAF greater than 50%, for example being greater than or equal to 55%, 60% or 70%, and optionally may be 100% SAF.

The method 2061 of some examples comprises identifying 2067 which tank 52 contains the fuel with the highest proportion of a sustainable aviation fuel. If several tanks 50, 52 each contain fuel with the same, highest, % SAF, the several tanks may all be identified as first fuel tanks 52. Optionally, one or more other characteristics (e.g. calorific value, nvPM emissions) may be used to select which first fuel tank 52 to use in such scenarios. The identification 2067 may be performed by detection or determination from engine operating parameters, for example using any of the approaches described herein, or using supplied data (e.g. data transmitted to or otherwise obtained by or accessed by the fuel manager 214).

The method 2061 further comprises controlling 2065 fuel input to the gas turbine engine 10 so as to use only fuel from the tank 52 containing the fuel with the highest proportion of a sustainable aviation fuel (or, in some cases, any fuel with more than 50% SAF) when the aircraft 1 is performing at least the majority of operations on the ground. That fuel may have a SAF proportion of more than 50% SAF, and optionally at least 55% SAF. Here, using that fuel for "at least the majority" of operations may mean that at least 90% or 95% of the fuel used for ground-based operations is that fuel, and/or at least 90% or 95% of the operation time for ground-based operations is powered by that fuel, and/or that the fuel with the highest proportion of SAF is used for all ground-based operations except initial engine start-up (for which a dedicated fuel may be used as described below).

The method 2061 optionally further comprises storing 2064 information on the fuel contained in each fuel tank 50, 52, optionally in memory of an on-board fuel manager 214. The information stored may simply be a flag as to whether or not a particular tank 50, 52 contains the fuel with the highest % SAF, or a fuel with over 50% SAF. Additional information may be stored in other examples. This stored information may be used for the controlling step 2065, and in particular may be used to identify the first fuel tank 52 (and/or correspondingly one or more other tanks, if multiple tanks contain SAF or the fuel with the highest % SAF), if that is not hard-coded/hard-wired into the propulsion system 2. A look-up table of tank properties may be used to identify the first fuel tank(s) 52 instead if the tanks are always arranged to contain specific fuels.

Figure 16:
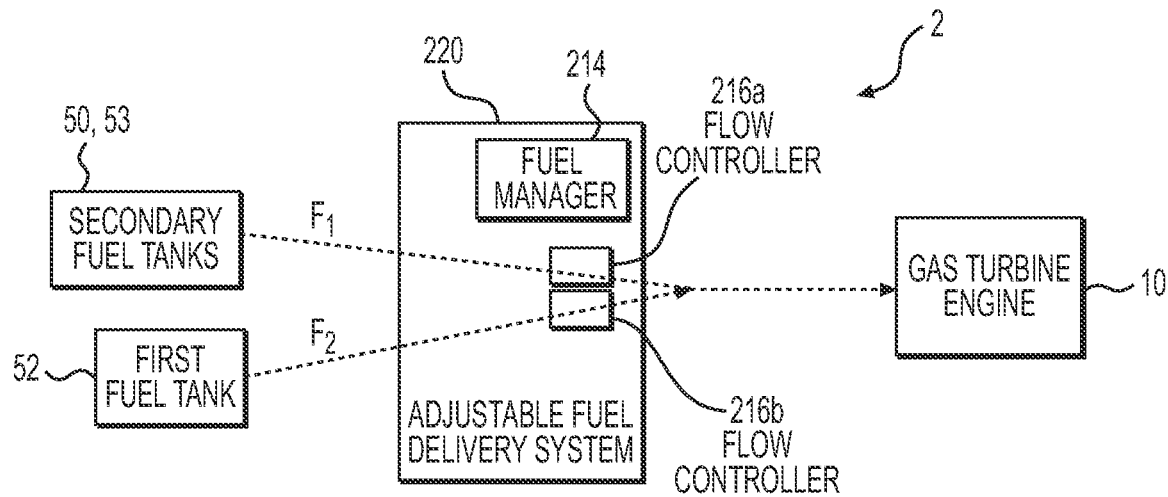
FIG. 16 is a schematic view of an aircraft fuel delivery system, in context with a fuel tank, an APU, and a gas turbine engine.

A power system 4 for an aircraft 1 may therefore comprise a fuel manager 214 arranged to store information on each fuel tank 50, 52/on the fuel contained in each fuel tank 50, 52 and to control fuel input to the gas turbine engine 10 in operation. The information stored may simply comprise a flag for whether or not each tank is the highest % SAF tank, or may comprise more detailed information, such as a % SAF content for each tank, and/or one or more other fuel characteristics of the fuel currently in each tank 50, 52 (% SAF may be defined by volume and/or mass, noting that densities can vary within accepted bounds). In such examples, which tank 52 of the plurality of fuel tanks 50, 52, 53 is the first tank 52 may vary over the lifetime of the power system 4, for example depending on which tank is filled with which fuel. In other examples, the fuel delivery system 220 as shown in FIG. 16 may be set up for one specific tank 52 to always be the highest % SAF tank, and no such fuel information may need to be stored.

The fuel manager 214 may also be arranged to identify which tank 52 contains the fuel with the highest proportion of a sustainable aviation fuel, and/or to identify all tanks containing fuels with greater than 50% SAF.

In implementations in which the SAF or highest % SAF blend is supplied to a main gas turbine engine 10 of the aircraft 1, which provides propulsive power to the aircraft 1, the power system 4 may be referred to more specifically as a propulsion system 2. The broader term "power system" 4 mentioned above is used here to ensure that implementations in which the fuel is additionally or alternatively supplied to an APU 44 are captured, as propulsive power may not be provided by such power systems 4.

The fuel manager 214 may be provided as part of a fuel delivery system 220 arranged to allow control and adjustment of the fuel supplied to the gas turbine engine 10, 44, and may be as described above for the earlier examples.

The fuel manager 214 is generally as described above. In examples with APUs 44, the fuel manager 214 may additionally be arranged to control the fuel or fuel blend provided to the APU 44.

In some of the examples being described, the fuel manager 214 is arranged to take fuel exclusively from the first fuel tank 52, i.e. the fuel tank 52 containing the fuel with the highest proportion of SAF, for ground-based operations of the power system 4.

As described above for other examples, the fuel manager 214 may additionally receive other data (in addition to information denoting which tank(s) contain(s) SAF, providing a % SAF for each tank, and/or providing other fuel characteristic data), and use that other data and the fuel characteristic data to determine a desired fuel or fuel blend for the gas turbine engine 10, 44 in flight.

The fuel manager 214 may be arranged to control fuel input to the gas turbine engine 10, 44 so as to take fuel primarily, or only, from a first fuel tank 52 when the aircraft 1 is performing operations on the ground.

In some examples, an aircraft 1 may be modified to perform the method 2061 described above, optionally by installing an adjustable fuel delivery system 220.

Figure 17:
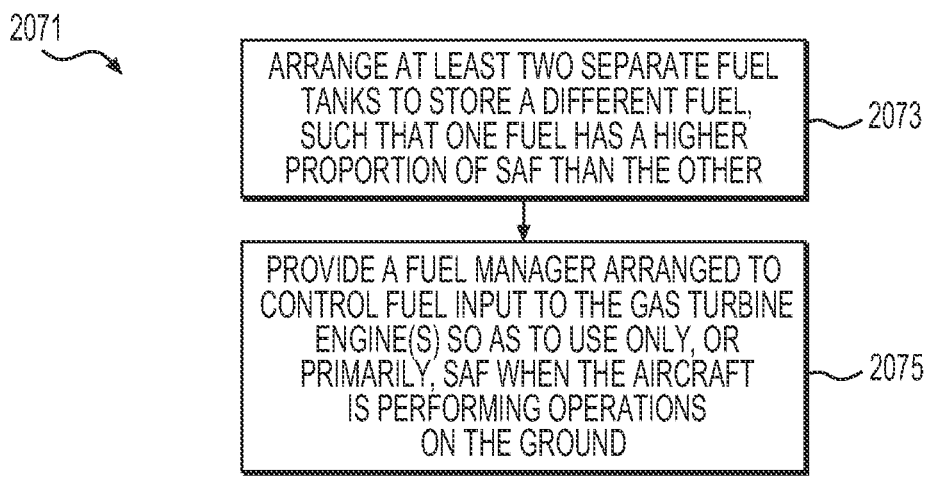
FIG. 17 is a schematic representation of another aircraft modification method.

A method 2071 of modifying an aircraft 1 in such a way is shown in FIG. 17. The original aircraft 1 comprises a gas turbine engine 10, the gas turbine engine 10 of this example comprising an engine core 11 comprising a turbine 19, a compressor 14, and a core shaft 26 connecting the turbine to the compressor. The aircraft 1 also comprises a fan 23 located upstream of the engine core, the fan comprising a plurality of fan blades and being arranged to be driven by an output from the core shaft. The original aircraft 1 may further comprise an APU 44, the APU itself being or comprising a gas turbine engine 44.

The method 2071 comprises arranging 2073 at least two separate fuel tanks 50, 52 to store a different fuel, such that one fuel has a higher proportion of SAF than the other. One or more fuel tanks may be arranged to contain only a fuel which is a sustainable aviation fuel in some implementations (in an example being described, the first fuel tank 52 of the plurality of fuel tanks 50, 52 is the only pure SAF-containing tank).

In some cases, the aircraft 1 may already comprise a plurality of fuel tanks 50, 52 arranged to store fuel to power the gas turbine engine(s) 10, 44; in such examples, the step 2073 of arranging the fuel tanks may simply comprise filling the tanks selectively with different fuels. In cases in which the aircraft 1 previously only had a single fuel tank 50, a new fuel tank 52 may be added so as to provide a plurality of fuel tanks. In cases in which the aircraft 1 previously only had a single fuel source, albeit comprised of multiple tanks, a new fuel tank 52 may be added and/or fuel lines may be adjusted such that the original tanks 50, 53 are no longer all fluidly interconnected, so providing at least two separate fuel sources. The arranging step 2073 may therefore vary depending on the initial aircraft configuration.

The method 2071 further comprises providing 2075 a fuel manager 214 arranged to control fuel input to the gas turbine engine(s) 10, 44 so as to use only, or primarily, SAF when the aircraft 1 is performing operations on the ground.

The fuel manager 214 may additionally be arranged to identify which tank 52 contains the fuel with the highest proportion of a sustainable aviation fuel—this tank 52 may be identified as a first fuel tank 52. In cases in which two or more tanks contain a fuel with the same, highest, % SAF, a plurality of tanks may be identified as first fuel tanks. A selection between these may be made using one or more of the approaches described above.

The fuel manager 214 may use fuel from the first fuel tank 52 (e.g. SAF in a specific example described, or more generally the highest % SAF fuel available, or optionally any fuel with more than 50% SAF) for some, but not all, ground-based operations. For example, the fuel manager 214 may use a different fuel for start-up before switching to using the first tank 52, may switch to a different fuel if the fuel from the first fuel tank 52 is used up before the operations on the ground are complete, and/or the fuel manager 214 may supply the fuel from the first fuel tank 52 to the APU 44 but a different fuel to the other gas turbine engine(s) 10.

In some examples, such as arrangements in which the tank(s) 52 used to store the fuel with the highest % SAF may vary over the lifetime of the propulsion system 2, the fuel manager 214 may additionally be arranged to store information on the fuel contained in each fuel tank 50, 52 so as to allow the first tank 52, or equivalent(s), to be identified.

The storage and control functions may be performed by separate entities or the same entity; it will be appreciated that the fuel manager 214 may therefore be a distributed system or a single unit or module. The step of providing 2075 the fuel manager 214 may comprise or consist of installing software in extant memory, to be executed using extant systems, in some examples. In other examples, a new physical unit or module may be mounted onto the propulsion system 2, optionally including one or more flow controllers 216 and/or replacement fuel line sections as appropriate to achieve the desired fuel flow and mixing control.

In some examples, the fuel manager 214 may be additionally arranged to perform other functions, for example to control fuel input to the gas turbine engine 10 by selection of a specific fuel or fuel combination from one or more of the plurality of fuel tanks 50, 52 based on thrust demand of the gas turbine engine 10 such that a fuel with a lower calorific value is supplied to the gas turbine engine 10 at lower thrust demand, and vice versa. It will be appreciated that thrust demand may be determined using any one or more approaches known in the art, for example as mentioned above.

The inventors also appreciated that fuel differences may allow re-design of the aircraft's fuel system to provide technical and environmental benefits for ground-based operations of an aircraft. In the present examples, described with respect to FIGS. 14 and 19, usage of the first fuel tank 52 is adjusted accordingly.

Figure 19:
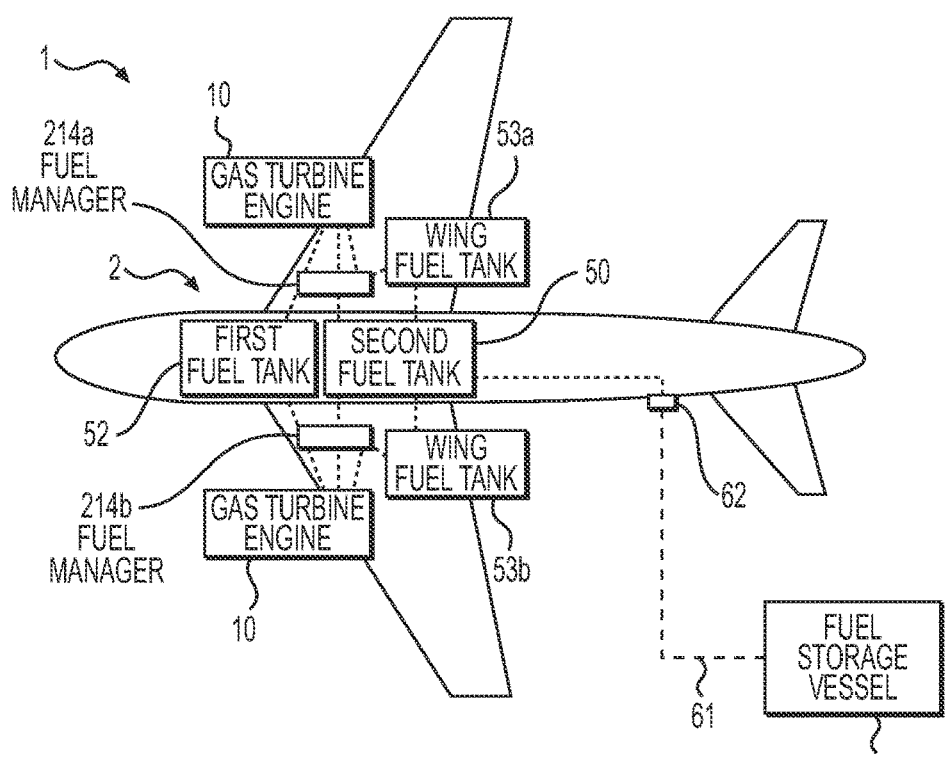
FIG. 19 is a schematic view of an aircraft including a fuel manager and having a different tank arrangement from that shown in FIG. 14.

FIG. 19 shows an aircraft 1 with a propulsion system 2 generally as for that shown in FIG. 14, but with three separate fuel sources 50, 52, 53 as opposed to two. First, second and third fuel sources are therefore not fluidly coupled to each other so as to separate the different fuels (at least under normal running conditions). In other examples, such as that shown in FIG. 14, only two separate fuel sources may be provided.

In the present example, the first fuel source is the first fuel tank 52. In other examples, the first fuel source may comprise multiple interlinked tanks. The first fuel tank 52 is arranged to be used at least primarily (and in some cases, only) for ground-based operations. Fuel from the first fuel tank 52 is arranged to be used for at least the majority of ground-based operations, in a similar way to the usage of SAF or the high % SAF blend described with respect to the preceding examples.

In the example shown in FIG. 19, the second fuel source comprises a centre fuel tank 50, located primarily in the fuselage of the aircraft, and the third fuel source comprises a plurality of wing fuel tanks 53a, 53b, where at least one wing fuel tank is located in the port wing and at least one wing fuel tank is located in the starboard wing for balancing. Tanks 53a and 53b are fluidly interconnected in the example shown, so forming a single, third, fuel source. Fluid interconnection between the wing fuel tanks 53 of the third fuel source may be provided for balancing of the aircraft 1, as described earlier.

Each of the centre fuel tank 50 and the wing fuel tanks 53 may comprise a plurality of fluidly interconnected fuel tanks.

In another example, the wing fuel tanks 53a, 53b may be fluidly connected to the central tank 50, so forming a single, second, fuel source. For balancing purposes, one or more fuel tanks in the port wing may be fluidly connected to one or more fuel tanks in the starboard wing. This may be done either via a centre fuel tank 50 (if that tank does not form part of a separate fuel source), or bypassing the centre fuel tank(s), or both (for maximum flexibility and safety).

In some examples, the allocation of fuel tanks 50, 52, 53 available on the aircraft 1 may be constrained such that each fuel source is substantially symmetrical with respect to the aircraft centre line. In cases where an asymmetric fuel tank allocation is permitted, a suitable means of fuel transfer may be provided between fuel tanks of the first fuel source and/or between fuel tanks of the second fuel source such that the position of the aircraft's centre of mass can be maintained within acceptable lateral limits throughout the flight. However, in examples in which the first fuel tank 52 is much smaller than the other fuel tanks 50, 53, its change in mass as fuel from that tank is used may be less significant and so symmetry may not be a concern.

In the examples shown in FIGS. 14 and 19, the first fuel tank 52 is again smaller than the second fuel tank 50. In the example of FIG. 14, it is located further towards the rear of the fuselage. The first fuel tank 52 of this implementation may therefore be used more easily as a trim tank 52 in flight; the approach described above with respect to trimming may therefore also be used in conjunction with the initial dedication of a tank 52 for ground use. If the first tank 52 is to be used as the trim tank in flight, the fuel in that tank 52 is either used up in the initial stages of ground operations and optionally take-off, or any remainder is mixed with other fuel pumped into that tank for trimming in flight. By contrast, in implementations in which that first tank 52 is not used as a trim tank, rather than being used up in flight or diluted, the remaining SAF in the first tank 52 could be kept until the aircraft 1 has landed and then used to power the final ground operations (e.g. landing and/or taxi-in) to obtain further air-quality benefits at the destination airport.

In various examples, an APU 44 as described above may be used to provide some or all of the power for ground-based operations, and the first fuel tank 52 may be used to provide fuel to the APU 44.

In alternative implementations, the first fuel tank 52 may be a dedicated APU fuel tank, and may not be fluidly interconnected to the main gas turbine engines 10 as it is in FIG. 14, nor to any other fuel tank. In some such examples, a fuel manager as described elsewhere herein may not be present or used.

An aircraft 1 may be refuelled by connecting a fuel storage vessel 60, such as that provided by an airport fuel truck, or a pipeline, to a fuel line connection port 62 of the aircraft 1, via a fuel line 61, as described above. In particular, in the examples being described, the first tank 52 can be fuelled directly from a fuel supply rather than having to be filled by transfer from another fuel tank 50, 53 of the aircraft 1. In FIG. 14, internal fuel lines from the port(s) 62 to the tanks are not shown, for clarity. In FIG. 19, one internal fuel line is shown (to the larger tank 50); it will be appreciated that at least a second fuel line to the first fuel tank 52 may also be provided—rather than filling the first tank 52 via a different tank—but that is not shown for clarity.

In examples of the present invention, the aircraft 1 has a plurality of fuel tanks 50, 52, 53, and in particular, a first fuel tank 52 arranged to be used to power some or all of the ground-based operation of the aircraft 1, and one or more secondary fuel tanks 50, 53, each arranged to contain a fuel to be used to power the gas turbine engine 10 in flight. Ground-based operation of the aircraft 1 may involve one or more gas turbines 10, 44—the gas turbine engine 44 of the APU 44 may be used for some ground-based operations, and one or more of the main gas turbine engines 10 may be used for other ground-based operations.

Each fuel tank 50, 52, 53 is arranged to store a fuel to be used to power one or more gas turbine engines 10, 44 of the aircraft 1. One of the fuel tanks—referred to as the first fuel tank 52—is arranged to be used for some or all ground-based operations of the aircraft 1.

Figure 21:
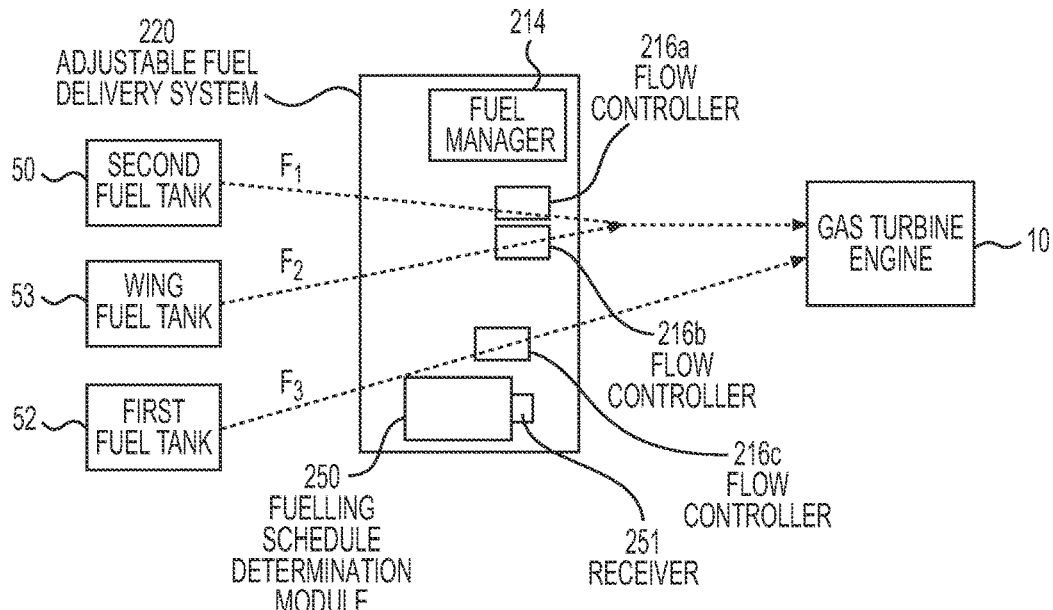
FIG. 21 is a schematic view of an aircraft fuel delivery system, in context with fuel tanks and a gas turbine engine.

In the example shown in FIG. 21, the first fuel tank 52 is dedicated to ground-based operations exclusively and fuel from that tank 52 is not used in flight. The fuel manager 214 of this example (which may generally be as described above) is arranged to control fuel input to the gas turbine engines 10, 44 so as to take fuel from only the first fuel tank 52 when the aircraft 1 is performing ground-based operations, and to take fuel from only the one or more secondary fuel tanks 50, 53 for other operations. The flow controller 216*c* may prevent fuel from being taken from the first fuel tank 52 in flight. In other examples, some fuel from the first tank 52 may also be used in flight, and/or some fuel from other tanks may be used for ground-based operations.

In some examples, the first fuel tank 52 is arranged to contain a fuel which is a sustainable aviation fuel (SAF), at least during ground-based operations—i.e. that tank 52 may contain 100% pure SAF. The fuel in the first tank 52 may be selected such that the propulsion system 2 can be run on that fuel alone for ground-based operations, whether or not that fuel would be certified for use in flight. Alternatively, the fuel in the first tank 52 may not be suitable for use in the main gas turbine engines 10, and may be used solely for the APU 44.

In the examples currently being described, the first fuel tank 52 is therefore arranged to be used to power the aircraft 1 when the aircraft is performing operations on the ground, whether or not that fuel tank 52 contains SAF.

In some implementations, such as that shown in FIG. 19, this first fuel tank 52 is arranged to only ever be used for ground-based operations (optionally with any small remainder after rotation of the aircraft 1 being finished off during climb as described earlier), and may always be isolated from the other fuel source(s) 50, 53. In other implementations, such as that shown in FIG. 14, this first fuel tank 52 is arranged to be used for ground-based operations initially, and to be fluidly isolated from the other fuel source(s) 50, 53 whilst it is being used for ground-based operations, but may then be fluidly connected to one or more other fuel sources 50, 53 in flight, and may be used as a trim tank 52, and/or to supply fuel to an engine 10, 44, in flight. The first fuel tank 52 may have a different fuel from a different fuel source 50, 53 pumped into it in flight, as compared to the fuel with which it was originally filled for powering the ground-based operations.

In some examples, the first fuel tank 52 of some implementations is designed to be used to supply fuel to one or more gas turbine engines 10, 44 only during ground-based operations, i.e. that tank is arranged to be used exclusively for ground-based operations of the aircraft 1. In some implementations, a fuel tailored for use in an APU 44 only and not suitable for combustion in a main gas turbine engine 10 may be provided in the first fuel tank 52. However, the fuel manager 214 of some examples may be arranged to allow fuel from the first fuel tank 52 to be supplied to the main gas turbine engine 10, for example alone in emergency situations or as part of a blend in normal flight, or the first fuel tank 52 may play a different role—such as that of trim tank—in flight. In other examples, a block may be provided (e.g. by a flow controller 216*c*) to prevent any introduction of fuel from the first tank 52 to the gas turbine engine 10 in flight.

In some of the examples being described, all fuel used for ground operations is taken from the first fuel tank 52. The fuel manager 214 may be arranged to control fuel input to the gas turbine engine(s) 10, 44 so as to take fuel only from the first fuel tank 52 when the aircraft 1 is performing all operations on the ground.

In other examples, the fuel taken from the first fuel tank 52 may be used for a subset of ground-based operations, with fuel from other tanks 50, 53 being used where appropriate. For example, the first fuel tank 52 may provide fuel to the APU 44 for its ground-based operations (e.g. lighting, air conditioning, main engine start), but a different fuel tank 50, 53 may provide fuel to the main gas turbine engine(s) 10 for its ground-based operations (e.g. taxi), or a different fuel may be used for initial engine warm-up/start-up, and the supply may then be switched to the first fuel tank 52 (e.g. once a threshold fuel temperature has been reached). As used herein, "operations on the ground" are as defined above.

The first fuel tank 52 may therefore be used to provide some or all of the fuel used by the aircraft power system 4 on-stand (e.g. at a gate), and during warm-up, taxi, and take-off roll.

Beneficially, this may allow a fuel tailored to the relatively low-powered requirements of ground-based operations to be stored and used, and/or may facilitate meeting airport requirements for emissions and/or use of SAF, and/or may improve functioning of the engine 10 at low thrusts.

The first fuel tank 52 of the plurality of fuel tanks may be arranged to contain only a fuel which is a sustainable aviation fuel, or to contain a high % SAF blend; some or all of the nvPM and air quality benefits described above may therefore be provided. For the same reasons, 100% or high % SAF/fuel from the first fuel tank 52 may be selected to be used in an auxiliary power unit (APU) 44 of the aircraft 1 at the gate of an airport.

The first fuel tank 52 of the plurality of fuel tanks may be smaller than the one or more other fuel tanks. For example, the first fuel tank 52 may represent 3% to 20%, and optionally 5% to 10%, of the total available tank volume of the aircraft 1.

In implementations such as that shown in FIG. 14 in which the first fuel tank 52 may operate as a trim tank 52, the approach described above may be used, whether or not the fuel in the first fuel tank 52 is SAF or a high % SAF blend.

Each fuel tank 50, 52, 53 onboard the aircraft may be arranged to contain a fuel with a different type or proportion of a sustainable aviation fuel. Whilst it will be appreciated that a synthetic fuel could be made to exactly mimic a traditional kerosene fuel, one or more fuel characteristics of SAF fuel stored onboard the aircraft 1, either as a pure SAF fuel or as part of a blend, may differ from the fuel characteristics of the one or more other fuels (SAF blends or otherwise) stored onboard the aircraft 1, in other tanks.

The fuel characteristics may include one or more of those listed above, and may be determined using any of the techniques listed above, alone or in combination as appropriate, including the various example detection methods mentioned.

In other examples, no detection may be performed and supplied data on fuel composition may be relied upon instead—that data may be simply "ground-use fuel" vs. "flight-use fuel", or may include more detailed fuel characteristic information. In other examples, no fuel data at all may be supplied—instead, each tank 50, 52, 53 may be identified as a ground-use tank 52 or a standard-use tank 50, 53, and such examples may rely on the tanks 50, 52, 53 being correctly filled accordingly.

The power system 4 comprises an adjustable fuel delivery system 220, allowing a selection to be made of which tank(s) 50, 52, 53, and therefore what fuel or fuel blend, to use. A fuel manager 214 as described above may control this system 220. In examples in which the fuel blend or fuel can be changed in flight (rather than having one flight setting and one ground setting), the fuel characteristics may vary over the course of a flight—a specific fuel or fuel blend may be selected to improve operation at certain flight stages or in certain external conditions. In some examples, calorific values for each available fuel may be calculated or provided, and fuel supply in flight may be controlled accordingly.

In implementations in which the fuel from the first fuel tank 52 is supplied to a main gas turbine engine 10 of the aircraft 1, which provides propulsive power to the aircraft 1, the power system 4 may be referred to more specifically as a propulsion system 2. The broader term "power system" 4 is used to ensure that implementations in which the fuel is additionally or alternatively supplied to an APU 44 are captured, as propulsive power may not be provided by such power systems 4, as discussed above.

Figure 20:
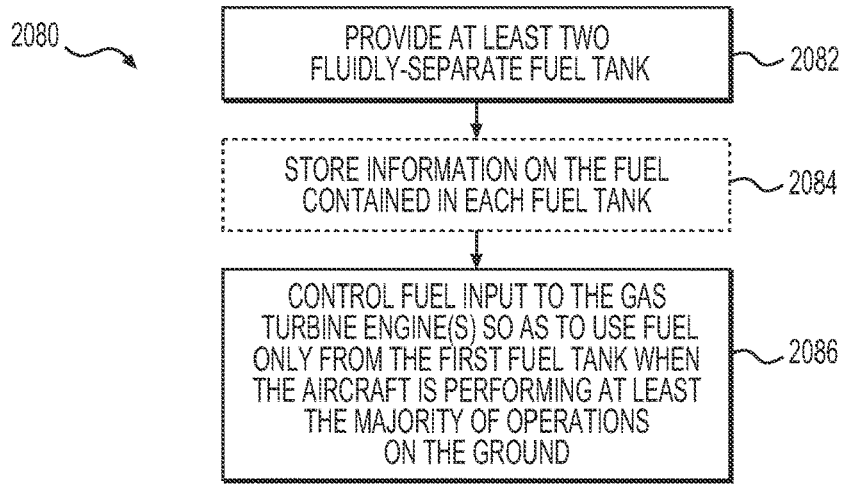
FIG. 20 is a schematic representation of an aircraft operation method.

A method 2080 of operating an aircraft 1 comprising one or more gas turbine engines 10, 44 and a plurality of fuel tanks 50, 52, 53 arranged to store fuel to power the gas turbine engine(s) 10, 44 is shown in FIG. 20.

The method 2080 comprises providing 2082 at least two fluidly-separate fuel tanks 50, 52, 53—i.e. at least two fuel sources.

The method 2080 further comprises 2086 controlling fuel input to the gas turbine engine(s) 10, 44 so as to use fuel only from the first fuel tank 52 when the aircraft 1 is performing at least the majority of operations on the ground. Here, using fuel from the first tank 52 for "at least the majority" of operations may mean that at least 90% or 95% of the fuel used for ground-based operations is fuel from the first tank 52, and/or at least 90% or 95% of the operation time for ground-based operations is powered by fuel from the first tank 52, and/or that fuel from the first tank 52 is used for all ground-based operations except initial engine start-up. The fuel manager 214 may therefore use fuel from the first fuel tank 52 for some, but not all, ground-based operations. For example, the fuel manager 214 may switch to a different fuel if the fuel from the first fuel tank 52 is used up before the operations on the ground are complete, and/or the fuel manager 214 may supply the fuel from the first fuel tank 52 to the APU 44 but a different fuel to the other gas turbine engine(s) 10. Optionally only fuel from that tank 52 may be used for all ground-based operations.

Optionally, the method 2080 may comprise taking fuel from only the one or more secondary fuel tanks 50, 53 for other operations. In other examples, fuel from the first fuel tank 52 may be provided in flight as part of a blend, but optionally not alone (except in emergency situations).

In some examples, one or more of the fuel tanks 50, 52 may be part of a separate set of interlinked fuel tanks. In other examples, each fuel tank 50, 52 may be a stand-alone, single-tank, fuel source.

The method 2080 of some examples further comprises storing 2084 information on the fuel contained in each fuel tank 50, 52, 53 and/or identifying each fuel tank 50, 52, 53, optionally in memory of an onboard fuel manager 214. The information stored may simply be a flag as to whether or not a particular tank 50, 52 is the first tank 52/is intended for use for ground-based operations. Additional information may be stored in other examples. The controlling step 2086 may be performed based on this stored information.

A propulsion system 2, or other power system 4, for an aircraft 1 may therefore comprise a fuel manager 214 arranged to control fuel input to the gas turbine engine(s) 10, 44 so as to take fuel from the first fuel tank 52 when the aircraft 1 is performing ground-based operations, and to take fuel from the one or more secondary fuel tanks 50, 53 for other operations. In some implementations, the fuel manager 214 may be arranged to control fuel input to the gas turbine engine(s) 10, 44 so as to take fuel from only the first fuel tank 52 when the aircraft 1 is performing ground-based operations, and to take fuel from only the one or more secondary fuel tanks 50, 53 for other operations.

In some examples, the fuel manager 214 may be arranged to store information on each tank/on the fuel contained in each fuel tank 50, 52, 53 and to control fuel input to the gas turbine engine(s) 10, 44 in operation accordingly. The information on the fuel contained in each fuel tank 50, 52, 53 may simply comprise a flag for whether or not each tank is the/a ground-use-tank. In such examples, which tank of the plurality of fuel tanks 50, 52, 53 is the first tank 52 may vary over the lifetime of the propulsion system 2, for example depending on which tank is filled with which fuel. In other examples, the fuel delivery system 220 may be set up for one specific tank 52 to always be the ground-use tank, and no such information may need to be stored. In examples in which fuel information is stored, the information on the fuel contained in each fuel tank 50, 52, 53 may additionally comprise more information, such as a % SAF content for each tank, and/or one or more other fuel characteristics of the fuel currently in each tank 50, 52, 53.

The fuel manager 214 may be provided as part of a fuel delivery system 220 arranged to allow control and adjustment of the fuel supplied to the gas turbine engine 10, 44, and may be as described above.

In the example shown in FIG. 21, the fuel management system 220 is arranged to allow fuels from the second and third fuel sources 50, 53 to be mixed, so as to form a blend for supply to the engine 10, but does not allow fuel from the first, ground-use, tank 52 to be blended with the other fuels. Different approaches may be used in other examples.

The fuel manager 214 of the examples currently being described is arranged to take fuel exclusively from the first fuel tank 52 for ground-based operations of the power system 4. It will be appreciated that whilst the aircraft 1 technically still has one or more wheels on the ground for the majority of take-off, take-off is a relatively high-powered activity and is generally classed as part of the flight envelope, not as a ground-based operation.

Optionally, the fuel manager 214 may additionally receive other data (in addition to information denoting which tank 50, 52, 53 is the first tank 52, and other optional fuel characteristic data), and use that other data and the fuel characteristic data to determine a desired fuel composition for the gas turbine engine 10, 44 in flight.

As mentioned above, the fuel manager 214 may be provided as a separate fuel management unit 214 built into the propulsion system 2, and/or as software and/or hardware incorporated into the pre-existing aircraft control systems. In some examples, fuel composition data and/or tank identification data may be stored separately from the circuitry performing the fuel supply management and be retrieved when required—wherever the data are stored, that storage can be thought of as a part of the fuel manager 214, whether or not it is integral or physically connected in any way.

The fuel manager 214 of the examples currently being described is arranged to control fuel input to the gas turbine engine 10, 44 so as to take fuel from the first fuel tank 52 to power at least the majority of operations on the ground.

In some examples, the fuel manager 214 may be arranged to be able to mix fuels from the secondary fuel tanks 50, 53 arranged to power the gas turbine engine 10 in flight, but not to be able to mix fuel from the first fuel tank 52 with fuel from the secondary fuel tanks 50, 53.

In some examples, the fuel manager 214 may be arranged to select a specific fuel or fuel combination from one or more of the plurality of fuel tanks based on thrust demand of the gas turbine engine in flight. In particular, a fuel with a lower calorific value may be supplied to the gas turbine engine 10 at lower thrust demand, and vice versa. A fuel with a higher calorific value may therefore be used at high-power stages of the flight envelope, such as during take-off. The fuel manager 214 may be arranged such that a fuel with a lower calorific value is supplied to the gas turbine engine 10 at cruise than during climb. Optionally, a fuel with a still lower calorific value may be supplied to the gas turbine engine 10 at ground idle (low idle).

The fuel manager 214 may make changes to the fuel supply directly, or may provide a notification or suggestion to the pilot regarding the change, for approval, as described in more detail above. In some examples, the same fuel manager 214 may automatically make some changes, and request others, depending on the nature of the change.

In some examples, an aircraft 1 may be modified to perform the method 2080 described above, optionally by installing an adjustable fuel delivery system 220.

Figure 22:
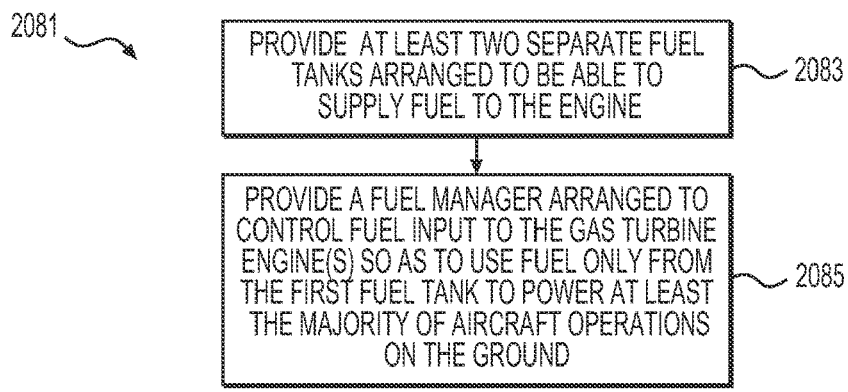
FIG. 22 is a schematic representation of an aircraft modification method.

A method 2081 of modifying an aircraft 1 in such a way is shown in FIG. 22. The original aircraft 1 comprises a gas turbine engine 10, and in this example the gas turbine engine 10 comprises an engine core 11 comprising a turbine 19, a compressor 14, and a core shaft 26 connecting the turbine to the compressor. The aircraft 1 also comprises a fan 23 located upstream of the engine core, the fan comprising a plurality of fan blades and being arranged to be driven by an output from the core shaft. The original aircraft 1 may further comprise an APU 44, the APU itself being or comprising a gas turbine engine 44.

The method 2081 comprises providing 2083 at least two separate (not fluidly-linked, or at least capable of being fluidly isolated from each other) fuel tanks 50, 52, 53, arranged to be able to supply fuel to the engine 10. A first fuel tank 52 of the plurality of fuel tanks 50, 52, 53 is arranged to be used to provide fuel for at least the majority of ground-based operations. One or more other fuel tanks 50, 53 are arranged to be used to provide fuel for all operations not covered by the first fuel tank 52.

In some cases, the aircraft 1 may already comprise a plurality of fuel tanks 50, 52, 53 arranged to store fuel to power one or more gas turbine engines 10, 44; in such examples, the step 2083 of arranging the fuel tanks may simply comprise ensuring that one of the tanks 52 is set up to be used for ground-based operations and that at least one different tank 50, 53 is set up to be used in flight.

In cases in which the aircraft 1 previously only had a single fuel tank 50, a new fuel tank 52 may be added so as to provide a plurality of fuel tanks. In cases in which the aircraft 1 previously only had a single fuel source, albeit comprised of multiple tanks, a new fuel tank 52 may be added and/or fuel lines may be adjusted such that the original tanks 50, 53 are no longer all fluidly interconnected, so providing at least two separate fuel sources. The arranging fuel tanks/providing a separate first fuel tank 52 step 2083 may therefore vary depending on the initial aircraft configuration.

The method 2081 further comprises providing 2085 a fuel manager 214 arranged to control fuel input to the gas turbine engine(s) 10, 44 so as to use fuel only from the first fuel tank 52 to power at least the majority of aircraft operations on the ground. The fuel manager 214 may also be arranged to store information on the fuel contained in each fuel tank 50, 52, 53, and/or an identifier for each tank to indicate its intended use.

The storage and control functions may be performed by separate entities or the same entity; it will be appreciated that the fuel manager 214 may therefore be a distributed system or a single unit or module, as described above. The step of providing 2085 the fuel manager 214 may comprise or consist of installing software in extant memory, to be executed using extant systems, in some examples. In other examples, a new physical unit or module may be mounted onto the propulsion system 2 (or other power system 4), optionally including one or more flow controllers 216 and/or replacement fuel line sections as appropriate to achieve the desired fuel flow and mixing control.

In some examples, the fuel manager 214 may be additionally arranged to perform other functions, for example, the fuel manager 214 may additionally be arranged to control fuel input to the gas turbine engine 10 in flight by selection of a specific fuel or fuel combination from one or more of the plurality of fuel tanks 50, 53 based on thrust demand of the gas turbine engine 10 such that a fuel with a lower calorific value is supplied to the gas turbine engine 10 at lower thrust demand, and vice versa. It will be appreciated that thrust demand may be determined using any one or more approaches known in the art, for example based on fuel flow rate and/or power lever angle in the cockpit or one or more other pilot settings, and optionally taking account of outside air density, or a proxy for it such as altitude, ambient temperature, and/or pressure. The examples currently being described may therefore be used in conjunction with examples described above.

The inventors also appreciated that whilst use of SAF may provide benefits over many parts of the flight envelope, initial engine start-up (i.e. from when the engine is "cold"/ not in operation whilst an aircraft 1 is parked) may suffer due to certain properties of some SAF types, such as potentially increased viscosity and/or lower lubricity of SAF as compared to more traditional, fossil-derived, fuels. Changes in control of the aircraft's fuel system may therefore allow technical and environmental benefits of SAF to be realised without compromising start-up operation. In particular, using a short "burst" of a fossil-based hydrocarbon fuel, such as Jet A, Jet A-1, or another fuel optimised for use in cold-start/start-up conditions (SAF or otherwise), for start-up before switching to a SAF fuel (or to a different SAF fuel) may provide smoother start-up whilst still allowing the benefits of SAF to be obtained thereafter. More generally, whatever fuel is to be used later in operation, a fuel optimised for start-up may be used initially—such a fuel may have a lower freeze temperature and/or a lower viscosity at a given temperature than other fuel aboard the aircraft 1.

Whilst it will be appreciated that a synthetic fuel could be made to exactly mimic a traditional kerosene fuel, one or more fuel characteristics of SAF stored onboard the aircraft may differ from the fuel characteristics of the one or more other, fossil-derived, fuels stored onboard the aircraft, in other tanks. In particular, the viscosity of SAFs may be higher at a given temperature than that for a traditional fossil-derived fuel, and decrease with increasing temperature. As such, once the engine has warmed up, such a fuel will have an improved viscosity for use due to the increased temperature.

A fuel optimised for start-up—for example having a higher lubricity at a given temperature and/or a lower heat capacity—may therefore be selected, which may be of particular benefit for start-up in cold conditions, irrespective of whether or not any or all fuels carried are or include SAF. The start-up optimised fuel may or may not be certified for use in flight—it may be dedicated to start-up use.

A first fuel source and a second fuel source may therefore be used, providing different first and second fuels. The second fuel may be selected to have improved characteristics with respect to start-up operation. In some cases, the first fuel may be a sustainable aviation fuel and the second fuel may be fossil-derived; however, this option is not intended to be limiting.

In the present examples, described with respect to FIGS. 14 and 18, the first fuel source is the first fuel tank 52. In other examples, the first fuel source may comprise multiple interlinked tanks. In some examples, the first fuel tank 52 is arranged to contain only a fuel which is a pure sustainable aviation fuel (SAF), i.e. 100% sustainably sourced and not kerosene derived/of fossil origin. In other examples, multiple fuel tanks of a plurality of fuel tanks may all contain SAF—any one of the subset of fuel tanks containing SAF may therefore be used to supply SAF, or the first fuel tank 52 may contain a SAF-blend or a fossil-derived fuel; it will be appreciated that the example of just one fuel tank 52 containing SAF is described here by way of non-limiting example only. In the present examples, described with respect to FIGS. 14 and 18, the second fuel source is or comprises the second fuel tank 50. The second fuel tank 50 is arranged to contain only a fuel which is selected for improved start-up properties, and which may be fossil-derived/petroleum-based. Again, it will be appreciated that these arrangements are being described by way of example only, and are not intended to be limiting.

In some implementations, the first fuel tank 52 and the second fuel tank 50 may be used to supply fuel to both the main gas turbine engine(s) 10 and the APU 44. In other implementations, either or both tanks 50, 52 may be used to supply fuel to either the main (propulsive) gas turbine engine(s) 10 or the APU 44, but not both—other fuel tanks may be provided to provide fuel to the other gas turbine engine(s) 10, 44 in such implementations.

In some of the examples being described, all fuel used for ground operations except for that used for the initial start-up is sustainable aviation fuel or a high % SAF blend, and all other fuel used for ground operations is therefore taken from the first fuel tank 52 containing the sustainable aviation fuel or high % SAF blend (in examples with multiple SAF-containing tanks, any one or more of those tanks may be used, as appropriate). The fuel used for start-up may be SAF or a SAF blend in some cases.

A fuel manager 214 as described above may be arranged to control fuel input to the gas turbine engine(s) 10, 44 so as to take fuel from the second fuel tank 50 at start-up, and then to switch to another fuel tank 52.

SAF or a high % SAF blend may therefore be used when the aircraft is performing at least the majority of operations on the ground (as defined above), so optionally providing one or more of the benefits described above (e.g. reduced nvPM), whether or not the fuel used for the initial engine start-up is SAF. In some implementations, SAF or SAF-blends may be used for the majority of, or all, aircraft operations, both ground-based and flight.

Although FIGS. 14 and 18 show the second fuel tank 50 as relatively large, in some implementations, the second fuel tank 50 may be smaller than the one or more other fuel tanks 52, 53. For example, the first fuel tank 50 may represent 1% or 2% to 15%, and optionally 3% to 5%, of the total available tank volume of the aircraft 1. Optionally, that tank 50 may be arranged to be used exclusively for engine start-up. A fuel optimised for start-up use, even at the cost of performance in normal use, may therefore be selected as the second fuel.

Each fuel tank 50, 52 onboard the aircraft 1 may be arranged to contain a fuel of a different type (e.g. petroleum-origin fuel or SAF, or different SAF varieties), and some tanks may contain blended fuels with a proportion of a sustainable aviation fuel mixed with a traditional jet fuel or other petroleum-origin fuel. At least one tank 52 may contain SAF—i.e. purely a sustainable aviation fuel, not a blend, in some examples. At least one tank 50 contains a start-up optimised fuel, which may or may not be a fossil-based fuel.

The propulsion system 2 of the examples being described again comprises an adjustable fuel delivery system 220, allowing a selection to be made of which tank(s) 50, 52, 53, and therefore what fuel or fuel blend, to use. In such examples, the fuel characteristics may vary over the course of a journey—a specific fuel or fuel blend may be selected to improve operation at certain flight stages or in certain external conditions, for example as described above with respect to other aspects.

In examples in which detection is used for one or more fuel characteristics (either by direct detection, or by inference from detected parameters), e.g. to discover or verify which tank contains the fuel for use at start-up, any of the detection approaches described above may be implemented. In other examples, no detection may be performed and supplied data on fuel composition may be relied upon instead—that data may be simply e.g. "Fuel for start-up" or "Other", or may include more detailed fuel characteristic information. In other examples, no fuel data at all may be supplied—instead, each tank 50, 52, 53 may be identified as e.g. a "Start-up" tank or a "Normal use" tank, and the example may rely on the tanks 50, 52, 53 being correctly filled accordingly.

In some examples, calorific values for each available fuel may be calculated or provided, and a fuel or fuel blend supplied based on thrust demand as described above (optionally also considering altitude)—some fuel from the first tank 52 (e.g. SAF) and/or fuel from the second tank 50 (e.g. a fossil-based fuel) may be used alone and/or in one or more blends in such examples.

Figure 23:
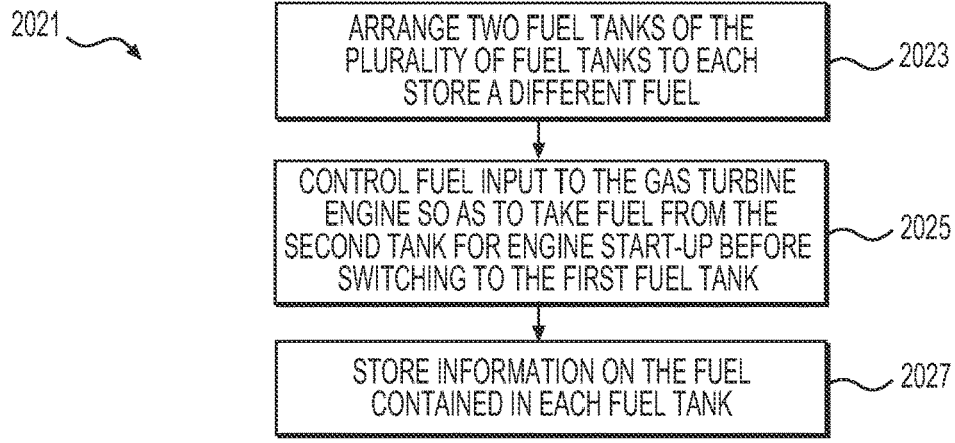
FIG. 23 is a schematic representation of an aircraft operation method.

A method 2021 of operating an aircraft 1 comprising a gas turbine engine 10, 44 and a plurality of fuel tanks 50, 52 arranged to store fuel to power the gas turbine engine 10, 44 is shown in FIG. 23.

The method 2021 comprises arranging 2023 two fuel tanks 50, 52 of the plurality of fuel tanks to each store a different fuel. In particular, a first fuel tank 52 of the plurality of fuel tanks is arranged to contain only a fuel which is a sustainable aviation fuel in this example, and a second fuel tank 50 of the plurality of fuel tanks is arranged to contain a fuel selected for improved start-up properties, which may be or comprise a fossil-based hydrocarbon fuel. This arranging step 2023 may comprise fluidly isolating one or more tanks from each other so as to allow different fuels to be stored in different tanks (e.g. by closing valves). This arranging step 2023 may comprise filling the tanks appropriately.

In some examples, one or more of the fuel tanks 50, 52 may be part of a separate set of interlinked fuel tanks. In other examples, each fuel tank 50, 52 may be a stand-alone, single-tank, fuel source.

The method 2021 further comprises controlling 2025 fuel input to the gas turbine engine 10 so as to take fuel from the second tank 50 for engine start-up, before switching to the first fuel tank 52. The first fuel tank 52 may contain SAF, and may be the only fuel source used for ground-based operations after start-up, such that SAF is used when the aircraft 1 is performing at least the majority of operations on the ground.

The control 2025 of the fuel, optionally managed by a fuel manager 214, may comprise switching from taking fuel from the second tank 50 to taking fuel from the first fuel tank 52 when a selected parameter, such as fuel temperature, turbine gas temperature, oil temperature, shaft speed, or time since the engine was turned on, reaches a certain threshold. For example, the change in fuel may be made when:
  (i) the fuel reaches a temperature of at least 60° C., and optionally of 80° C., 85° C., 90° C., 95° C., or 100° C., at the inlet to the combustor 16; or
  (ii) after the gas turbine engine 10, 44 has been running for a period of at least thirty seconds, at least one minute, at least three minutes, or at least five minutes.

For some engines 10, a period of at least 10 minutes or 15 minutes may be selected.

It will be appreciated that a suitable time period may depend on environmental conditions (e.g. a lower air temperature and corresponding lower initial fuel temperature may result in a longer start-up time period) and on properties of the aircraft 1 and fuel supply system, and may be adjusted as applicable for a given aircraft 1 and environment.

In some implementations, the switch from taking fuel from the second tank 50 to taking fuel from the first fuel tank 52 may be actioned when the engine 10 reaches idle conditions, and optionally a short period (e.g. thirty seconds) after idle conditions have been reached to ensure that the idle operation has stabilised. In some cases, the engine 10 may be allowed to run at idle for at least two minutes, or at least five minutes. In some implementations, a time period may be set based on for how long the engine 10 has been shut down since its last use—for example setting the period at two minutes if the engine 10 has been shut down for less than 90 minutes, and at five minutes if the engine has been shut down for longer than 90 minutes.

The time at which idle operation is reached may be identified based on a temperature or shaft speed, for example, which may be specific to the engine 10 and/or aircraft 1 in question.

In some implementations, the switch from taking fuel from the second tank 50 to taking fuel from the first fuel tank 52 may be actioned when the engine 10 reaches a defined limitation in the Engine Operating Instructions that prevents take-off until certain criteria are met. It will be appreciated that specific parameters and values can be looked up in the Engine Operating Instructions for a given engine 10. The engine 10 reaching a state in which it would be ready for take-off indicates that a start-up phase is complete (although the change of fuel may be made earlier in some implementations).

The method 2021 optionally further comprises storing 2027 information on the fuel contained in each fuel tank 50, 52, optionally in memory of an on-board fuel manager 214. The information stored may simply be a flag as to whether or not a particular tank 50, 52 contains a fuel selected for its start-up properties (which may be fossil-based). A flag marking one or more tanks as containing 100% SAF or a high % SAF blend may also be provided. Additional information may be stored in other examples. This stored information may be used for the controlling step 2025, and in particular may be used to identify the first fuel tank 52 (and/or correspondingly one or more tanks containing fuel for general use/use for purposes other than start-up, if there are multiple such tanks) and the second fuel tank 50 (and/or correspondingly one or more other tanks, if multiple tanks contain fuels suitable for start-up), if that is not hard-coded/hard-wired into the propulsion system 2.

A power system 4 for an aircraft 1 may therefore comprise a fuel manager 214 arranged to store information on each fuel tank 50, 52, 53/on the fuel contained in each fuel tank 50, 52, 53 and to control fuel input to the gas turbine engine 10, 44 in operation. The information stored may simply comprise a flag for whether or not each tank is the start-up tank, or may comprise more detailed information, such as a % SAF content for each tank, and/or one or more other fuel characteristics of the fuel currently in each tank 50, 52. In such examples, which tank 50, 52 of the plurality of fuel tanks 50, 52, 53 is the first tank 52 and which is the second fuel tank 50 may vary over the lifetime of the power system 4, for example depending on which tank is filled with which fuel. In other examples, the fuel delivery system 220 as shown in FIG. 16 may be set up for one specific tank 50 to always be the start-up tank, and no such information may need to be stored. Optionally, one specific tank 52 may always be a/the SAF tank or high % SAF blend tank.

In implementations in which the start-up fuel and the other, first, fuel are supplied to a main gas turbine engine 10 of the aircraft 1, which provides propulsive power to the aircraft 1, the power system 4 may be referred to more specifically as a propulsion system 2. The broader term "power system" 4 mentioned above is used here to ensure that implementations in which the fuels are additionally or alternatively supplied to an APU 44 are captured, as propulsive power may not be provided by such power systems 4.

As described above for other examples, the fuel manager 214 may be provided as part of a fuel delivery system 220 arranged to allow control and adjustment of the fuel supplied to the gas turbine engine 10, 44; any features described above may be applied as appropriate to the examples currently being described. In examples with APUs 44, the fuel manager 214 may be arranged to control the fuel or fuel blend provided to the APU 44 as well as to the main, propulsive, engine(s) 10.

The APU 44 may be required in flight, in some circumstances, and its availability under such circumstances may be time-critical—for example to re-start the main engines 10 after a main engine flame-out. When starting up the APU 44 in flight, it may be cold (having been unused for up to several hours); the fuel manager 214 may therefore be (alternatively or additionally) arranged to provide the second fuel to perform the start-up of the APU 44 in flight quickly and reliably. To avoid losing time by inadvertently trying to start the APU 44 on a fuel with poor properties for start-up, the APU 44 could be automatically switched to draw fuel from the second tank (e.g. with a lower-viscosity fuel at a given temperature) whenever the aircraft 1 is airborne (e.g. with reference to the "weight-on-wheels" indicator), but to use any fuel when on the ground (when start-up time is less likely to be crucial).

In some implementations, the first tank 52 may be empty for at least part of the airborne part of the journey, or indeed refilled with a different fuel if the tank 52 is used as a trim tank. The fuel manager 214 may therefore be arranged to take appropriate action depending on current content and/or usage of the first fuel tank 52 when considering whether or not to take fuel from the first fuel tank for engine 10, 44 start-up in flight.

As described above for other examples, the fuel manager 214 may additionally receive other data (in addition to information denoting which tank(s) contain(s) a fuel selected for start-up, and other optional fuel characteristic data, such as SAF content), and use that other data and the fuel characteristic data to determine a desired fuel composition for the gas turbine engine 10, 44 in flight.

In some examples, an aircraft 1 may be modified to perform the method 2021 described above, optionally by installing an adjustable fuel delivery system 220.

Figure 24:
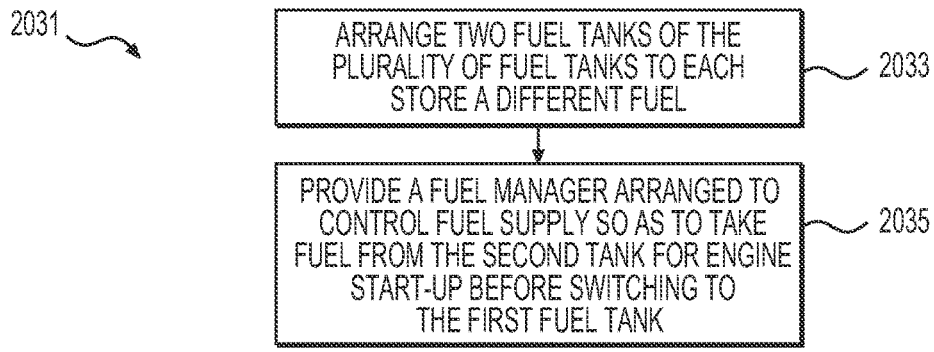
FIG. 24 is a schematic representation of an aircraft modification method.

A method 2031 of modifying an aircraft 1 in such a way is shown in FIG. 24. The original aircraft 1 comprises a gas turbine engine 10, the gas turbine engine 10 optionally comprising an engine core 11 comprising a turbine 19, a compressor 14, and a core shaft 26 connecting the turbine to the compressor. The aircraft 1 also comprises a fan 23 located upstream of the engine core, the fan comprising a plurality of fan blades and being arranged to be driven by an output from the core shaft.

The original aircraft 1 may further comprise an APU 44, the APU itself being or comprising a gas turbine engine 44.

The method 2031 comprises arranging 2033 two fuel tanks 50, 52 of the plurality of fuel tanks to each store a different fuel. In particular, a first fuel tank 52 of the plurality of fuel tanks is arranged to contain a first fuel, which may be a sustainable aviation fuel, and a second fuel tank 50 of the plurality of fuel tanks is arranged to contain a fuel selected for its improved start-up properties as compared to the first fuel, and which may be a fossil-based hydrocarbon fuel.

In some cases, the aircraft 1 may already comprise a plurality of fuel tanks 50, 52 arranged to store fuel to power the gas turbine engine(s) 10, 44; in such examples, the step 2033 of arranging the fuel tanks may simply comprise filling the tanks selectively with different fuels. In cases in which the aircraft 1 previously only had a single fuel tank 50, one or more new fuel tanks 52, 53 may be added so as to provide a plurality of fuel tanks. In cases in which the aircraft 1 previously only had a single fuel source, albeit comprised of multiple tanks, a new fuel tank 52 may be added and/or fuel lines may be adjusted such that the original tanks 50, 53 are no longer all fluidly interconnected, so providing at least two separate fuel sources. The arranging step 2033 may therefore vary depending on the initial aircraft configuration.

The method 2031 further comprises providing 2035 a fuel manager 214 arranged to control fuel supply so as to take fuel from the second tank 50 for engine start-up, before switching to the first fuel tank 52. The fuel manager 214 may use fuel from the first fuel tank 52 (which is SAF in a specific example described, but may be a SAF blend or a pure fossil-based fuel in other examples) for all ground-based operations after start-up.

In some examples, such as arrangements in which the tank(s) used to store the fuel selected for start-up may vary over the lifetime of the propulsion system 2, the fuel manager 214 may additionally be arranged to store information on the fuel contained in each fuel tank 50, 52 so as to allow the first tank 52 and second tank 50, or equivalent (s), to be identified.

The storage and control functions may be performed by separate entities or the same entity; it will be appreciated that the fuel manager 214 may therefore be a distributed system or a single unit or module. The step of providing 2035 the fuel manager 214 may comprise or consist of installing software in extant memory, to be executed using extant systems, in some examples. In other examples, a new physical unit or module may be mounted onto the propulsion system 2, optionally including one or more flow controllers 216 and/or replacement fuel line sections as appropriate to achieve the desired fuel flow and mixing control.

In some examples, the fuel manager 214 may be additionally arranged to perform other functions, for example to control fuel input to the gas turbine engine 10 by selection of a specific fuel or fuel combination from one or more of the plurality of fuel tanks 50, 52, 53 based on thrust demand of the gas turbine engine 10 such that a fuel with a lower calorific value is supplied to the gas turbine engine 10 at lower thrust demand, and vice versa. It will be appreciated that thrust demand may be determined using any one or more approaches known in the art, for example as mentioned above.

The inventors also appreciated that, as different fuels can have different properties whilst still conforming to the standards, knowledge of the flight profile can allow a selection to be made of which of the fuels available to an aircraft 1 is used for which portion(s) of the flight profile (when multiple fuels are available)—this may provide improved aircraft performance. For example, a fuel with improved emissions outcomes may be selected for operations at or near an airport, and a fuel with a higher calorific value may be used for operations with higher thrusts. A fuelling schedule defining which fuel, or fuel blend, to use for each portion of the flight profile may therefore be determined based on knowledge of the flight profile and of the available fuels.

Figure 25:
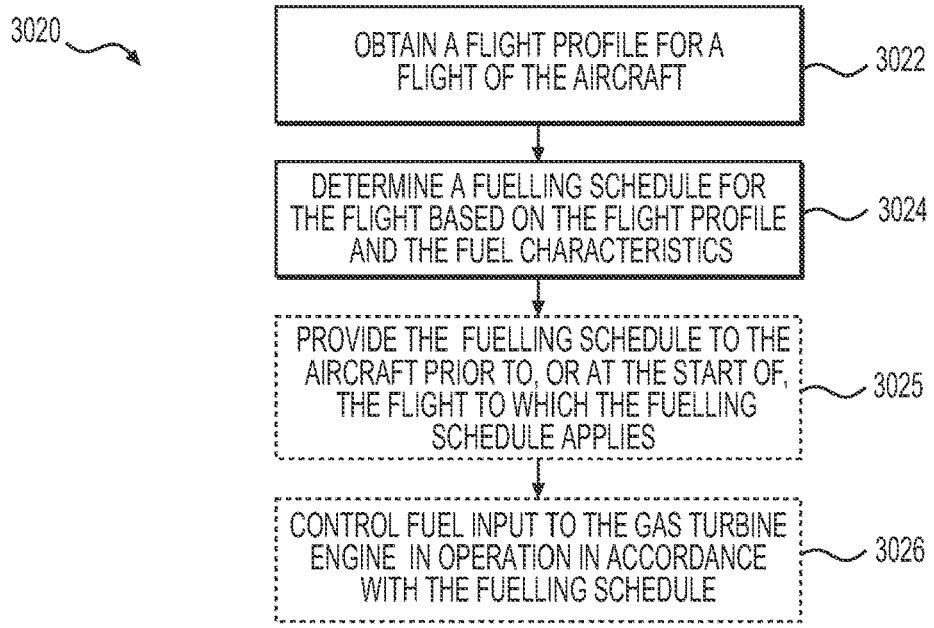
FIG. 25 is a schematic representation of an aircraft operation method.

Such a method 3020 is depicted in FIG. 25. It will be appreciated that an aircraft 1 for which the method 3020 is implemented must comprise at least two fuel sources 50, 53, such that at least two different fuels (i.e. fuels with at least one difference in fuel characteristics between them) are available for use. It will be appreciated that the use of fuel blends with different blend ratios may allow for many more than two fuelling options even with only two different fuels stored onboard.

The method 3020 may be performed on-wing, e.g. by a fuelling schedule determination module 250 of the aircraft 1 as illustrated in FIG. 21. Such a fuelling schedule determination module 250 may form a part of an electronic engine controller (EEC) 42 of the aircraft 1, optionally being provided as software installed on an extant EEC 42, or added as a module thereto, or may be provided by a separate module. Alternatively, the method 3020 may be performed off-wing, and the fuelling schedule provided to the aircraft 1 for implementation. It will be appreciated that any suitable processing means may be used to perform the role of the fuelling schedule determination module 250, and that computer-readable instructions to cause the processing means to implement the method 3020 being described may be provided.

The method 3020 may therefore be performed by processing circuitry of the aircraft 1, or by separate, off-wing, processing circuitry. The method 3020 may be performed by processing circuitry of a portable computing device, for example a pilot's personal computing device.

A fuel manager 214 as described above may be used to implement the fuelling schedule. The fuelling schedule determination module 250, or other processing circuitry, may provide the fuelling schedule to the fuel manager 214 for implementation.

The method 3020 comprises obtaining a flight profile for a flight of the aircraft 1. The flight profile may be provided to a fuelling schedule determination module 250 of the aircraft 1, or to an off-wing fuelling schedule determination module. The flight profile may be obtained in any suitable way, for example being sent electronically, manually entered via a user interface, or retrieved from memory.

The method 3020 further comprises determining 3024 a fuelling schedule for the flight of the aircraft 1 based on the flight profile and the fuel characteristics of the available fuels. In determining 3024 the fuelling schedule, an amount of each fuel available onboard the aircraft 1 is also taken into account. The altitude and route of the aircraft 1 for the intended flight are defined in the flight profile. Expected thrust demands may be included in the flight profile, or determined or inferred based on the flight profile, and may be used to guide fuel selection. In addition, data relating to forecast weather conditions along the intended route of the aircraft 1 as defined in the flight profile may be provided with the flight profile, or requested based on the flight profile. The weather data may be used to influence the determination 3024 of fuel scheduling.

The determined fuelling schedule specifies a desired variation with time of how much fuel is drawn from each tank 50, 53; i.e. it lists which fuel or fuel blend should be used for each stage of the flight as defined in the flight profile, and therefore determines when a change in fuelling should be made, and the nature of the change.

The fuel characteristics considered comprise one or more of the fuel characteristics as defined elsewhere herein.

For example, the amount of sustainable aviation fuel—SAF—available to the aircraft 1, optionally as both pure SAF and in blends, may be determined. As described above, using SAF or high % SAF blends for ground operations may offer reduced nvPM emissions and therefore improved airport air quality, and the fuelling schedule may prioritise the use of SAF/a fuel with a high % SAF for ground-based operations of the aircraft 1.

Similarly, and as described above, a calorific value of each fuel onboard the aircraft 1 may be a fuel characteristic of interest, and the fuelling schedule may prioritise the use of higher calorific value fuels for higher thrust operations of the aircraft 1, and of lower calorific value fuels for lower thrust operations of the aircraft 1.

The fuelling schedule may be determined onboard the aircraft 1; for example in an engine electronic controller 42 or other processing circuitry of the aircraft 1, or in a device belonging to the pilot. Alternatively, the fuelling schedule may be determined off-wing, e.g. in a ground-based server or other computing system. The determined fuelling schedule may therefore be provided 3025 to the aircraft 1 prior to, or at the start of, the flight to which the fuelling schedule applies. Different steps of the method 3020 may therefore be performed by entirely separate entities in some cased, or all within or by the aircraft 1 in other cases.

In some implementations, the method 3020 further comprises controlling 3026 fuel input to the gas turbine engine 10 in operation in accordance with the fuelling schedule. In particular, a fuel manager 214 as described above may receive the fuelling schedule and control fuel supply accordingly, for example by opening or closing one or more valves, or activating or deactivating one or more pumps, as appropriate to provide the desired fuel or fuel blend at each stage of the flight.

A propulsion system 2 for an aircraft 1 may be arranged to implement the method 3020 described above. The propulsion system 2 comprises a gas turbine engine comprising at least two separate fuel sources 50, 53, such that at least two different fuels (i.e. fuels having different fuel characteristics) are stored aboard the aircraft 1.

The propulsion system 2 of such examples includes a fuelling schedule determination module 250 which is arranged to obtain 3022 a flight profile for a flight of the aircraft 1; and determine 3024 a fuelling schedule for the flight based on the flight profile and the fuel characteristics.

The fuelling schedule determination module 250 may implement the control 3026 of fuel supply to the gas turbine engine 10 itself, or may pass the fuelling schedule to a fuel manager 214 for implementation.

The propulsion system 2 of some examples additionally comprises a receiver 251 arranged to receive forecast weather conditions for the intended route of the aircraft 1, which is defined in the flight profile. The received forecast weather conditions may be used to influence the fuelling schedule, as mentioned above.

It will be understood that the invention is not limited to the embodiments above-described and various modifications and improvements can be made without departing from the concepts described herein. Except where mutually exclusive, any of the features may be employed separately or in combination with any other features and the disclosure extends to and includes all combinations and sub-combinations of one or more features described herein.

We claim:

1. A method of identifying a fuel contained in a fuel tank of an aircraft for powering a gas turbine engine of the aircraft, the method being performed by processing circuitry of the aircraft and comprising:
   obtaining at least one first composition-dependent fuel characteristic of a first fuel present in the fuel tank prior to refueling the aircraft;
   determining at least one second composition-dependent fuel characteristic of a second fuel added to the fuel tank on refueling the aircraft;
   refueling the aircraft using the second fuel to thereby produce a resultant fuel in the fuel tank, the resultant fuel comprising the first fuel and the second fuel; and
   calculating, based on both the obtained at least one first composition-dependent fuel characteristic of the first fuel and the determined at least one second composition-dependent fuel characteristic of the second fuel, at least one third composition-dependent fuel characteristic of the resultant fuel in the fuel tank after refueling the aircraft.

2. The method of claim 1, wherein the obtaining at least one first composition-dependent fuel characteristic of the first fuel present in the fuel tank prior to refueling the aircraft comprises:
   (i) detecting at least one feature of the composition of the first fuel already present in the fuel tank; or
   (ii) obtaining a previously-calculated at least one third composition-dependent fuel characteristic of a previous resultant fuel in the fuel tank produced via a previous refueling of the aircraft, wherein the first fuel is the previous resultant fuel.

3. The method of claim 1, further comprising maintaining current fuel characteristic data by updating fuel characteristics of the first fuel present in the fuel tank with fuel characteristics of the resultant fuel following each refueling of the aircraft.

4. The method of claim 1, wherein the determining at least one second composition-dependent fuel characteristic of the second fuel added to the fuel tank on refueling comprises reading a barcode associated with the second fuel.

5. The method of claim 1, wherein each of the at least one first composition-dependent fuel characteristic, the at least one second composition-dependent fuel characteristic, and the at least one third composition-dependent fuel characteristic comprises a parameter of a hydrocarbon distribution of the first fuel, the second fuel, and the resultant fuel, respectively.

6. The method of claim 1, further comprising chemically or physically detecting at least one parameter of the resultant fuel in the fuel tank after refueling, and verifying the calculated at least one third composition-dependent fuel characteristic of the resultant fuel based on the at least one detected parameter.

7. The method of claim 1, wherein the obtaining the at least one fuel characteristic of any fuel already present in the fuel tank prior to refuelling comprises obtaining stored fuel characteristic data, and wherein the method further comprises chemically or physically detecting at least one parameter of any fuel already present in the fuel tank prior to refuelling, and verifying the input to the calculating step based on the detected at least one parameter.

8. The method of claim 1, wherein each of the at least one first composition-dependent fuel characteristic, the at least one second composition-dependent fuel characteristic, and the at least one third composition-dependent fuel characteristic comprises at least one of:
   i. a percentage of sustainable aviation fuel in the first fuel, the second fuel, and the resultant fuel, respectively;
   ii. an aromatic hydrocarbon content of the first fuel, the second fuel, and the resultant fuel, respectively;
   iii. a multi-aromatic hydrocarbon content of the first fuel, the second fuel, and the resultant fuel, respectively;
   iv. a percentage of nitrogen-containing species in the first fuel, the second fuel, and the resultant fuel, respectively;
   v. a presence or percentage of a tracer species or a trace element in the first fuel, the second fuel, and the resultant fuel, respectively;
   vi. a hydrogen to carbon ratio of the first fuel, the second fuel, and the resultant fuel, respectively;
   vii. a hydrocarbon distribution of the first fuel, the second fuel, and the resultant fuel, respectively;
   viii. a level of non-volatile particulate matter emissions on combustion of the first fuel, the second fuel, and the resultant fuel, respectively;
   ix. a naphthalene content of the first fuel, the second fuel, and the resultant fuel, respectively;
   x. a sulphur content of the first fuel, the second fuel, and the resultant fuel, respectively;
   xi. a cycloparaffin content of the first fuel, the second fuel, and the resultant fuel, respectively;
   xii. an oxygen content of the first fuel, the second fuel, and the resultant fuel, respectively;
   xiii. a thermal stability of the first fuel, the second fuel, and the resultant fuel, respectively;
   xiv. a level of coking of the first fuel, the second fuel, and the resultant fuel, respectively;
   xv. an indication whether each of the first fuel, the second fuel, and the resultant fuel, respectively, is a fossil fuel; and
   xvi. at least one of a density, a viscosity, a calorific value, and a heat capacity of the first fuel, the second fuel, and the resultant fuel, respectively.

9. The method of claim 1, further comprising chemically and/or physically determining at least one parameter of the fuel in the fuel tank, and using the determined at least one parameter to replace stored fuel characteristics for the first fuel.

10. The method of claim 9, wherein the chemically and/or physically determining at least one parameter of fuel in the fuel tank is performed by extracting a sample of fuel from the fuel tank for off-wing testing.

11. The method of claim 9, wherein the chemically and/or physically determining at least one parameter of fuel in the fuel tank and using the determined at least one parameter to replace the stored fuel characteristics for the first fuel is performed in response to a trigger event.

12. The method of claim 11, wherein the trigger event comprises one of the following:
   i. a threshold amount of time having elapsed since a previous determination of the at least one parameter of fuel in the fuel tank;
   ii. a threshold number of refueling events and/or flights having been reached since a previous determination of the at least one parameter of fuel in the fuel tank; and
   iii. a discrepancy between the calculated at least one third composition-dependent fuel characteristic and the at least one parameter exceeding a threshold.

13. The method of claim 1, further comprising controlling a propulsion system of the aircraft, the propulsion system comprising the gas turbine engine, based on the calculated at least one third composition-dependent fuel characteristic of the resultant fuel in the fuel tank after refueling.

14. The method of claim 1, further comprising proposing or initiating a change to a flight profile of the aircraft based on the calculated at least one third composition-dependent fuel characteristic of the resultant fuel in the fuel tank after refueling.

15. A method of controlling a propulsion system of an aircraft, the propulsion system comprising a gas turbine engine and a fuel tank arranged to provide fuel to the gas turbine engine, the method comprising:
- obtaining at least one first composition-dependent fuel characteristic of a first fuel present in the fuel tank prior to refueling the aircraft;
- determining at least one second composition-dependent fuel characteristic of a second fuel added to the fuel tank on refueling the aircraft;
- refueling the aircraft using the second fuel to thereby produce a resultant fuel in the fuel tank, the resultant fuel comprising the first fuel and the second fuel;
- calculating, based on both the obtained at least one first composition-dependent fuel characteristic of the first fuel and the determined at least one second composition-dependent fuel characteristic of the second fuel, at least one fuel third composition-dependent characteristic of the resultant fuel in the fuel tank after refueling; and
- controlling the propulsion system based on the calculated at least one third composition-dependent fuel characteristic of the resultant fuel in the fuel tank after refueling.

16. The method of claim 15, wherein the obtaining at least one first composition-dependent fuel characteristic of the first fuel present in the fuel tank prior to refueling comprises detecting at least one feature of the composition of the first fuel present in the fuel tank.

17. The method of claim 15, wherein the obtaining at least one first composition-dependent fuel characteristic of the first fuel present in the fuel tank prior to refueling comprises obtaining a previously-calculated at least one third composition-dependent fuel characteristic of a previous resultant fuel in the fuel tank produced via a previous refueling of the aircraft, wherein the first fuel is the previous resultant fuel.

18. A propulsion system for an aircraft comprising:
- a gas turbine engine;
- a fuel tank arranged to contain a fuel to power the gas turbine engine; and
- a fuel composition tracker configured to:
  - store current fuel characteristic data, the fuel characteristic data comprising at least one first composition-dependent fuel characteristic of a first fuel present in the fuel tank prior to refueling the aircraft;
  - obtain at least one second composition-dependent fuel characteristic of a second fuel added to the fuel tank on refuelling;
  - calculate, based on both the at least one first composition-dependent fuel characteristic of the first fuel and the obtained at least one second composition-dependent fuel characteristic of the second fuel, at least one third composition-dependent fuel characteristic of a resultant fuel in the fuel tank after refueling the aircraft, the resultant fuel comprising the first fuel and the second fuel; and
  - update the stored at least one first composition-dependent fuel characteristic of the first fuel with the at least one third composition-dependent fuel characteristic of the resultant fuel.

19. The propulsion system of claim 18 wherein the fuel characteristic data is fuel composition data, including at least one parameter of a hydrocarbon distribution of the first fuel.

* * * * *